(12) United States Patent
Keasling et al.

(10) Patent No.: US 8,257,957 B2
(45) Date of Patent: Sep. 4, 2012

(54) PRODUCTION OF ISOPRENOIDS AND ISOPRENOID PRECURSORS

(75) Inventors: Jay D. Keasling, Berkeley, CA (US); Farnaz Nowroozi, Berkeley, CA (US); Douglas J. Pitera, Oakland, CA (US); Jennifer Anthony, Aston, PA (US); Jack D. Newman, Berkeley, CA (US); Larry Anthony, Aston, PA (US)

(73) Assignees: The Regents of the University of California, Oakland, CA (US); Amyris Biotechnologies, Inc., Emeryville, CA (US)

( * ) Notice: Subject to any disclaimer, the term of this patent is extended or adjusted under 35 U.S.C. 154(b) by 25 days.

(21) Appl. No.: 12/439,812

(22) PCT Filed: Sep. 25, 2007

(86) PCT No.: PCT/US2007/020790
§ 371 (c)(1),
(2), (4) Date: Dec. 14, 2009

(87) PCT Pub. No.: WO2008/039499
PCT Pub. Date: Apr. 3, 2008

(65) Prior Publication Data
US 2010/0112672 A1 May 6, 2010

Related U.S. Application Data

(60) Provisional application No. 60/826,970, filed on Sep. 26, 2006.

(51) Int. Cl.
*C12N 1/21* (2006.01)
*C12N 5/07* (2010.01)
*C12N 1/19* (2006.01)

(52) U.S. Cl. ............... 435/252.33; 435/254.21; 435/348

(58) Field of Classification Search .................. None
See application file for complete search history.

(56) References Cited

U.S. PATENT DOCUMENTS

| | | | |
|---|---|---|---|
| 7,172,886 B2 | 2/2007 | Keasling et al. | |
| 7,183,089 B2 | 2/2007 | Keasling et al. | |
| 7,192,751 B2 | 3/2007 | Keasling et al. | |
| 2002/0051998 A1 | 5/2002 | Schmidt-Dannert et al. | |
| 2004/0005678 A1 | 1/2004 | Keasling et al. | |
| 2004/0161819 A1 | 8/2004 | Aharoni et al. | |

FOREIGN PATENT DOCUMENTS

| WO | WO-2006-014837 | 2/2006 |
|---|---|---|
| WO | WO-2006-085899 | 8/2006 |
| WO | WO-2007-005604 | 1/2007 |

OTHER PUBLICATIONS

Dorsey et al. (The Inhibition of Mevalonic acid by Geranyl and Farnesyl Pyrophosphates. JBC 1968, vol. 243, pp. 4667-4670.*
Voyanova Staphylococcus aureus Mevalonate Kinase: Isolation and Characterization of an Enzyme of the Isoprenoid Biosynthetic Pathway J Bacteriol. Jan. 2004; 186(1): 61-67.*
Houten et al. Biochemical and genetic aspects of mevalonate kinase and its deficiency Biochimica et Biophysica Acta 1529 (2000) 19^32.*
Martin et al. Engineering a mevalonate pathway in *Escherichia coli* for production of terpenoids. (2003) Nat. Biotech. 21(7):796-802.
Farmer et al. Precursor balancing for metabolic engineering of lycopene production in *Escherichia coli*.(2001) Biotechnol. Prog. 17:57-61.
Kajiwara et al. Expression of an exogenous isopentenyl diphosphate isomerase gene enhances isoprenoid biosynthesis in *Escherichia coli*.(1997) Biochem. J. 324:421-426.
Kim et al. Metabolic engineering of the nonmevalonate isopentenyl diphosphate synthesis pathway in *Escherichia coli* enhances lycopene production. (2001) Biotechnol. Bioeng. 72:408-415.
Hamano Yoshimitsu, et al., "Cloning of a gene cluster encoding anzymesresponsible for the mevalonate pathway from a terpenoid-antibiotic-producing Streptomyces strain", Bioscience Biotechnology Biochemistry, 2001, vol. 65 (7), pp. 1627-1635.
Picaud, et al. "Expression, purification, and characterization of recombinant amorpha-4,11-dien synthase for Artemisia annua L", Archives of Biochemistry and Biophysics, 2005, vol. 436 (2), pp. 215-226.

* cited by examiner

*Primary Examiner* — Kagnew H Gebreyesus
(74) *Attorney, Agent, or Firm* — Paula A. Borden; Bozicevic, Field & Francis LLP.

(57) ABSTRACT

The present invention provides genetically modified host cells and use of same for producing isoprenoid compounds.

27 Claims, 11 Drawing Sheets

PRODUCTION OF ISOPRENOIDS AND ISOPRENOID PRECURSORS

CROSS-REFERENCE

This application claims the benefit of priority of U.S. Provisional Application No. 60/826,970, filed on Sep. 26, 2006, which application is incorporated herein by reference in its entirety.

BACKGROUND

Isoprenoids are ubiquitous in nature. They comprise a diverse family of over 40,000 individual products, many of which are vital to living organisms. Isoprenoids serve to maintain cellular fluidity, electron transport, and other metabolic functions. A vast number of natural and synthetic isoprenoids are useful as pharmaceuticals, cosmetics, perfumes, pigments and colorants, fungicides, antiseptics, nutraceuticals, and fine chemical intermediates.

An isoprenoid product is typically composed of repeating five-carbon isopentenyl diphosphate (IPP) units, although irregular isoprenoids and polyterpenes have been reported. In nature, isoprenoids are synthesized by consecutive condensations of their precursor IPP and its isomer dimethylallyl pyrophosphate (DMAPP). Two pathways for these precursors are known. Eukaryotes, with the exception of plants, generally use the mevalonate-dependent (MEV) pathway to convert acetyl coenzyme A (acetyl-CoA) to IPP, which is subsequently isomerized to DMAPP. Prokaryotes, with some exceptions, typically employ only the mevalonate-independent or deoxyxylulose-5-phosphate (DXP) pathway to produce IPP and DMAPP. Plants use both the MEV pathway and the DXP pathway.

Traditionally, isoprenoids have been manufactured by extraction from natural sources such as plants, microbes, and animals. However, the yield by way of extraction is usually very low due to certain limitations. First, most isoprenoids accumulate in nature in only small amounts. Second, the source organisms in general are not amenable to the large-scale cultivation that is necessary to produce commercially viable quantities of a desired isoprenoid. Third, the requirement of certain toxic solvents for isoprenoid extraction necessitates special handling and disposal procedures, thus complicating the commercial production of isoprenoids.

The elucidation of the MEV and DXP metabolic pathways has made biosynthetic production of isoprenoids feasible. For instance, microbes have been engineered to overexpress a part of or the entire mevalonate pathway for production of the isoprenoid amorpha-4,11-diene. Other efforts have focused on balancing the pool of glyceraldehyde-3-phosphate and pyruvate, or on increasing the expression of 1-deoxy-D-xylulose-5-phosphate synthase (dxs) and IPP isomerase (idi).

Nevertheless, given the very large quantities of isoprenoid products needed for many commercial applications, there remains a need for expression systems and fermentation procedures that produce even more isoprenoids than available with current technologies.

Literature

U.S. Pat. Nos. 7,172,886 and 7,192,751; Farmer et al. (2001) Biotechnol. Prog. 17:57-61; Kajiwara et al. (1997) Biochem. J. 324:421-426; and Kim et al. (2001) Biotechnol. Bioeng. 72:408-415; Martin et al. (2003) Nat. Biotech. 21(7): 796-802; U.S. Pat. No. 7,183,089;

SUMMARY OF THE INVENTION

The present invention provides genetically modified host cells and use of same for producing isoprenoid compounds.

DEFINITIONS

Figure 1:
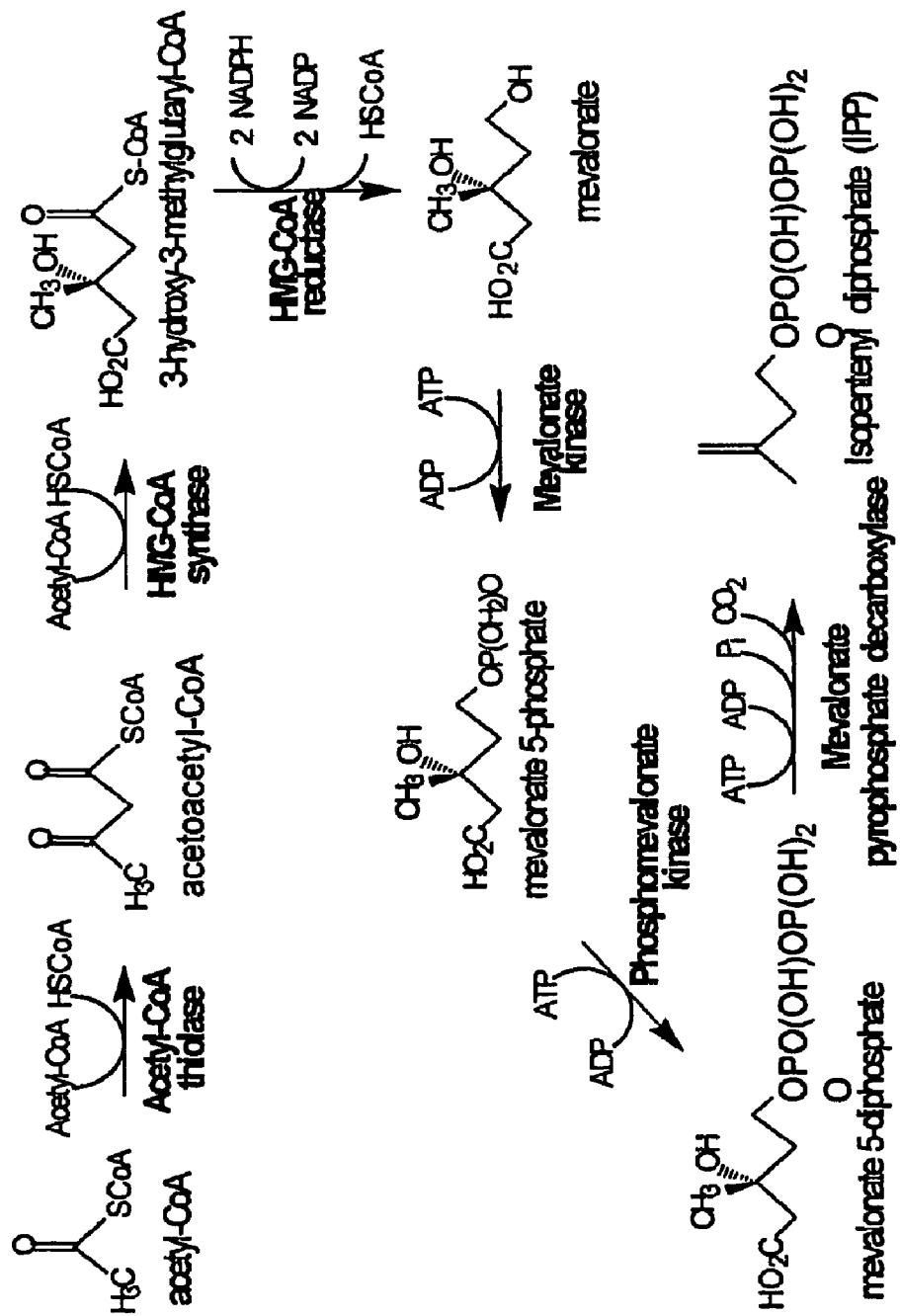
FIG. 1 is a schematic representation of the mevalonate (MEV) pathway for the production of isopentenyl diphosphate (IPP).

The terms "isoprenoid," "isoprenoid compound," "terpene," "terpene compound," "terpenoid," and "terpenoid compound" are used interchangeably herein, and refer to any compound that is capable of being derived from IPP. The number of C-atoms present in the isoprenoids is typically evenly divisible by five (e.g., C5, C10, C15, C20, C25, C30 and C40). Irregular isoprenoids and polyterpenes have been reported, and are also included in the definition of "isoprenoid." Isoprenoid compounds include, but are not limited to, monoterpenes, diterpenes, triterpenes; sesquiterpenes, and polyterpenes.

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" (also referred to a "terpene cyclase") refers to any enzyme that enzymatically modifies IPP, DMAPP, or a polyprenyl pyrophosphate, such that a terpenoid precursor compound is produced. The term "terpene synthase" includes enzymes that catalyze the conversion of a prenyl diphosphate into an isoprenoid or isoprenoid precursor.

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and farnesyl pyrophosphate" are interchangeable; etc.

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The mevalonate pathway is illustrated schematically in FIG. 1. The "top half" of the mevalonate pathway refers to the enzymes responsible for the conversion of acetyl-CoA to mevalonate.

The term "1-deoxy-D-xylulose 5-diphosphate pathway" or "DXP pathway" is used herein to refer to the pathway that converts glyceraldehyde-3-phosphate and pyruvate to IPP and DMAPP through a DXP pathway intermediate.

As used herein, the term "prenyl transferase" is used interchangeably with the terms "isoprenyl diphosphate synthase" and "polyprenyl synthase" (e.g., "GPP synthase," "FPP synthase," "GGPP synthase," etc.) to refer to an enzyme that catalyzes the consecutive 1'-4 condensation of isopentenyl diphosphate with allylic primer substrates, resulting in the formation of prenyl diphosphates of various chain lengths.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell. For example, the nucleic acids encoding HMGS, mevalonate kinase, and phosphomevalonate kinase in represent exogenous nucleic acids to *E. coli*.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence that is endogenous to the host microorganism or host cell) but is either produced in an unnatural (e.g., greater than expected or greater than naturally found) amount in the cell, or differs in sequence from the endogenous nucleotide sequence such that the same encoded protein (having the same or substantially the same amino acid sequence) as found endogenously is produced in an unnatural (e.g., greater than expected or greater than naturally found) amount in the cell; (c) the nucleic acid comprises two or more nucleotide sequences or segments that are not found in the same relationship to each other in nature, e.g., the nucleic acid is recombinant.

The term "heterologous polypeptide," as used herein, refers to a polypeptide that is not naturally associated with a given polypeptide. For example, an isoprenoid precursor-modifying enzyme that comprises a "heterologous transmembrane domain" refers to an isoprenoid precursor-modifying enzyme that comprises a transmembrane domain that is not normally associated with (e.g., not normally contiguous with; not normally found in the same polypeptide chain with) the isoprenoid precursor-modifying enzyme in nature.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The term "coding region," as used herein, refers to a contiguous stretch of nucleotides (a nucleotide sequence) that encodes a polypeptide. For example, an "MK-encoding coding region" or an "MK coding region" comprises a nucleotide sequence encoding mevalonate kinase.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject genetically modified prokaryotic host cell (e.g., a bacterium) is a prokaryotic host cell that, by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject genetically modified eukaryotic host cell is a eukaryotic host cell that, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, phenylalanine-tyrosine, lysine-arginine, alanine-valine, and asparagine-glutamine.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host.

Determination of preferred codons can be based on a survey of genes derived from the host cell where sequence information is available.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1× SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a genetically modified host cell" includes a plurality of such host cells and reference to "the isoprenoid compound" includes reference to one or more isoprenoid compounds and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides genetically modified host cells and use of same for producing isoprenoid or isoprenoid precursor compounds.

One method of making an isoprenoid or an isoprenoid precursor is to culture a host cell, where the host cell is capable of making the isoprenoid or isoprenoid precursor. Because the biosynthetic pathway for making an isoprenoid or an isoprenoid precursor involves multiple enzymes, the flux through the pathway may not be optimum or properly balanced. One method of correcting such imbalance is to modulate the activity levels of the pathway enzymes relative to one another. As described in more detail herein, increasing the level of mevalonate kinase, relative to the level of one or more other enzymes in the mevalonate pathway, provides for an increase in production levels of isoprenoid compounds, or precursors of isoprenoid compounds.

Isoprenoid compounds are synthesized from a universal five carbon precursor, isopentenyl pyrophosphate (IPP). There are two major pathways for converting a substrate to IPP: 1) the "mevalonate" pathway," which converts acetyl-CoA to IPP; and the "1-deoxy-D-xylulose 5-diphosphate pathway" (also referred to as the "DXP pathway"), which converts D-glyceraldehyde-3-phosphate and pyruvate to IPP and DMAPP.

Mevalonate pathway enzymes are depicted in FIG. 1. The mevalonate pathway comprises the following enzymatic reactions: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. Enzymes that carry out these reactions include acetoacetyl-CoA thiolase, hydroxymethylglutaryl-CoA synthase (HMGS), hydroxymethylglutaryl-CoA reductase (HMGR), mevalonate kinase (MK), phosphomevalonate kinase (PMK), and mevalonate pyrophosphate decarboxylase (MPD).

In the DXP pathway, pyruvate and D-glyceraldehyde-3-phosphate are converted via a series of reactions to IPP and DMAPP. The pathway involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH).

Eukaryotic cells other than plant cells use the mevalonate pathway exclusively to convert acetyl-CoA to IPP, which is subsequently isomerized to DMAPP. Plants use both the mevalonate and the DXP pathways for isoprenoid synthesis. Prokaryotes, with some exceptions, use the DXP pathway to produce IPP and DMAPP separately through a branch point.

Figure 2:
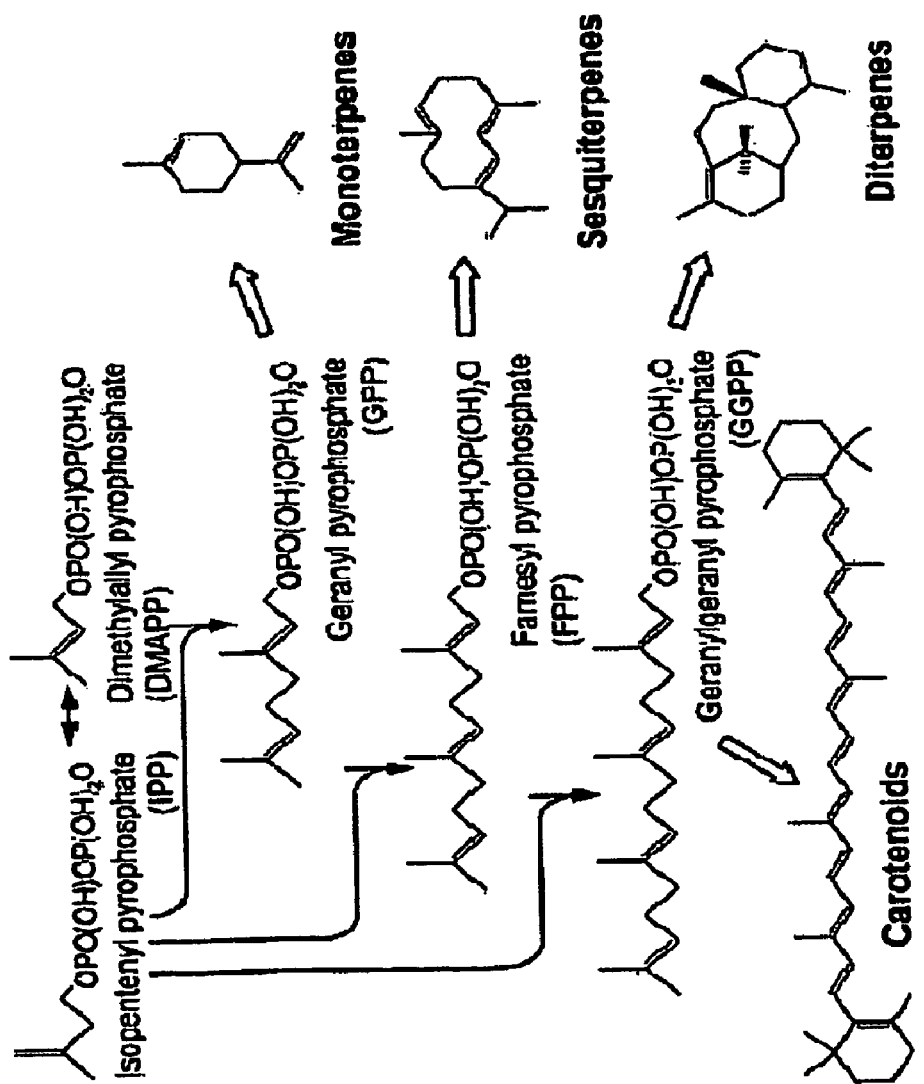
FIG. 2 is a schematic representation of isoprenoid metabolic pathways that result in the production of the isoprenoid biosynthetic pathway intermediates polyprenyl diphosphates geranyl diphosphate (GPP), farnesyl diphosphate (FPP), and geranylgeranyl diphosphate (GGPPP), from IPP and DMAPP.

The IPP produced by the mevalonate pathway can be isomerized to produce DMAPP. The IPP and/or the DMAPP can be acted on by prenyltransferases to produce polyprenyl pyrophosphates. For example, as shown in FIG. 2, IPP or DMAPP can be modified by prenyl transferases to generate the polyprenyl diphosphates geranyl diphosphate (GPP), farnesyl diphosphate (FPP), and geranylgeranyl diphosphate (GGPP). GPP and FPP are further modified by terpene synthases to generate monoterpenes and sesquiterpenes, respectively; and GGPP is further modified by terpene synthases to generate diterpenes and carotenoids. IPP and DMAPP are generated by one of two pathways: the mevalonate (MEV) pathway and the 1-deoxy-D-xylulose-5-phosphate (DXP) pathway.

Genetically Modified Host Cells

The present invention provides genetically modified host cells, and methods of using same to produce isoprenoid compounds. In some embodiments, a subject genetically modified host cell is genetically modified such that it produces mevalonate kinase at a level that is higher than the level of at least one of acetoacetyl-CoA thiolase, hydroxymethylglutaryl-CoA synthase (HMGS), hydroxymethylglutaryl-CoA reductase (HMGR), phosphomevalonate kinase (PMK), and mevalonate pyrophosphate decarboxylase (MPD). A subject method, described in more detail below, generally involves culturing a subject genetically modified host cell in vitro in a suitable medium, such that the genetically modified host cell converts a substrate to IPP and produces an isoprenoid compound.

In some embodiments, the level of MK produced in a subject genetically modified host cell is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 3-fold, at least about 4-fold, at least about 5-fold, at least about 7-fold, or at least about 10-fold, or more, higher than the level of one or more of acetoacetyl-CoA thiolase, HMGS, HMGR, PMK, and MPD.

For example, in some embodiments, the level of MK produced in a subject genetically modified host cell is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 3-fold, at least about 4-fold, at least about 5-fold, at least about 7-fold, or at least about 10-fold, or more, higher than the level of HMGS in the cell.

In other embodiments, the level of MK produced in a subject genetically modified host cell is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 3-fold, at least about 4-fold, at least about 5-fold, at least about 7-fold, or at least about 10-fold, or more, higher than the level of HMGR in the cell.

In other embodiments, the level of MK produced in a subject genetically modified host cell is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 3-fold, at least about 4-fold, at least about 5-fold, at least about 7-fold, or at least about 10-fold, or more, higher than the level of both HMGS and HMGR in the cell.

In some embodiments, the level of MK produced by a subject genetically modified host cell is a least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 3-fold, at least about 4-fold, at least about 5-fold, at least about 10-fold, at least about 25-fold, at least about 50-fold, or at least about 100-fold, or more, higher than the level of MK produced by a host genetically modified with pMBI or with pMBIS. pMBI and pMBIS are described in U.S. Pat. No. 7,192,751.

Thus, for example, in some embodiments, where a subject genetically modified host cell is a prokaryotic cell, the level of MK produced by a subject genetically modified host cell is a least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 3-fold, at least about 4-fold, at least about 5-fold, at least about 10-fold, at least about 25-fold, at least about 50-fold, or at least about 100-fold, or more, higher than the level of MK produced by the same cell genetically modified with pMBI or pMBIS.

In some embodiments, the molar ratio of MK polypeptide in a subject genetically modified host cell relative to one or more of acetoacetyl-CoA thiolase, HMGS, HMGR, PMK, and MPD polypeptide is from about 1.25:1 to about 100:1, or greater than 100:1. For example, in some embodiments, the molar ratio of MK relative to one or more of acetoacetyl-CoA thiolase, HMGS, HMGR, PMK, and MPD is from about 1.25:1 to about 1.5:1, from about 1.5:1 to about 2:1, from about 2:1 to about 2.5:1, from about 2.5:1 to about 3:1, from about 3:1 to about 5:1, from about 5:1 to about 10:1, from about 10:1 to about 25:1, from about 25:1 to about 50:1, or from about 50:1 to about 100:1.

The level of MK produced in a subject genetically modified host cell can be controlled in various ways. In some embodiments, the copy number of coding regions comprising nucleotide sequences encoding MK is higher than the copy number of coding regions encoding one or more of acetoacetyl-CoA thiolase, HMGS, HMGR, PMK, and MPD. In other embodiments, a nucleotide sequence encoding MK is under transcriptional control of (e.g., is operably linked to) a stronger promoter than the promoter to which one or more of a nucleotide sequence encoding one or more of acetoacetyl-CoA thiolase, HMGS, HMGR, PMK, and MPD is operably linked. In other embodiments, the level of MK is increased relative to the level of one or more of acetoacetyl-CoA thiolase, HMGS, HMGR, PMK, and MPD by increasing both the copy number of MK-encoding coding regions relative to the copy number of coding regions comprising nucleotide sequences encoding one or more of acetoacetyl-CoA thiolase, HMGS, HMGR, PMK, and MPD, and by increasing promoter strength of a promoter to which an MK coding sequence is operably linked, relative to the promoter strength of a promoter to which a nucleotide sequence encoding one or more of acetoacetyl-CoA thiolase, HMGS, HMGR, PMK, and MPD is operably linked.

In some embodiments, a subject genetically modified host cell comprises a nucleic acid comprising a nucleotide sequence encoding MK, where the MK-encoding nucleotide sequence is operably linked to a stronger promoter than the promoter to which an operon comprising nucleotide sequences encoding acetoacetyl-CoA thiolase, HMGS, and HMGR is operably linked. In other embodiments, a subject genetically modified host cell comprises a first nucleic acid comprising a nucleotide sequence encoding MK, where the first nucleic acid is a high copy number expression vector, and a second nucleic acid comprising nucleotide sequences encoding acetoacetyl-CoA thiolase, HMGS, and HMGR, where the second nucleic acid is a low copy number expression vector.

Controlling MK Levels by Copy Number of MK-Encoding Coding Regions

In some embodiments, a subject genetically modified host cell comprises a plurality of coding regions comprising a nucleotide sequence encoding MK; a nucleic acid comprising a nucleotide sequence encoding one or more mevalonate pathway enzymes other than mevalonate kinase; and a heterologous nucleic acid comprising a nucleotide sequence encoding a terpene synthase. The plurality of (e.g., two or more) MK-encoding coding regions can be on the same nucleic acid or on physically separated nucleic acids. For example, the two or more MK-encoding coding regions are in some embodiments all present in genomic DNA of the host cell. As another example, in some embodiments, a first MK-encoding coding regions is present in genomic DNA of the host cell; and a second MK-encoding coding region is present on an extra-chromosomal recombinant vector. As yet another example, in some embodiments, the two or more MK-encoding coding regions are both included in one or more extrachromosomal recombinant vector(s).

In some embodiments, a subject genetically modified host cell comprises a single copy of a coding region comprising nucleotide sequences encoding one or more of acetoacetyl-CoA thiolase, HMGS, HMGR, PMK, and MPD; two or more MK-encoding coding regions, each of which comprises nucleotide sequences encoding MK; and a heterologous nucleic acid comprising a nucleotide sequence encoding a terpene synthase. For example, in some embodiments, a subject genetically modified host cell comprising a single copy of a nucleic acid coding region comprising nucleotide sequences encoding one or more of acetoacetyl-CoA thiolase, HMGS, HMGR, PMK, and MPD, where the coding region is integrated into the host cell genome; two or more MK-encoding coding regions, each of which comprises nucleotide sequences encoding MK, where the two or more MK-encoding coding regions are extrachromosomal, such as extrachromosomal expression vectors that are not integrated into the host genome; and a heterologous nucleic acid comprising a nucleotide sequence encoding a terpene synthase.

In other embodiments, a subject genetically modified host cell comprises a nucleic acid comprising two or more coding regions encoding MK; a nucleic acid coding region comprising nucleotide sequences encoding one or more of acetoacetyl-CoA thiolase, HMGS, HMGR, PMK, and MPD; and a heterologous nucleic acid comprising a nucleotide sequence encoding a terpene synthase, where the ratio of the copy number of the MK coding regions to the copy number of the nucleic acid coding region comprising nucleotide sequences encoding one or more of acetoacetyl-CoA thiolase, HMGS, HMGR, PMK, and MPD is from about 1.5:1 to about 100:1, e.g., the ratio of the copy number of the MK-encoding coding regions to the copy number of the nucleic acid coding regions comprising nucleotide sequences encoding one or more of acetoacetyl-CoA thiolase, HMGS, HMGR, PMK, and MPD is from about 1.5:1 to about 2:1, from about 2:1 to about 2.5:1, from about 2.5:1 to about 3:1, from about 3:1 to about 5:1, from about 5:1 to about 10:1, from about 10:1 to about 25:1, from about 25:1 to about 50:1, or from about 50:1 to about 100:1.

For example, in some embodiments, a subject genetically modified host cell comprises at least two MK-encoding coding regions and a single copy of a coding region encoding one or more of acetoacetyl-CoA thiolase, HMGS, HMGR, PMK, and MPD. In some embodiments, a subject genetically modified host cell comprises two MK-encoding coding regions and a single copy of a coding region encoding acetoacetyl-CoA thiolase, HMGS, and HMGR.

In some embodiments, a subject genetically modified host cell comprises a plurality of MK-encoding coding regions, where the an MK-encoding coding region is present on a high copy number expression vector, such as a high copy number plasmid; a nucleic acid coding region comprising nucleotide sequences encoding one or more of acetoacetyl-CoA thiolase, HMGS, HMGR, PMK, and MPD, where the coding region encoding one or more of acetoacetyl-CoA thiolase, HMGS, HMGR, PMK, and MPD is present on a low copy number expression vector, such as a low copy number plasmid; and a heterologous nucleic acid comprising a nucleotide sequence encoding a terpene synthase.

In some embodiments, the copy number of an MK-encoding coding region in a subject genetically modified host cell is higher than the copy number of MK-encoding coding regions in a control host cell genetically modified with pMBI. In some embodiments, a subject genetically modified host cell comprises a plurality of coding regions comprising a nucleotide sequence encoding MK, where the MK-encoding coding regions are present on a nucleic acid comprising a p15A origin of replication (for a p15A on nucleotide sequence, see, e.g., nucleotides 4525-5321 of pAM39 (SEQ ID NO:3); and Selzer et al. (1983) Cell 32:119-129).

In some embodiments, a subject genetically modified host cell comprises a plurality of MK-encoding coding regions, where the MK-encoding coding regions are present in a high copy number plasmid; a nucleic acid coding region comprising nucleotide sequences encoding one or more of acetoacetyl-CoA thiolase, HMGS, HMGR, PMK, and MPD, where the coding region comprising nucleotide sequences encoding one or more of acetoacetyl-CoA thiolase, HMGS, HMGR, PMK, and MPD is present in a medium copy number plasmid; and a heterologous nucleic acid comprising a nucleotide sequence encoding a terpene synthase.

In some embodiments, a subject genetically modified host cell comprises a plurality of MK-encoding coding regions, where the MK-encoding coding regions are present in a medium copy number plasmid; a nucleic acid coding region comprising nucleotide sequences encoding one or more of acetoacetyl-CoA thiolase, HMGS, HMGR, PMK, and MPD, where the coding region comprising nucleotide sequences encoding one or more of acetoacetyl-CoA thiolase, HMGS, HMGR, PMK, and MPD is present in a low copy number plasmid; and a heterologous nucleic acid comprising a nucleotide sequence encoding a terpene synthase.

In other embodiments, a subject genetically modified host cell comprises a first nucleic acid comprising an MK-encoding coding region, where the first nucleic acid is a high copy number expression vector; a second nucleic acid comprising nucleotide sequences encoding acetoacetyl-CoA thiolase, HMGS, and HMGR, where the second nucleic acid is a low copy number expression vector; and a heterologous nucleic acid comprising a nucleotide sequence encoding a terpene synthase.

Low copy number plasmids generally provide fewer than about 20 plasmid copies per cell (e.g., from about 1 plasmid copy per cell to about 5 plasmid copies per cell, from about 5 plasmid copies per cell to about 10 plasmid copies per cell, from about 10 plasmid copies per cell to about 15 plasmid copies per cell, or from about 15 plasmid copies per cell to about 20 plasmid copies per cell); medium copy number plasmids generally provide from about 20 plasmid copies per cell to about 50 plasmid copies per cell, or from about 20 plasmid copies per cell to about 80 plasmid copies per cell; and high copy number plasmids generally provide from about 80 plasmid copies per cell to about 200 plasmid copies per cell, or more than 200 plasmid copies per cell.

Suitable low copy expression vectors for prokaryotic cells (e.g., *Escherichia coli*) include, but are not limited to, pACYC184, pBeloBac11, pBR332, pBAD33, pBBR1MCS and its derivatives, pSC101, SuperCos (cosmid), and pWE15 (cosmid). Suitable medium copy expression vectors for prokaryotic cells (e.g., *E. coli*) include, but are not limited to pTrc99A, pBAD24, and vectors containing a ColE1 origin of replication and its derivatives. Suitable high copy number expression vectors for prokaryotic cells (e.g., *E. coli*) include, but are not limited to, pUC, pBluescript, pGEM, and pTZ vectors.

Suitable low-copy (centromeric) expression vectors for eukaryotic cells (e.g., yeast cells) include, but are not limited to, pRS415 and pRS416 (Sikorski & Hieter (1989) *Genetics* 122:19-27). Suitable high-copy 2 micron expression vectors for eukaryotic cells (e.g., yeast cells) include, but are not limited to, pRS425 and pRS426 (Christainson et al. (1992) *Gene* 110:119-122). Alternative 2 micron expression vectors include non-selectable variants of the 2 micron vector (Bruschi & Ludwig (1988) *Curr. Genet.* 15:83-90) or intact 2 micron plasmids bearing an expression cassette (as exemplified in U.S. Pat. Application No. 20050084972).

Controlling MK Levels by Promoter Strength

In some embodiments, a subject genetically modified host cell comprises a plurality of nucleic acid coding regions comprising nucleotide sequences encoding MK, where the MK-encoding coding regions are each operably linked to (e.g., under transcriptional control of) a first transcriptional control element (e.g., a first promoter); a nucleic acid comprising a nucleotide sequence encoding one or more mevalonate pathway enzymes other than mevalonate kinase (e.g., encoding one or more of acetoacetyl-CoA thiolase, HMGS, HMGR, PMK, and MPD), where the nucleotide sequence(s) encoding one or more of acetoacetyl-CoA thiolase, HMGS, HMGR, PMK, and MPD is operably linked to (e.g., under transcriptional control of) a second transcriptional control element (e.g., a second promoter); and a heterologous nucleic acid comprising a nucleotide sequence encoding a terpene synthase, where the first transcriptional control element is stronger than the second transcriptional control element.

In some embodiments, a subject genetically modified host cell comprises a plurality of nucleic acid coding regions comprising nucleotide sequences encoding MK, where the MK-encoding coding regions are each operably linked to (e.g., under transcriptional control of) a first promoter; a nucleic acid comprising a nucleotide sequence encoding one or more mevalonate pathway enzymes other than mevalonate kinase (e.g., encoding one or more of acetoacetyl-CoA thiolase, HMGS, HMGR, PMK, and MPD), where the nucleotide sequence(s) encoding one or more of acetoacetyl-CoA thiolase, HMGR, PMK, and MPD is operably linked to (e.g., under transcriptional control of) a second promoter, where the first promoter is stronger than the second promoter; and a heterologous nucleic acid comprising a nucleotide sequence encoding a terpene synthase.

In some embodiments, a coding region is contained within an operon. In some embodiments, a subject genetically modified host cell comprises a nucleic acid comprising a first operon comprising nucleotide sequences encoding MX, PMK, and MPD, where the first operon is operably linked to a first promoter; a nucleic acid comprising a second operon comprising nucleotide sequences encoding acetoacetyl-CoA thiolase, HMGS, and HMGR, where the second operon is operably linked to a second promoter, where the first promoter is stronger than the second promoter; and a heterologous nucleic acid comprising a nucleotide sequence encoding a terpene synthase.

Regulatory elements include, for example, promoters and operators. A promoter is a sequence of nucleotides that initiates and controls the transcription of a nucleic acid sequence by an RNA polymerase enzyme. An operator is a sequence of nucleotides adjacent to the promoter that functions to control transcription of the desired nucleic acid sequence. The operator contains a protein-binding domain where a specific repressor protein can bind. In the absence of a suitable repressor protein, transcription initiates through the promoter. In the presence of a suitable repressor protein, the repressor protein binds to the operator and thereby inhibits transcription from the promoter.

In some embodiments of the present invention, promoters used in expression vectors are inducible. In other embodiments, the promoters used in expression vectors are constitutive. In some embodiments, one or more nucleic acid sequences are operably linked to an inducible promoter, and one or more other nucleic acid sequences are operably linked to a constitutive promoter.

Non-limiting examples of suitable promoters for use in prokaryotic host cells include a bacteriophage T7 RNA polymerase promoter; a trp promoter; a lac operon promoter; a hybrid promoter, for example, a lac/tac hybrid promoter, a tac/trc hybrid promoter, a trp/lac promoter, a T7/lac promoter, a trc promoter, a tac promoter, and the like; an araBAD promoter; in vivo regulated promoters, such as an ssaG promoter or a related promoter (see, for example, U.S. Patent Publication No. 20040131637), a pagC promoter (Pulkkinen and Miller, J. Bacteriol. (1991) 173(1):86-93; Alpuche-Aranda at al. (1992) Proc. Natl. Acad. Sci. USA. 89(21): 10079-83), a nirB promoter (Harborne et al. (1992) Mol. Micro. 6:2805-2813), and the like (see, for example, Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, for example, a consensus sigma70 promoter (see, for example, GenBank Accession Nos. AX798980, AX798961, and AX798183); a stationary phase promoter, for example, a dps promoter, an spy promoter, and the like; a promoter derived from the pathogenicity island SPI-2 (see, for example, WO96/17951); an actA promoter (see, for example, Shetron-Rama et al. (2002) Infect. Immun. 70:1087-1096); an rpsM promoter (see, for example, Valdivia and Falkow (1996) Mol. Microbiol. 22:367 378); a tet promoter (see, for example, Hillen et al. (1989) In Saenger W. and Heinemann U. (eds) Topics in Molecular and Structural Biology, Protein-Nucleic Acid Interaction. Macmillan, London, UK, Vol. 10, pp. 143-162); an SP6 promoter (see, for example, Melton et al. (1984) Nucl. Acids Res. 12:7035-7056); and the like.

In another embodiment of the present invention, the total activity of a heterologous mevalonate kinase relative to other mevalonate pathway enzymes in a host microorganism is increased by expressing the enzyme from a strong promoter. In some embodiments, the mevalonate kinase-encoding nucleotide sequence is operably linked to a promoter that is a stronger promoter than the $p_{LAC}$ promoter (SEQ ID NO:21), e.g., the MK-encoding nucleotide sequence is operably linked to a promoter that is at least about 10%, at least about 25%, at least about 50%, at least about 2-fold, at least about 5-fold, or at least about 10-fold, or more, stronger than a $p_{LAC}$ promoter having a nucleotide sequence as set forth in SEQ ID NO:21.

Suitable strong promoters for use in prokaryotic cells (e.g., *Escherichia coli*) include, but are not limited to, a lacUV5 promoter (see, e.g., SEQ ID NO:22), Trc, Tac, T5, T7, and $P_{Lambda}$. In another embodiment of the present invention, the total activity of the mevalonate kinase in a host microorganism is increased by expressing the enzyme from a strong promoter on a high copy number plasmid. Suitable examples, for use in prokaryotic cells (e.g., *Escherichia coli*) include, but are not limited to using Trc, Tac, T5, T7, and $P_{Lambda}$ promoters with pBAD24, pBAD18, pGEM, pBluescript, pUC, and pTZ vectors.

Non-limiting examples of suitable promoters for use in eukaryotic host cells include, but are not limited to, a CMV immediate early promoter, an HSV thymidine kinase promoter, an early or late SV40 promoter, LTRs from retroviruses, and a mouse metallothionein-I promoter.

Non-limiting examples of suitable constitutive promoters for use in prokaryotic host cells include a sigma70 promoter (for example, a consensus sigma70 promoter). Non-limiting examples of suitable inducible promoters for use in bacterial host cells include the pL of bacteriophage λ; Plac; Ptrp; Ptac (Ptrp-lac hybrid promoter); an isopropyl-beta-D44 thiogalactopyranoside (IPTG)-inducible promoter, for example, a lacZ promoter; a tetracycline inducible promoter; an arabinose inducible promoter, for example, PBAD (see, for example, Guzman et al. (1995) J. Bacteriol. 177:4121-4130); a xylose-inducible promoter, for example, Pxyl (see, for example, Kim et al. (1996) Gene 181:71-76); a GAL1 promoter; a tryptophan promoter; a lac promoter; an alcohol-inducible promoter, for example, a methanol-inducible promoter, an ethanol-inducible promoter; a raffinose-inducible promoter, a heat-inducible promoter, for example, heat inducible lambda PL promoter; a promoter controlled by a heat-sensitive repressor (for example, CI857-repressed lambda-based expression vectors; see, for example, Hoffmann et al. (1999) *FEMS* Microbiol Lett. 177(2):327-34); and the like.

Non-limiting examples of suitable constitutive promoters for use in yeast host cells include an ADH1, an ADH2, a PGK, or a LEU2 promoter. Non-limiting examples of suitable inducible promoters for use in yeast host cells include, but are not limited to, a divergent galactose-inducible promoter such as a GAL 1 or a GAL 10 promoter (West at al. (1984) Mol. Cell. Biol. 4(11):2467-2478), or a CUP1 promoter. Where desired, the promoter that is stronger than a native *E. coli* Lac promoter.

Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25.).

Mevalonate Pathway Enzymes

The mevalonate pathway comprises: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The mevalonate pathway enzymes required for production of IPP vary, depending on the culture conditions.

In some embodiments, a subject genetically modified host cell comprises a nucleic acid comprising nucleotide sequences encoding a mevalonate kinase, as described above; a nucleic acid comprising a nucleotide sequence encoding one or more mevalonate pathway enzymes other than mevalonate kinase; and a heterologous nucleic acid comprising a nucleotide sequence encoding a terpene synthase.

Nucleotide Sequences Encoding Mevalonate Pathway Enzymes

Nucleotide sequences encoding mevalonate (MEV) pathway gene products are known in the art, and any known MEV pathway gene product-encoding nucleotide sequence can used to generate a subject genetically modified host cell. For example, nucleotide sequences encoding acetoacetyl-CoA thiolase, HMGS, HMGR, MK., PMK, MPD, and IDI are known in the art. The following are non-limiting examples of known nucleotide sequences encoding MEV pathway gene products, with GenBank Accession numbers and organism following each MEV pathway enzyme, in parentheses: acetoacetyl-CoA thiolase: (NC_000913 REGION: 2324131 . . . 2325315; *E. coli*), (D49362; *Paracoccus denitrificans*), and (L20428; *Saccharomyces cerevisiae*); HMGS: (NC_001145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), and (BT007302; *Homo sapiens*); HMGR: (NM_206548; *Drosophila melanogaster*), (NM_204485; *Gallus gallus*), (AB015627; *Streptomyces* sp. KO-3988), (AF542543; *Nicotiana attenuata*), (AB037907; *Kitasatospora griseola*), (AX128213, providing the sequence encoding a truncated HMGR; *Saccharomyces cerevisiae*), and (NC 001145: complement (115734 . . . 118898; *Saccharomyces cerevisiae*)); MK: (L77688; *Arabidopsis thaliana*), and (X55875; *Saccharomyces cerevisiae*); PMK: (AF429385; *Hevea brasiliensis*), (NM_006556; *Homo sapiens*), (NC_001145. complement 712315 . . . 713670; *Saccharomyces cerevisiae*); MPD: (X97557; *Saccharomyces cerevisiae*), (AF290095; *Enterococcus faecium*), and (U49260; *Homo sapiens*); and IDI: (NC_000913, 3031087 . . . 3031635; *E. coli*), and (AF082326; *Haematococcus pluvialis*).

A non-limiting example of nucleotide sequences encoding aceoacetyl-CoA thiolase, HMGS, and HMGR is set forth in FIGS. 13A-C (SEQ ID NO:1) of U.S. Pat. No. 7,183,089. A non-limiting example of nucleotide sequences encoding MK, PMK, MPD, and isopentenyl diphosphate isomerase (IDI) is set forth in FIGS. 16A-D of U.S. Pat. No. 7,183,089.

In some embodiments, the HMGR coding region is set forth in SEQ ID NO:13 of U.S. Pat. No. 7,183,089 (see also FIGS. 20A-C of U.S. Pat. No. 7,183,089), which encodes a truncated form of HMGR ("tHMGR") that lacks the transmembrane domain of wild-type HMGR. The transmembrane domain of HMGR contains the regulatory portions of the enzyme and has no catalytic activity.

The coding sequence of any known MEV pathway enzyme may be altered in various ways known in the art to generate targeted changes in the amino acid sequence of the encoded enzyme. The amino acid of a variant MEV pathway enzyme will usually be substantially similar to the amino acid sequence of any known MEV pathway enzyme, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

DXP Pathway Enzymes

The DXP pathway comprises: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), and 1-hydroxy-2-methyl-2-(E)-butenyl 4-diphosphate synthase (IspG).

In some embodiments, a subject genetically modified host cell comprises a nucleic acid comprising nucleotide sequences encoding a mevalonate kinase, as described above; a nucleic acid comprising a nucleotide sequence encoding one or more mevalonate pathway enzymes other than mevalonate kinase; and a heterologous nucleic acid comprising a nucleotide sequence encoding a terpene synthase; where an endogenous DXP pathway in the host cell is functionally disabled.

Prenyltransferases

In some embodiments, a subject genetically modified host cell comprises a nucleic acid comprising nucleotide sequences encoding a mevalonate kinase, as described above; a nucleic acid comprising a nucleotide sequence encoding one or more mevalonate pathway enzymes other than mevalonate kinase; a heterologous nucleic acid comprising a nucleotide sequence encoding a prenyltransferase; and a heterologous nucleic acid comprising a nucleotide sequence encoding a terpene synthase.

Prenyltransferases constitute a broad group of enzymes catalyzing the consecutive condensation of IPP resulting in the formation of prenyl diphosphates of various chain lengths. Suitable prenyltransferases include enzymes that catalyze the condensation of IPP with allylic primer substrates to form isoprenoid compounds with from about 2 isoprene units to about 6000 isoprene units or more, e.g., 2 isoprene units (Geranyl Pyrophosphate synthase), 3 isoprene units (Farnesyl pyrophosphate synthase), 4 isoprene units (geranylgeranyl pyrophosphate synthase), 5 isoprene units, 6 isoprene units (hexadecylpyrophosphate synthase), 7 isoprene units, 8 isoprene units (phytoene synthase, octaprenyl pyrophosphate synthase), 9 isoprene units (nonaprenyl pyrophosphate synthase, 10 isoprene units (decaprenyl pyrophosphate synthase), from about 10 isoprene units to about 15 isoprene units, from about 15 isoprene units to about 20 isoprene units, from about 20 isoprene units to about 25 isoprene units, from about 25 isoprene units to about 30 isoprene units, from about 30 isoprene units to about 40 isoprene units, from about 40 isoprene units to about 50 isoprene units, from about 50 isoprene units to about 100 isoprene units, from about 100 isoprene units to about 250 isoprene units, from about 250 isoprene units to about 500 isoprene units, from about 500 isoprene units to about 1000 isoprene units, from about 1000 isoprene units to about 2000 isoprene units, from about 2000 isoprene units to about 3000 isoprene units, from about 3000 isoprene units to about 4000 isoprene units, from about 4000 isoprene units to about 5000 isoprene units, or from about 5000 isoprene units to about 6000 isoprene units or more.

Suitable prenyltransferases include, but are not limited to, an E-isoprenyl diphosphate synthase, including, but not limited to, geranyl diphosphate (GPP) synthase, farnesyl diphosphate (FPP) synthase, geranylgeranyl diphosphate (GGPP) synthase, hexaprenyl diphosphate (HexPP) synthase, heptaprenyl diphosphate (HepPP) synthase, octaprenyl (OPP) diphosphate synthase, solanesyl diphosphate (SPP) synthase, decaprenyl diphosphate (DPP) synthase, chicle synthase, and gutta-percha synthase; and a Z-isoprenyl diphosphate synthase, including, but not limited to, nonaprenyl diphosphate (NPP) synthase, undecaprenyl diphosphate (UPP) synthase, dehydrodolichyl diphosphate synthase, eicosaprenyl diphosphate synthase, natural rubber synthase, and other Z-isoprenyl diphosphate synthases.

The nucleotide sequences of a numerous prenyl transferases from a variety of species are known, and can be used or modified for use in generating a subject genetically modified host cell. Nucleotide sequences encoding prenyl transferases are known in the art. See, e.g., Human farnesyl pyrophosphate synthetase mRNA (GenBank Accession No. J05262; *Homo sapiens*); farnesyl diphosphate synthetase (FPP) gene (GenBank Accession No. J05091; *Saccharomyces cerevisiae*); isopentenyl diphosphate:dimethylallyl diphosphate isomerase gene (J05090; *Saccharomyces cerevisiae*); Wang and Ohnuma (2000)*Biochim. Biophys. Acta* 1529:33-48; U.S. Pat. No. 6,645,747; *Arabidopsis thaliana* farnesyl pyrophosphate synthetase 2 (FPS2)/FPP synthetase 2/farnesyl diphosphate synthase 2 (At4g17190) mRNA (GenBank Accession No. NM 202836); *Ginkgo biloba* geranylgeranyl diphosphate synthase (ggpps) mRNA (GenBank Accession No. AY371321); *Arabidopsis thaliana* geranylgeranyl pyrophosphate synthase (GGPS1)/GGPP synthetase/farnesyltranstransferase (At4g36810) mRNA (GenBank Accession No. NM_119845); *Synechococcus elongatus* gene for farnesyl, geranylgeranyl, geranylfarnesyl, hexaprenyl, heptaprenyl diphosphate synthase (SelF-HepPS) (GenBank Accession No. AB016095); etc.

Terpene Synthases

A nucleic acid comprising a nucleotide sequence encoding any known terpene synthase can be used. Suitable terpene synthases include, but are not limited to, amorpha-4,11-diene synthase (ADS), beta-caryophyllene synthase, germacrene A synthase, 8-epicedrol synthase, valencene synthase, (+)-delta-cadinene synthase, germacrene C synthase, (E)-beta-farnesene synthase, Casbene synthase, vetispiradiene synthase, 5-epi-aristolochene synthase, Aristolchene synthase, beta-caryophyllene, alpha-humulene, (E,E)-alpha-farnesene synthase, (−)-beta-pinene synthase, Gamma-terpinene synthase, limonene cyclase, Linalool synthase, 1,8-cineole synthase, (+)-sabinene synthase, E-alpha-bisabolene synthase, (+)-bornyl diphosphate synthase, levopimaradiene synthase, Abietadiene synthase, isopimaradiene synthase,(E)-gamma-bisabolene synthase, taxadiene synthase, copalyl pyrophosphate synthase, kaurene synthase, longifolene synthase, gamma-humulene synthase, Delta-selinene synthase, beta-phellandrene synthase, limonene synthase, myrcene synthase, terpinolene synthase, (−)-camphene synthase, (+)-3-carene synthase, syn-copalyl diphosphate synthase, alpha-terpineol synthase, syn-pimara-7,15-diene synthase, ent-sandaaracopimaradiene synthase, stemer-13-ene synthase, E-beta-ocimene, S-linalool synthase, geraniol synthase, gamma-terpinene synthase, linalool synthase, E-beta-ocimene synthase, epi-cedrol synthase, alpha-zingiberene synthase, guaiadiene synthase, cascarilladiene synthase, cis-muuroladiene synthase, aphidicolan-16b-ol synthase, elizabethatriene synthase, sandalol synthase, patchoulol synthase, Zinzanol synthase, cedrol synthase, scareol synthase, copalol synthase, manool synthase, and the like.

Nucleotide sequences encoding terpene synthases are known in the art, and any known terpene synthase-encoding nucleotide sequence can used to genetically modify a host cell. For example, the following terpene synthase-encoding nucleotide sequences, followed by their GenBank accession numbers and the organisms in which they were identified, are known and can be used: (−)-germacrene D synthase mRNA (AY438099; *Populus balsamifera* subsp. *trichocarpa*×*Populus deltoids*); E,E-alpha-farnesene synthase mRNA (AY640154; *Cucumis sativus*); 1,8-cineole synthase mRNA (AY691947; *Arabidopsis thaliana*); terpene synthase 5 (TPS5) mRNA (AY518314; *Zea mays*); terpene synthase 4 (TPS4) mRNA (AY518312; *Zea mays*); myrcene/ocimene synthase (TPS10)(At2g24210) mRNA (NM_127982; *Arabidopsis thaliana*); geraniol synthase (GES) mRNA (AY362553; *Ocimum basilicum*); pinene synthase mRNA (AY237645; *Picea sitchensis*); myrcene synthase 1e20 mRNA (AY195609; *Antirrhinum majus*); (E)-β-ocimene synthase (0e23) mRNA (AY195607; *Antirrhinum majus*); E-β-ocimene synthase mRNA (AY151086; *Antirrhinum majus*); terpene synthase mRNA (AF497492; *Arabidopsis thaliana*); (−)-camphene synthase (AG6.5) mRNA (U87910; *Abies grandis*); (−)-4S-limonene synthase gene (e.g., genomic sequence) (AF326518; *Abies grandis*); delta-selinene synthase gene (AF326513; *Abies grandis*); amorpha-4,11-diene synthase mRNA (AJ251751; *Artemisia annua*); E-α-bisabolene synthase mRNA (AF006195; *Abies grandis*); gamma-humulene synthase mRNA (U92267; *Abies grandis*); δ-selinene synthase mRNA (U92266; *Abies grandis*); pinene synthase (AG3.18) mRNA (U87909; *Abies grandis*); myrcene synthase (AG2.2) mRNA (U87908; *Abies grandis*); etc.

Amino acid sequences of the following terpene synthases are found under the GenBank Accession numbers shown in parentheses, along with the organism in which each was identified, following each terpene synthase: (−)-germacrene D synthase (AAR99061; *Populus balsamifera* subsp. *trichocarpa*×*Populus* deltoids); D-cadinene synthase (P93665; *Gossypium hirsutum*); 5-epi-aristolochene synthase (Q40577; *Nicotiana tabacum*); E,E-alpha-farnesene synthase (AAU05951; *Cucumis sativus*); 1,8-cineole synthase (AAU01970; *Arabidopsis thaliana*); (R)-limonene synthase 1 (Q8L5K3; *Citrus limon*); syn-copalyl diphosphate synthase (AAS98158; *Oryza sativa*); a taxadiene synthase (Q9FT37; *Taxus chinensis*; Q93YA3; Taxus bacca; Q41594; *Taxus brevifolia*); a D-cadinene synthase (Q43714; *Gossypium arboretum*); terpene synthase 5 (AAS88575; *Zea mays*); terpene synthase 4 (AAS88573; *Zea mays*); terpenoid synthase (AAS79352; *Vitis vinifera*); geraniol synthase (AAR11765; *Ocimum basilicum*); myrcene synthase 1e20 (AA041727; *Antirrhinum majus*); 5-epi-aristolochene synthase 37 (AAP05762; *Nicotiana attenuata*); (+)-3-carene synthase (AAO73863; *Picea abies*); (−)-camphene synthase (AAB70707; *Abies grandis*); abietadiene synthase (AAK83563; *Abies grandis*); amorpha-4,11-diene synthase (CAB94691; *Artemisia annua*); trichodiene synthase (AAC49957; *Myrothecium roridum*); gamma-humulene synthase (AAC05728; *Abies grandis*); δ-selinene synthase (AAC05727; *Abies grandis*); etc.

Codon Optimization

In some embodiments, a nucleotide sequence encoding an enzyme (e.g., MK; a mevalonate pathway enzyme other than MK; a prenyltransferase; a terpene synthase) is modified to reflect the codon preference for the particular host cell. For example, the nucleotide sequence will in some embodiments be modified for yeast codon preference. See, e.g., Bennetzen and Hall (1982) *J. Biol. Chem.* 257(6): 3026-3031. As another non-limiting example, the nucleotide sequence will in other embodiments be modified for *E. coli* codon preference. See, e.g., Gouy and Gautier (1982) *Nucleic Acids Res.* 10(22): 7055-7074; Eyre-Walker (1996) *Mol. Biol. Evol.* 13(6):864-872. See also Nakamura et al. (2000) *Nucleic Acids Res.* 28(1):292. Such codon modification is also referred to as "codon optimization."

Expression Constructs

In some embodiments, a subject genetically modified host cell comprises a nucleic acid comprising nucleotide sequences encoding MK (as described above); a nucleic acid comprising a nucleotide sequence encoding one or more mevalonate pathway enzymes other than MK; and a heterologous nucleic acid comprising a nucleotide sequence encoding a terpene synthase; where one or more of the nucleic acids is present in an expression vector. In some embodiments, a subject genetically modified host cell comprises a nucleic acid comprising nucleotide sequences encoding MK (as described above); a nucleic acid comprising a nucleotide sequence encoding one or more mevalonate pathway enzymes other than MK; a heterologous nucleic acid comprising a nucleotide sequence encoding a terpene synthase; and a heterologous nucleic acid comprising a nucleotide sequence encoding a prenyltransferase; where one or more of the nucleic acids is present in an expression vector.

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as *E. coli* and yeast). Suitable vectors include chromosomal, nonchromosomal and synthetic DNA sequences.

Numerous suitable expression vectors are known to those of skill in the art, and many are commercially available. The following vectors are provided by way of example; for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXT1, pSG5 (Stratagene), pSVK3, pBPV, pMSG, and pSVLSV40 (Pharmacia). However, any other plasmid or other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996), *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035-7056); and the like.

Non-limiting examples of suitable eukaryotic promoters include CMV immediate early, HSV thymidine kinase, early and late SV40, LTRs from retrovirus, and mouse metallothionein-I. Suitable promoters for expression in yeast include, but are not limited to, CYC1, HIS3, GAL1, GAL10, ADH1, PGK, PHO5, GAPDH, ADC1, TRP1, URA3, LEU2, ENO, and TP1; and, e.g., AOX1 (e.g., for use in *Pichia*). Selection of the appropriate vector and promoter is well within the level of ordinary skill in the art. The expression vector may also contain a ribosome binding site for translation initiation and a transcription terminator. The expression vector may also include appropriate sequences for amplifying expression.

In addition, the expression vectors include one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as *E. coli*.

Generally, an expression vectors will include origins of replication and selectable markers permitting transformation of the host cell, e.g., the ampicillin resistance gene of *E. coli*, the *S. cerevisiae* TRP1 gene, etc.; and a promoter derived from a highly-expressed gene to direct transcription of the coding sequence. Such promoters can be derived from operons encoding glycolytic enzymes such as 3-phosphoglycerate kinase (PGK), α-factor, acid phosphatase, or heat shock proteins, among others.

In some embodiments, a nucleotide sequence encoding an enzyme (e.g., a mevalonate pathway enzyme; a terpene synthase; a prenyltransferase) is operably linked to an inducible promoter. Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter, an arabinose inducible promoter, e.g., $P_{BAD}$ (see, e.g., Guzman et al. (1995) *J. Bacteriol.* 177:4121-4130); a xylose-inducible promoter, e.g., Pxyl (see, e.g., Kim et al. (1996) *Gene* 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857-repressed lambda-based expression vectors; see, e.g., Hoffmann et al. (1999) *FEMS Microbiol Leu.* 177(2):327-34); and the like.

In some embodiments, a nucleotide sequence encoding an enzyme (e.g., a mevalonate pathway enzyme; a terpene synthase; a prenyltransferase) is operably linked to a constitutive promoter. Suitable constitutive promoters for use in prokaryotic cells are known in the art and include, but are not limited to, a sigma70 promoter, e.g., a consensus sigma70 promoter.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces,* 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

In some embodiments, a subject genetically modified host cell comprises a nucleic acid comprising nucleotide sequences encoding enzymes (e.g., a mevalonate pathway enzyme; a terpene synthase; a prenyltransferase), as described above, where each of the nucleic acids is contained on separate expression vectors. In other embodiments, two or more of the nucleic acids are contained in a single expression vector. Where two or more nucleic acids are contained in a single expression vector, in some embodiments, the nucleotide sequences will be operably linked to a common control element (e.g., a promoter). Where two or more nucleic acids are contained in a single expression vector, in some embodiments, the nucleotide sequences will be operably linked to different control elements (e.g., a promoters), e.g., different control elements are operably linked to enzyme-encoding nucleotide sequences separately on a single expression vector. For example, as noted above, in some embodiments, an MK-encoding nucleotide sequence is operably linked to a first promoter; and a nucleotide sequence encoding acetoacetyl-CoA thiolase, HMGS, and HMGR is operably linked to a second promoter.

Host Cells

In some embodiments, the genetically modified host cell is a eukaryotic cell. Suitable eukaryotic host cells include, but are not limited to, fungal cells, algal cells, insect cells, and plant cells. Suitable fungal host cells include, but are not limited to, Ascomycota, Basidiomycota, Deuteromycetes, *Fungi imperfecti, Saccharomyces cerevisiae, Saccharomyces* sp., *Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia* sp., *Pichia angusta, Kluyveromyces* sp., *Kluyveromyces lactic, Candida albicans, Aspergillus nidulans, Aspergillus niger, Aspergillus oryzae, Trichoderma reesei, Chrysosporium lucknowense, Fusarium* sp., *Fusarium graminearum, Fusarium venenatum*, and *Neurospora crassa*. Suitable algal host cells include, but are not limited to, *Chlamydomonas reinhardtii* and *Phormidium* sp. ATCC29409.

In other embodiments, the host cell is a prokaryotic cell. Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) J. Immunol. 148:1176-1181; U.S. Pat. No. 6,447,784; and Sizemore et al. (1995) Science 270: 299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei,* and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

In other embodiments, the host cell employed in the production method is a bacterial cell. Suitable bacterial hosts include, but are not limited to, any of a variety of gram-positive, gram-negative, or gram-variable bacteria such as microorganisms belonging to the genera *Escherichia, Corynebacterium, Brevibacterium, Bacillus, Microbacterium, Serratia, Pseudomonas, Agrobacterium, Alicyclobacillus, Anabaena, Anacystis, Arthrobacter, Azobacter, Chromatium, Erwinia, Methylobacterium, Rhodobacter, Rhodopseudomonas, Rhodospirillum, Scenedesmun, Strepromyces, Synnecoccus*, and *Zymomonas*. Examples of suitable host microorganisms used herein include *Escherichia coli, LactoBacillus* sp., *Lactococcus lactis, Salmonella* sp., *Salmonella enterica, Salmonella typhi, Salmonella typhimurium, Shigella* sp., *Shigella flexneri, Shigella sonnei, Shigella dysenteriae, Enterobacter sakazakii, Pseudomonas* sp. D-0110, *Pseudomonas pudica, Pseudomonas aeruginosa, Pseudomonas mevalonii, Rhodobacter sphaeroides, Rhodobacter capsulatus, Rhodospirillum rubrum; Rhodospirillum salexigens, Rhodospirillum salinarum, Rhodococcus* sp., *Mesorhizobium loti, Clostridium acetobutylicum, Clostridium tetani* E88, *Clostridium lituseburense, Clostridium saccharobutylicum, Clostridium perfringens, Clostridium beijerinckii, Fusobacterium nucleatum, Thermoanaerobacterium thermosaccharolyticum, Butyrivibrio fibrisolvens, Bacillus thuringiensis, Bacillus anthracis, Bacillus megaterium, Bacillus subtilis, Bacillus amyloliquefacines, LactoBacillus johnsonii, Acinetobacter, Roseburia* sp., *Faecalibacterium prausnitzii*, and *Coprococcus* sp., *Staphylococcus epidermidis, Staphylococcus haemolyticus, Staphylococcus aureus, Brevibacterium ammoniagenes, Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium glutamicum* ATCC14297, *Corynebacterium acetoacidophilum* ATCC13870, *Microbacterium ammoniaphilum* ATCC15354, *Serratia ficaria, Serratia fonticola, Serratia liquefaciens, Serratia marcescens, Agrobacterium radiobacter, Agrobacterium rhizogenes, Agrobacterium rubi, Anabaena cylindrica, Anabaena doliolum, Anbaena flos-aquae, Arthrobacter aurescens, Arthrobacter citreus, Arthrobacter globformis, Arthrobacter hydrocarboglutamicus, Arthrobacter mysorens, Arthrobacter nicotianae, Arthrobacter paraffineus, Arthrobacter protophonniae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorquens, Rhodopseudomonas blastica, Rhodopseudomonas marina, Rhodopseudomonas palustris, Streptomyces ambofaciens, Streptomyces aureofaciens, Streptomyces aureus, Streptomyces fungicidicus, Streptomyces griseochro-* mogenes, *Streptomyces griseus, Streptomyces lividans, Streptomyces olivogriseus, Streptomyces rameus, Streptomyces tanashiensis, Streptomyces vinaceus, Zymomonas mobilis*, and the like (see, for example, Carrier et al. (1992) J. Immunol. 148:1176-1181; U.S. Pat. No. 6,447,784; and Sizemore at al. (1995) Science 270:299-302).

In yet other embodiments, the bacterial host strain is non-pathogenic to humans. Examples of *Escherichia coli* strains that can be employed include common cloning strains such as DID, B, MG1655, W3110, BL21, DH10B, JM109, DH5alpha, XL1-Blue, XL2-Blue, MC1000, KY3276, W1485, HB101, No. 49, NY49, MP347, NM522, and derivatives thereof. In one embodiment, a RecA-strain of *Escherichia coli* is employed in the methods of the invention. In some embodiments, the *Escherichia coli* strain also produces IPP via the DXP pathway. In other embodiments, the *Escherichia coli* strain comprises a DXP pathway that is functionally disabled.

In some embodiments of the present invention, a subject genetically modified host cell is genetically modified such that an endogenous pathway enzyme is functionally disabled. Enzymes that can be inactivated in a host microorganism to increase production of IPP and compounds derived therefrom include, but are not limited to, pyruvate synthase, which when active uses acetyl-CoA (and carbon dioxide and reduced ferrodoxin) to produce pyruvate and thus reduces the supply of acetyl-CoA available for the production of IPP and compounds derived therefrom; acetyl-CoA synthetase, which when active uses coenzyme A (and propionate and ATP) to produce propionyl-CoA and thus reduces the supply of coenzyme A available for the production of acetyl-CoA; and pyruvate formate lyase, which when active uses coenzyme A (and 2-oxobutanoate) to produce propionyl-CoA and thus reduces the supply of coenzyme A available for the production of acetyl-CoA.

Methods for disabling genes encoding such enzymes are well known in the art, and include, but are not limited to, insertion of a mobile genetic element (for example, a transposon); deletion of all or part of the gene, such that the gene product is not made, or is truncated and is non-functional (that is, enzymatically inactive); mutation of the gene such that the gene product is not made, or is truncated and is nonfunctional; deletion or mutation of one or more control elements that control expression of the gene such that the gene product is not made; and the like.

Methods of Producing an Isoprenoid Compound

The present invention provides methods of producing an isoprenoid compound, the methods generally involving culturing a subject genetically modified host cell in a suitable medium under conditions that provide for production of the mevalonate pathway enzymes and the terpene synthase (and optionally also a heterologous prenyltransferase, as described above), such that an isoprenoid compound is produced by the cell in a recoverable amount. In some embodiments, a subject method further comprises recovering the isoprenoid compound, e.g., from the cell, from cell culture medium, or from both the cell and the cell culture medium.

Production of an isoprenoid or an isoprenoid precursor is increased in a subject genetically modified host cell, compared to a control, parent cell that is not so genetically modified. Thus, e.g., production of an isoprenoid or isoprenoid precursor is increased by at least about 10%, at least about 20%, at least about 50%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, in the genetically modified host cell, compared to the control host cell.

For example, production of an isoprenoid compound in a subject genetically modified host cell is at least about 10%, at least about 20%, at least about 50%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, or at least about 500-fold, or more, higher than the level of production of the isoprenoid compound in a host cell genetically modified with pMevT, pMBIS, and a heterologous nucleic acid encoding a terpene synthase. The nucleotide sequences of pMevT and pMBIS can be found in U.S. Pat. Nos. 7,192,751 and 7,183,089; see, e.g., pMevT, SEQ ID NO:3 of U.S. Pat. No. 7,183,089; MecT operon, SEQ ID NO:8 of U.S. Pat. No. 7,192,751; pMBIS, SEQ ID NO:4 of U.S. Pat. No. 7,183,089; and MBIS operon, SEQ ID NO:13 of U.S. Pat. No. 7,192,751).

As another example, in some embodiments, the level of an isoprenoid compound produced in a subject genetically modified host cell is at least about 500 mg/L, at least about 600 mg/L, at least about 700 mg/L, at least about 800 mg/L, at least about 900 mg/L, at least about 1000 mg/L, at least about 1200 mg/L, at least about 1400 mg/L, at least about 1600 mg/L, at least about 1800 mg/L, or at least about 2000 mg/L, after about 10 hours to about 20 hours, about 20 hours to about 30 hours, about 30 hours to about 40 hours, or about 40 hours to about 50 hours, in culture. For example, in some embodiments, the level of an isoprenoid compound produced in a subject genetically modified host cell is from about 500 mg/L to about 600 mg/L, from about 600 mg/L to about 700 mg/L, from about 700 mg/L to about 800 mg/L, from about 800 mg/L to about 1000 mg/L, from about 1000 mg/L to about 1200 mg/L, from about 1200 mg/L to about 1400 mg/L, from about 1400 mg/L to about 1600 mg/L, from about 1600 mg/L to about 1800 mg/L, or from about 1800 mg/L to about 2000 mg/L, or greater than 2000 mg/L, after about 10 hours to about 20 hours, about 20 hours to about 30 hours, about 30 hours to about 40 hours, or about 40 hours to about 50 hours, in culture. In some embodiments, the level of an isoprenoid compound produced in a subject genetically modified host cell is at least about 500 mg/L, at least about 600 mg/L, at least about 700 mg/L, at least about 800 mg/L, at least about 900 mg/L, at least about 1000 mg/L, at least about 1200 mg/L, at least about 1400 mg/L, at least about 1600 mg/L, at least about 1800 mg/L, or at least about 2000 mg/L, where the level is after about 10 hours to about 20 hours, about 20 hours to about 30 hours, about 30 hours to about 40 hours, or about 40 hours to about 50 hours, after induction (e.g., where one or more of the nucleotide sequences encoding an enzyme (e.g., MK, mevalonate enzyme other than MK, prenyltransferase, terpene synthase) is operably linked to an inducible promoter).

In some embodiments, the growth rate of a subject genetically modified host cell is greater than the growth rate of a control cell. For example, in some embodiments, a subject genetically modified host cell grows at a rate that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% or 2-fold, at least about 5-fold, at least about 10-fold, or more, higher than the growth rate of a control cell. Cell growth o is readily determined using well-known methods, e.g., optical density (OD) measurement at about 600 nm ($OD_{600}$) of liquid cultures of bacteria; colony size; growth rate; and the like.

Isoprenoids that can be produced using the method of the invention include, but are not limited to, monoterpenes, including but not limited to, limonene, citranellol, geraniol, menthol, perillyl alcohol, linalool, thujone; sesquiterpenes, including but not limited to, periplanone B, gingkolide B, amorphadiene, artemisinin, artemisinic acid, valencene, nootkatone, epi-cedrol, epi-aristolochene, farnesol, gossypol, sanonin, periplanone, and forskolin; diterpenes, including but not limited to, casbene, eleutherobin, paclitaxel, prostratin, and pseudopterosin; triterpenes, including but not limited to, arbrusideE, bruceantin, testosterone, progesterone, cortisone, digitoxin. Isoprenoids also include, but are not limited to, carotenoids such as lycopene, α- and β-carotene, α- and β-cryptoxanthin, bixin, zeaxanthin, astaxanthin, and lutein. Isoprenoids also include, but are not limited to, triterpenes, steroid compounds, and compounds that are composed of isoprenoids modified by other chemical groups, such as mixed terpene-alkaloids, menaquinones (e.g., vitamin K-2), and coenzyme Q-10.

In some embodiments, a subject genetically modified host cell is cultured in a suitable medium (e.g., Luria-Bertoni broth, optionally supplemented with one or more additional agents, such as an inducer (e.g., where one or more enzyme-encoding nucleotide sequences (e.g., a nucleotide sequence encoding MK, a mevalonate pathway enzyme(s) other than MK, a prenyltransferase, a terpene synthase) is under the control of an inducible promoter), etc.); and the culture medium is overlaid with an organic solvent, e.g. dodecane, forming an organic layer. The isoprenoid compound produced by the genetically modified host cell partitions into the organic layer, from which it can be purified. In some embodiments, where the isoprenoid-modifying enzyme-encoding nucleotide sequence is operably linked to an inducible promoter, an inducer is added to the culture medium; and, after a suitable time, the isoprenoid compound is isolated from the organic layer overlaid on the culture medium.

In some embodiments, the isoprenoid compound produced by a genetically modified host cell will be separated from other products which may be present in the organic layer. Separation of the isoprenoid compound from other products that may be present in the organic layer is readily achieved using, e.g., standard chromatographic techniques.

In some embodiments, an isoprenoid compound synthesized by a subject method is further chemically modified in a cell-free reaction. For example, in some embodiments, artemisinic acid is isolated from culture medium and/or a cell lysate, and the artemisinic acid is further chemically modified in a cell-free reaction to generate artemisinin.

In some embodiments, the isoprenoid compound is pure, e.g., at least about 40% pure, at least about 50% pure, at least about 60% pure, at least about 70% pure, at least about 80% pure, at least about 90% pure, at least about 95% pure, at least about 98%, or more than 98% pure, where "pure" in the context of an isoprenoid compound refers to an isoprenoid compound that is free from other isoprenoid compounds, macromolecules, contaminants, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Generating Expression Plasmids Encoding Mevalonate Pathway Enzymes

Expression plasmid pMevT was generated by inserting the MevT operon into the pBAD33 vector. The MevT operon encodes the set of MEV pathway enzymes that together transform the ubiquitous precursor acetyl-CoA to (R)-mevalonate, namely acetoacetyl-CoA thiolase, HMG-CoA synthase, and HMG-CoA reductase. The MevT operon was generated by PCR amplifying from *Escherichia coli* genomic DNA the coding sequence of the atoB gene (GenBank accession number NC_000913 REGION: 2324131 . . . 2325315) (encodes an acetoacetyl-CoA thiolase), from *Saccharomyces cerevisiae* genomic DNA the coding sequence of the ERG13 gene (GenBank accession number X96617, REGION: 220 . . . 1695) (encodes a HMG-CoA synthase), and from *Saccharomyces cerevisiae* genomic DNA a segment of the coding region of the HMG1 gene (GenBank accession number M22002, REGION: 1660 . . . 3165) (encodes a truncated HMG-CoA reductase (tHMGR)). The upstream PCR primer used for the amplification of the HMG1 gene fragment included an artificial start codon. The amplified fragments were spliced together using overlap extensions (SOEing), during which process ribosome binding sites were introduced after the atoB and the ERG13 coding sequences. After the addition of 3' A overhangs, the MevT operon was ligated into the TA cloning vector pCR4 (Invitrogen, Carlsbad, Calif.). The MevT operon was subsequently ligated into the XmaI PstI restriction site of vector pBAD33 (Guzman et al. (1995) *J. Bacteriol.* 177(14): 4121-4130). To place the operon under the control of the $P_{Lac}$ promoter, the araC-$P_{BAD}$ NsiI-XmaI fragment of pBAD33 was replaced with the NsiI-XmaI fragment of pBBR1MCS, yielding expression plasmid pMevT (see U.S. Pat. No. 7,192,751).

Expression plasmid pAM36-MevT66 was generated by inserting the MevT66 operon into the pAM36 vector. The pAM36 vector was generated by inserting an oligonucleotide cassette containing AscI-SfiI-AsiSI-XhoI-PacI-FsII-PmeI restriction sites into the pACYC184 vector (GenBank accession number XO6403), and by removing the tetramycin resistance conferring gene in pACYC184. The MevT66 operon was synthetically generated using SEQ ID NO: 1 as a template, which comprises the atoB gene from *Escherichia coli* (GenBank accession number NC_000913 REGION: 2324131 . . . 2325315), the ERG13 gene from *Saccharomyces cerevisiae* (GenBank accession number X96617, REGION: 220 . . . 1695), and a truncated version of the HMG1 gene from *Saccharomyces cerevisiae* (GenBank accession number M22002, REGION: 1777 . . . 3285), all three sequences being codon-optimized for expression in *Escherichia coli*. The synthetically generated MevT66 operon was flanked by a 5' EcoRI restriction site and a 3' Hind III restriction site, and could thus be cloned into compatible restriction sites of a cloning vector such as a standard pUC or pACYC origin vector. From this construct, the MevT66 operon was PCR amplified with flanking SfiI and AsiSI restriction sites, the amplified DNA fragment was digested to completion using SfiI and AsiSI restriction enzymes, the reaction mixture was resolved by gel, electrophoresis, the approximately 4.2 kb DNA fragment was gel extracted using a gel purification kit (Qiagen, Valencia, Calif.), and the isolated DNA fragment was ligated into the SfiI AsiSI restriction site of the pAM36 vector, yielding expression plasmid pAM36-MevT66.

Expression plasmid pAM25 was generated by inserting the MevT66 operon into the pAM29 vector. The pAM29 vector was created by assembling the p15A origin of replication and kanamycin resistance conferring gene from pZS24-MCS1 (Lutz and Bujard (1997) *Nucl Acids Res.* 25:1203-1210) with an oligonucleotide-generated lacUV5 promoter. The nucleotide sequence of pAM29 is given as SEQ ID NO: 2. The DNA synthesis construct comprising the MevT66 operon (see description for pAM36-MevT66 above) was digested to completion using EcoRI and Hind III restriction enzymes, the reaction mixture was resolved by gel electrophoresis, the approximately 4.2 kb DNA fragment was gel extracted, and the isolated DNA fragment was ligated into the EcoRI HindIII restriction site of pAM29, yielding expression plasmid pAM25.

Expression plasmid pMevB-Cm was generated by inserting the MevB operon into the pBBR1MCS-1 vector. The MevB operon encodes the set of enzymes that together convert (R)-mevalonate to IPP, namely mevalonate kinase, phosphomevalonate kinase, and mevalonate pyrophosphate decarboxylase. The MevB operon was generated by PCR amplifying from *Saccharomyces cerevisiae* genomic DNA the coding sequences of the ERG12 gene (GenBank accession number X55875, REGION: 580 . . . 1911) (encodes a mevalonate kinase), the ERG8 gene (GenBank accession number Z49939, REGION: 3363 . . . 4718) (encodes a phosphomevalonate kinase), and the MVD1 gene (GenBank accession number X97557, REGION: 544 . . . 1734) (encodes a mevalonate pyrophosphate decarboxylase), and by splicing the PCR fragments together using overlap extensions (SOEing). By choosing appropriate primer sequences, the stop codons of ERG12 and ERG8 were changed from TAA to TAG during amplification to introduce ribosome binding sites. After the addition of 3' A overhangs, the MevB operon was ligated into the TA cloning vector pCR4 (Invitrogen, Carlsbad, Calif.). The MevB operon was excised by digesting the cloning construct to completion using PstI restriction enzyme, resolving the reaction mixture by gel electrophoresis, gel extracting the approximately 4.2 kb DNA fragment, and ligating the isolated DNA fragment into the PstI restriction site of vector pBBR1MCS-1 (Kovach et al., *Gene* 166(1): 175-176 (1995)), yielding expression plasmid pMevB-Cm.

Expression plasmid pMBI was generated by inserting the MBI operon into the pBBR1MCS-3 vector. In addition to the enzymes of the MevB operon, the MBI operon also encodes an isopentenyl pyrophosphatase isomerase, which catalyzes the conversion of IPP to DMAPP. The MBI operon was generated by PCR amplifying from *Escherichia coli* genomic DNA the coding sequence of the idi gene (GenBank accession number AF119715) using primers that contained an XmaI restriction site at their 5' ends, digesting the amplified DNA fragment to completion using XmaI restriction enzyme, resolving the reaction mixture by gel electrophoresis, gel extracting the approximately 0.5 kb fragment, and ligating the isolated DNA fragment into the XmaI restriction site of expression plasmid pMevB-Cm, thereby placing idi at the 3' end of the MevB operon. The MBI operon was subcloned into the SalI SacI restriction site of vector pBBR1MCS-3 (Kovach et al., *Gene* 166(1): 175-176 (1995)), yielding expression plasmid pMBI (see U.S. Pat. No. 7,192,751).

Expression plasmid pMBIS was generated by inserting the ispA gene into pMBI. The ispA gene encodes a farnesyl pyrophosphate synthase, which catalyzes the condensation of two molecules of IPP with one molecule of DMAPP to make farnesyl pyrophosphate (FPP). The coding sequence of the ispA gene (GenBank accession number D00694, REGION: 484 . . . 1383) was PCR amplified from *Escherichia coli* genomic DNA using a forward primer with a SacII restriction site and a reverse primer with a SacI restriction site. The amplified PCR product was digested to completion using SacII and SacI restriction enzymes, the reaction mixture was resolved by gel electrophoresis, and the approximately 0.9 kb DNA fragment was gel extracted, and the isolated DNA fragment was ligated into the SacII SacI restriction site of pMBI, thereby placing the ispA gene 3' of idi and the MevB operon, and yielding expression plasmid pMBIS (see U.S. Pat. No. 7,192,751).

Expression plasmid pAM47 was generated by inserting the MBIS operon into the pAM37 vector. Vector pAM37 was generated by assembling the p15A origin of replication and the chloramphenicol resistance conferring gene from vector pZA31luc (Lutz and Bujard (1997) *Nucl. Acids Res.* 25:1203-1210) with a strong constitutive promoter synthetically generated by linking oligonucleotides. The MBIS operon was PCR-amplified from pMBIS using primers 9-38A (SEQ ID NO: 7) and 9-38B (SEQ ID NO: 8), the approximately 5.5 kb PCR product was purified and digested to completion using ApaI and MluI restriction enzymes, and the DNA fragment was ligated into the ApaI MluI restriction enzyme site of pAM37, yielding expression plasmid pAM47.

Figure 3:
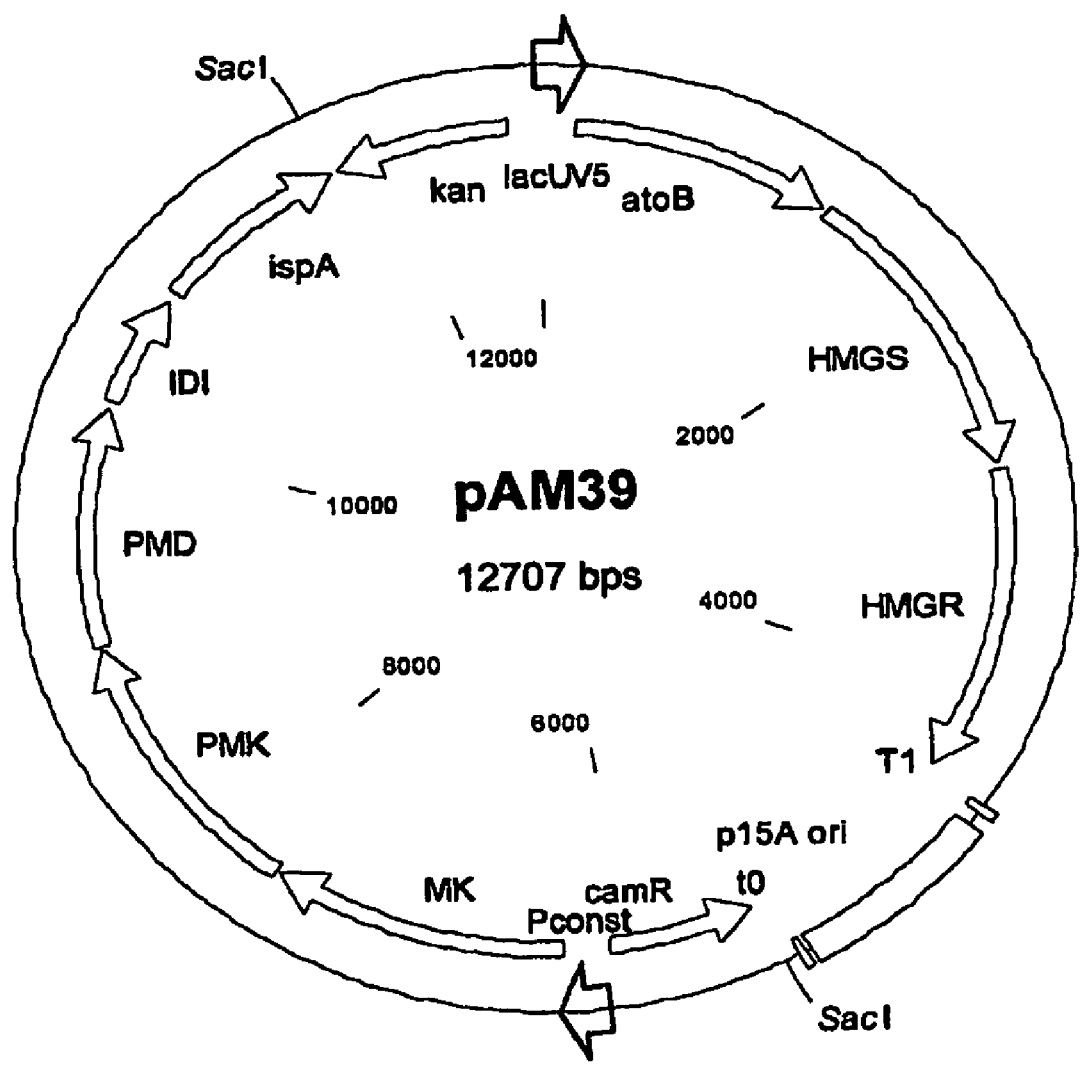
FIG. 3 is a map of expression plasmid pAM39.
Figure 4:
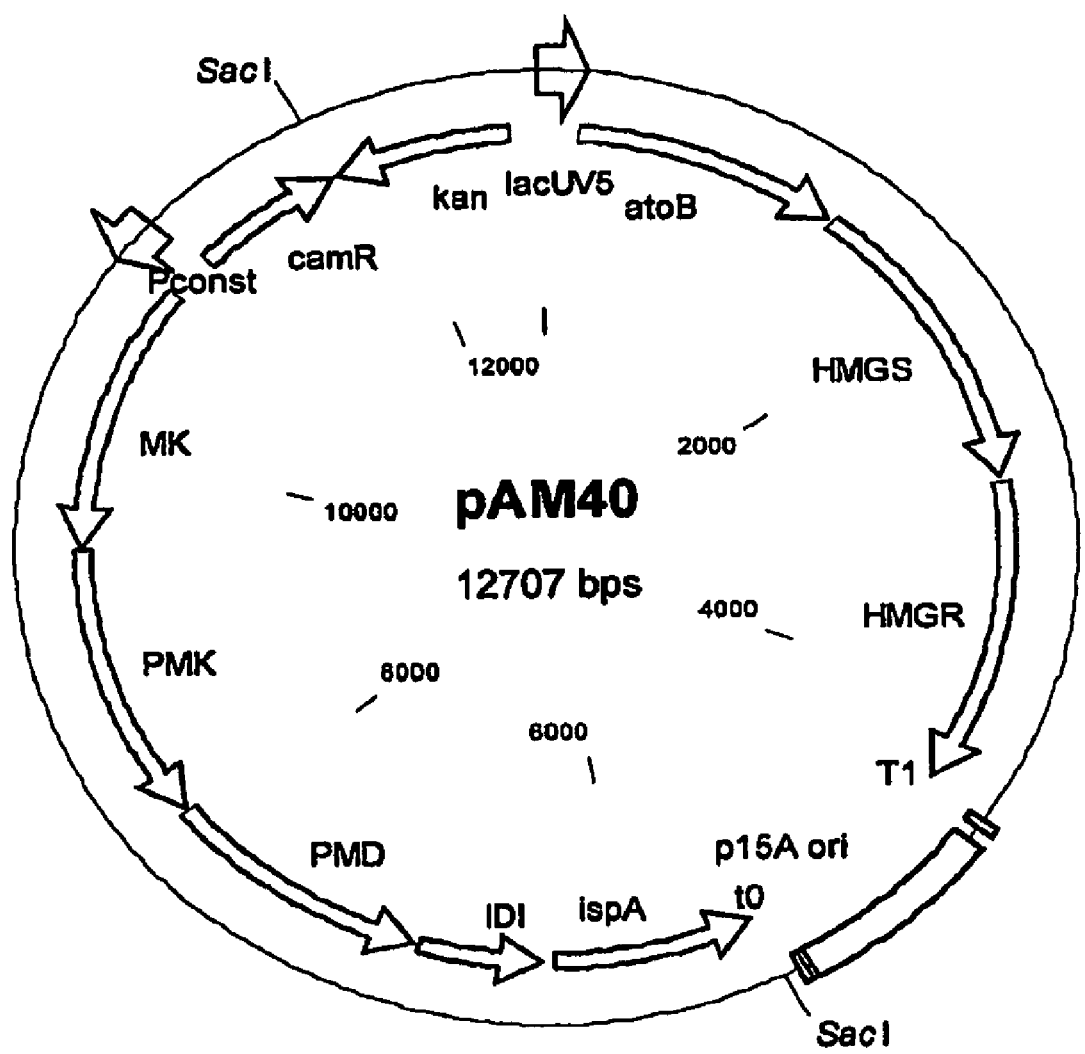
FIG. 4 is a map of expression plasmid pAM40.

Expression plasmids pAM39 and pAM40 were generated by combining expression plasmids pAM47 and pAM25. Expression plasmids pAM47 and pAM25 were digested using Sad restriction enzyme, and ligated to each other in two orientations, yielding expression plasmids pAM39 and pAM40. The nucleotide sequences of expression plasmids pAM39 and pAM40 are given as SEQ ID NO: 3 and SEQ ID NO: 4, respectively, and plasmid maps are shown in FIGS. 3 and 4, respectively.

Figure 5:
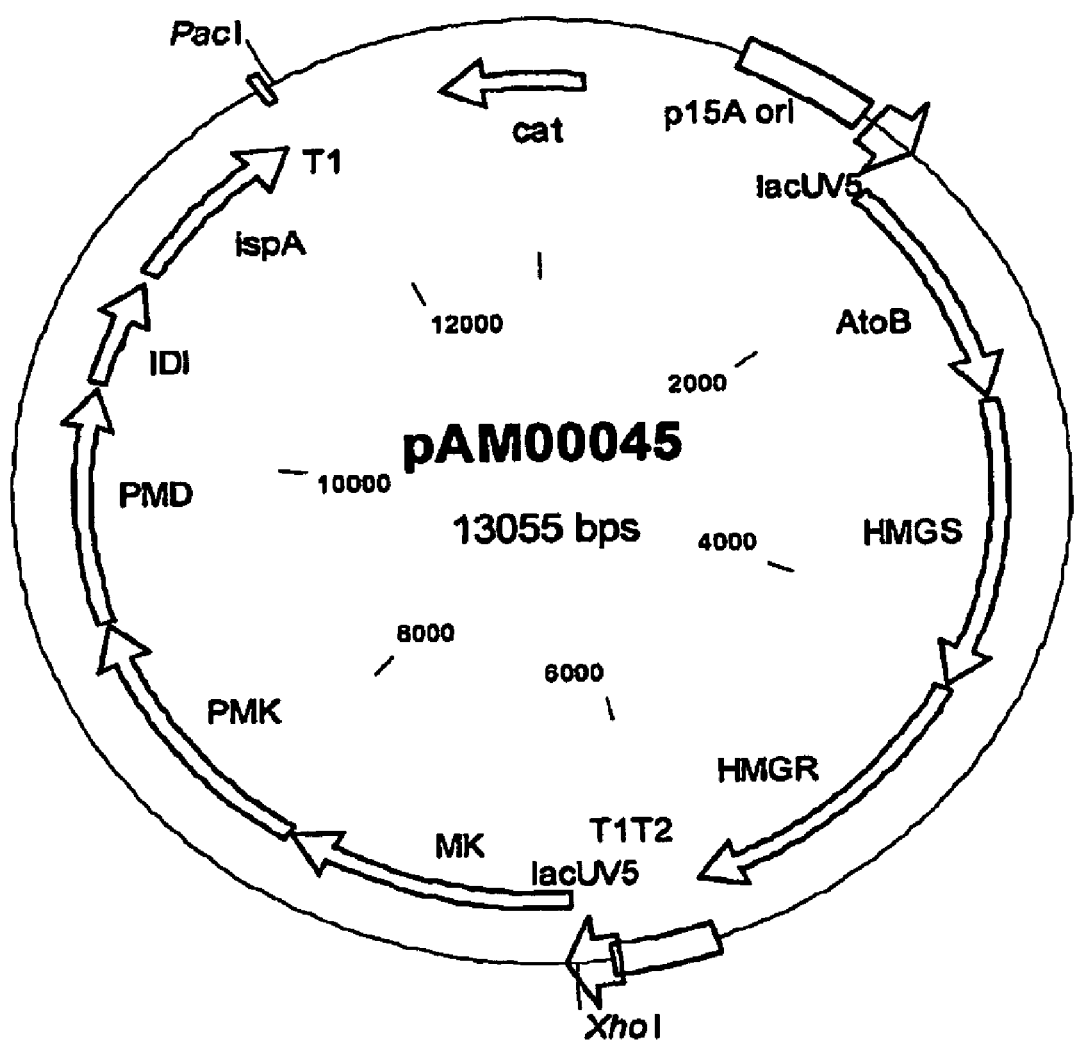
FIG. 5 is a map of expression plasmid pAM45.

Expression plasmid pAM45 was generated by inserting the MBIS operon into pAM36-MevT66 and adding lacUV5 promoters in front of the MBIS and MevT66 operons. The MBIS operon was PCR amplified from pMBIS using primers comprising a 5' XhoI restriction site and a 3' Pad restriction site, the amplified PCR product was digested to completion using XhoI and Pad restriction enzymes, the reaction mixture was resolved by gel electrophoresis, the approximately 5.4 kb DNA fragment was gel extracted, and the isolated DNA fragment was ligated into the XhoI Pad restriction site of pAM36-MevT66, yielding expression plasmid pAM43. A DNA fragment comprising a nucleotide sequence encoding the lacUV5 promoter was synthesized from oligonucleotides, and ligated into the AscI SfiI and AsiSI XhoI restriction sites of pAM43, yielding expression plasmid pAM45. The nucleotide sequence of pAM45 is given as SEQ ID NO: 5 and a plasmid map in FIG. 5.

Expression plasmid pAM29-MK was generated by inserting a nucleotide sequence encoding a mevalonate kinase ("MK") into the pAM29 vector. A nucleotide sequence encoding a mevalonate kinase was PCR-amplified from pMBIS using primers MK-SR (SEQ ID NO: 9) and MK-HR (SEQ ID NO: 10). The PCR product was purified, digested to completion using SalI and HindIII restriction enzymes, and ligated into the SalI HindIII restriction enzyme site of pAM29, yielding expression plasmid pAM29-MK.

Expression plasmid pAM29-PMK was generated by inserting a nucleotide sequence encoding a phosphomevalonate kinase ("PMK") into the pAM29 vector. A nucleotide sequence encoding a phosphomevalonate kinase was PCR-amplified from pMBIS using primers PMK-SR (SEQ ID NO: 11) and PMK-HR (SEQ ID NO: 12). The PCR product was purified, digested to completion using SalI and HindIII restriction enzymes, and ligated into the SalI HindIII restriction enzyme site of pAM29, yielding expression plasmid pAM29-PMK.

Expression plasmid pAM29-MPD was generated by inserting a nucleotide sequence encoding a mevalonate pyrophosphate decarboxylase ("MPD") into the pAM29 vector. A nucleotide sequence encoding a mevalonate pyrophosphate decarboxylase was PCR-amplified from pMBIS using primers MPD-ER (SEQ ID NO: 13) and MPD-SR (SEQ ID NO: 14). The PCR product was purified, digested to completion using SalI and HindIII restriction enzymes, and ligated into the EcoRI SalI restriction enzyme site of pAM29, yielding expression plasmid pAM29-MPD.

Expression plasmid pAM29-idi was generated by inserting a nucleotide sequence encoding an isopentenyl pyrophosphate isomerase ("idi") into the pAM29 vector. A nucleotide sequence encoding an isopentenyl pyrophosphate isomerase was PCR-amplified from pMBIS using primers idi-EF (SEQ ID NO: 15) and idi-SR (SEQ ID NO: 16). The PCR product was purified, digested to completion using SalI and HindIII restriction enzymes, and ligated into the EcoRI SalI restriction enzyme site of pAM29, yielding expression plasmid pAM29-idi.

Expression plasmid pAM29-ispA was generated by inserting a nucleotide sequence encoding a farnesyl pyrophosphate synthase ("ispA") into the pAM29 vector. A nucleotide sequence encoding a farnesyl pyrophosphate synthase was PCR-amplified from pMBIS using primers ispA-EF (SEQ ID NO: 17) and ispA-SR (SEQ ID NO: 18). The PCR product was purified, digested to completion using SalI and HindIII restriction enzymes, and ligated into the EcoRI SalI restriction enzyme site of pAM29, yielding expression plasmid pAM29-ispA.

Example 2

Generation of Expression Plasmids that Encode Enzymes that Convert FPP

Figure 6:
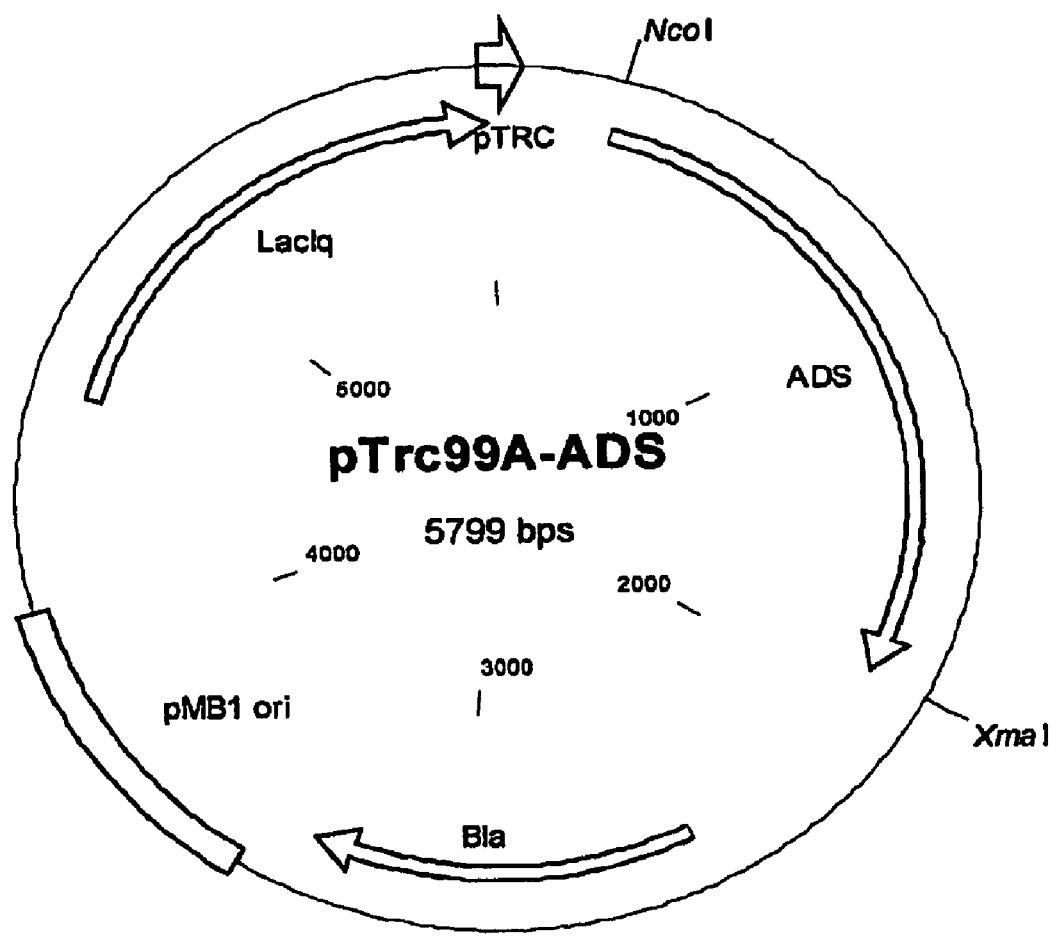
FIG. 6 is a map of expression plasmid pTrc99A-ADS.

Expression plasmid pTrc99A-ADS was generated by inserting a nucleotide sequence encoding an amorpha-4,11-diene, synthase ("ADS") into vector pTrc99A. The amorpha-4,11-diene synthase sequence was generated synthetically, so that upon translation the amino acid sequence would be identical to that described by Merke et al. (2000) Ach, Biochem. Biophys. 381:173-180, so that the nucleotide sequence encoding the amorpha-4,11-diene synthase was optimized for expression in Escherichia coli, and so that the nucleotide sequence was flanked by a 5' NcoI and a 3' XmaI restriction enzyme site (see U.S. Pat. No. 7,192,751). The nucleotide sequence was digested to completion using NcoI and XmaI restriction enzymes, the reaction mixture was resolved by gel electrophoresis, the approximately 1.6 kb DNA fragment was gel-extracted, and the isolated DNA fragment was inserted into the NcoI XmaI restriction enzyme site of the pTrc99A vector (Amman et al. (1985) Gene 40:183-190), yielding expression plasmid pTrc99A-ADS (see FIG. 6 for a plasmid map).

Figure 7:
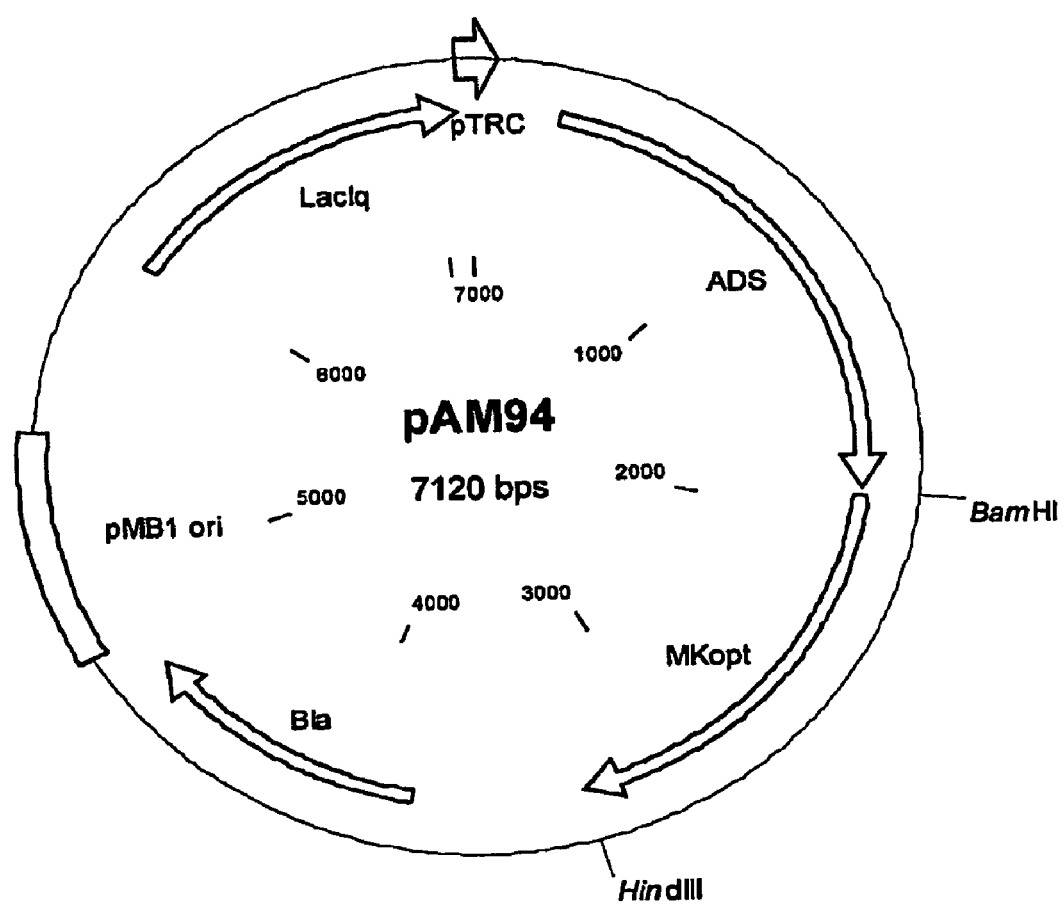
FIG. 7 is a map of expression plasmid pAM94.

Expression plasmid pAM94 was generated by inserting a nucleotide sequence encoding the *Saccharomyces cerevisiae* melavonate kinase (MK), codon-optimized for expression in *Escherichia coli*, into vector pTrc99A. The codon-optimized nucleotide sequence was PCR amplified from pMBISopt using primers 9-153C (SEQ ID NO: 19) and 9-153D (SEQ ID NO: 20). The PCR product was digested to completion using BamHI and HindIII restriction enzymes, and ligated into the BamHI HindIII restriction site of expression plasmid pTrc99A-ADS, yielding expression plasmid pAM94. The nucleotide sequence of pAM94 is given is SEQ ID NO: 6 and a plasmid map in FIG. 7.

Example 3

Generation of *Escherichia coli* Host Strains

As detailed in Table 1, the host strains were created by transforming chemically competent *Escherichia coli* DH1 parent cells with one or more expression plasmids of Examples 1 and 2.

TABLE 1

*Escherichia coli* host strains

| Host Strain | Expression Plasmids | Antibiotic Selection |
| --- | --- | --- |
| B32 | pMevT | 100 ug/mL carbenicillin |
|  | pMBIS | 35 ug/mL chloramphenicol |
|  | pTrc-ADS | 10 ug/mL tetracycline |
| B59 | pAM39 | 100 µg/ml carbenicillin |
|  | pTrc-ADS | 35 µg/ml chloramphenicol |
| B60 | pAM40 |  |
|  | pTrc-ADS |  |
| B125 | pAM45 |  |
|  | pTrc-ADS |  |
| 1 | pMBIS | 100 µg/mL ampicillin |
|  | pTrc-ADS | 50 µg/mL kanamycin |
|  | pAM29 | 5 µg/mL tetracycline |
| 2 | pMBIS |  |
|  | pTrc-ADS |  |
|  | pAM29-MK |  |
| 3 | pMBIS |  |
|  | pTrc-ADS |  |
|  | pAM29-PMK |  |
| 4 | pMBIS |  |
|  | pTrc-ADS |  |
|  | pAM29-MPD |  |
| 5 | pMBIS |  |
|  | pTrc-ADS |  |
|  | pAM29-idi |  |
| 6 | pMBIS |  |
|  | pTrc-ADS |  |
|  | pAM29-ispA |  |
| B177 | pMevT | 100 µg/mL carbenicillin |
|  | pMBIS | 35 µg/mL chloramphenicol |
|  | pAM94 | 10 µg/mL tetracycline |

Host cell transformants were selected on Luria Bertoni (LB) agar containing antibiotics as detailed in Table 1. Single colonies of strains B59 and B60 were transferred from LB agar to culture tubes containing 5 mL of LB liquid medium and antibiotics. Single colonies of strains B32, B125, 1 through 6, and B177 were transferred from LB agar to culture tubes containing 5 mL of M9-MOPS (Table 2) containing 8-10 g/L of D-glucose. The cultures were incubated at 30° C. on a rotary shaker at 250 rpm for 30 hours, at which point cell growth was arrested by chilling the cultures on ice. The cells were stored at −80° C. in cryo-vials in 1 mL stock aliquots made up of 400 uL sterile 50% glycerol and 600 µL liquid culture.

Example 4

Production of Amorpha-4,11-Diene in *Escherichia coli* Host Strains

Production cultures of host strains B32, B59, B60, and B125 were established by adding a stock aliquot of each strain to separate 250 mL flasks containing 40 mL of medium (TB-1% glycerol medium for strains B32, B59, and B60; M9-MOPS medium containing 20 g/L D-glucose for strains B32 and B125) and antibiotics as detailed in Table 1. The cultures were incubated at 30° C. on a rotary shaker at 250 rpm until they reached an $OD_{600}$ of approximately 0.2 to 0.3, at which point the production of amorpha-4,11-diene in the host cells was induced by adding 40 uL of 1 M IPTG to the culture medium. At the time of induction, the cultures were overlain with 8 mL of dodecane to capture the amorpha-4,11-diene. Samples were taken at various time points by adding 10 uL of the dodecane layer to 990 μL ethyl acetate in a clean glass GC vial and vortexing for 30 seconds.

The ethyl acetate culture extracts were analyzed on a Hewlett-Packard 6890 gas chromatograph/mass spectrometer (GC/MS) as described in Martin et al. ((2001) *Biotechnol. Bioeng.* 75:497-503), by scanning for the molecular ion (204 m/z) and the 189 m/z ion. To expedite run times, the temperature program and column matrix was modified to achieve optimal peak resolution and the shortest overall runtime. Compounds in a 1 uL sample were separated using a DB-XLB column (available from Agilent Technologies, Inc., Palo Alto, Calif.) and helium carrier gas. The oven cycle for each sample was either 80° C. hold for 2 minutes, increasing temperature at 30° C./minute to a temperature of 160° C., increasing temperature at 3° C./minute to a temperature of 170° C., increasing temperature at 50° C./minute to 300° C., and a hold at 300° C. for 2 minutes (GC protocol 1), or 100° C. hold for 0.75 minutes, increasing temperature at 60° C./minute to a temperature of 300° C., and a hold at 300° C. for 0.5 minutes (GC protocol 2). The resolved samples were analyzed by a Hewlett-Packard model 5973 mass selective detector. Previous mass spectra demonstrated that the amorpha-4,11-diene synthase product was amorpha-4,11-diene, and that amorpha-4,11-diene had a retention time of 7.9 minutes using GC protocol 1, and 3.7 minutes using GC protocol 2. Beta- or trans-caryophyllene (Sigma-Aldrich, St. Louis, Mo.) was used as an internal standard for quantitation. Amorpha-4,11-diene titer was calculated based upon a quantitative calibration curve of purified amorpha-4,11-diene in caryophyllene-spiked ethyl acetate.

Figure 8A:
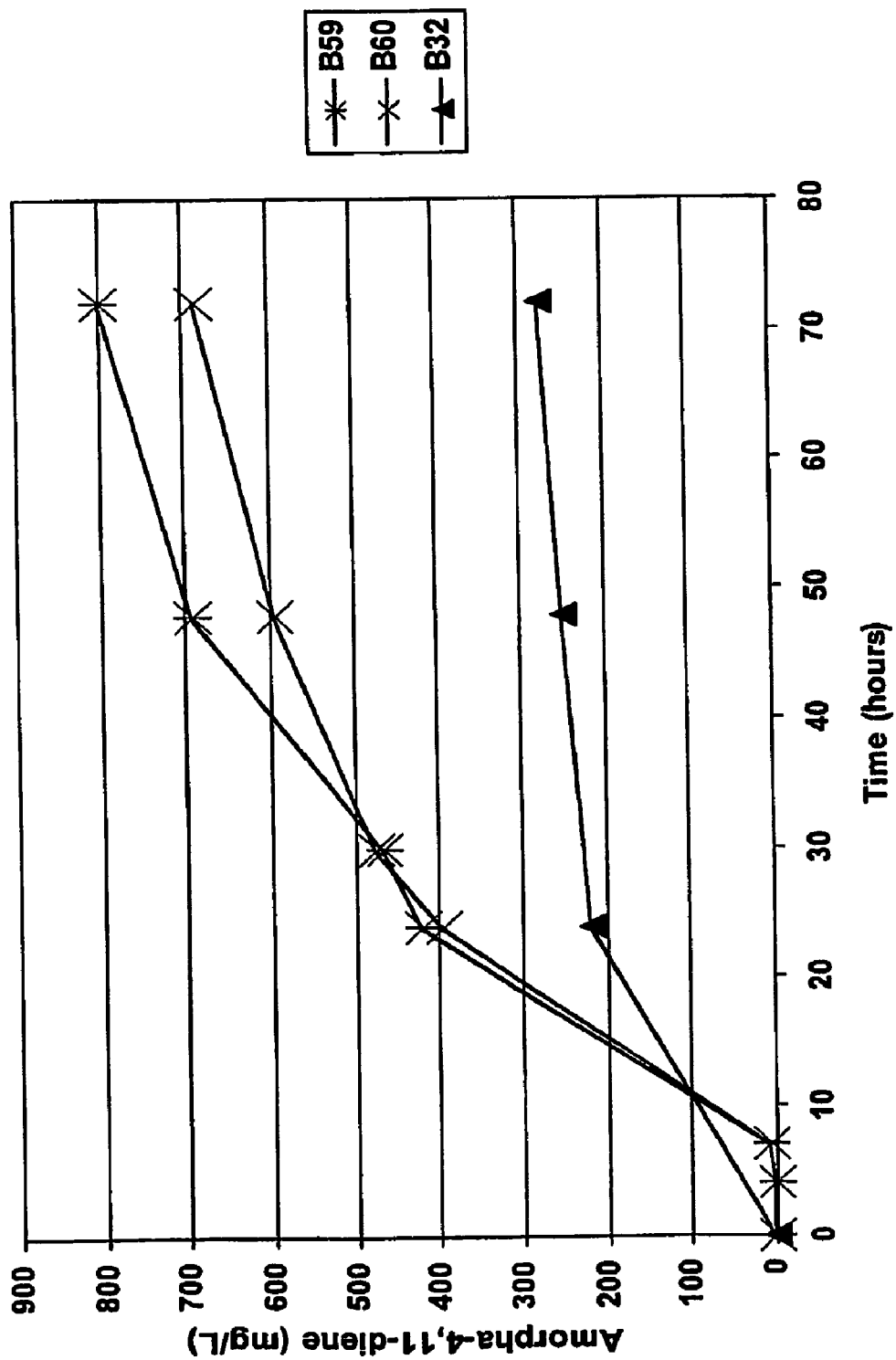
FIGS. 8A and 8B show production of amorpha-4,11-diene in host strains in which the MBIS operon is expressed from a higher copy number plasmid and a stronger promoter.
Figure 8B:
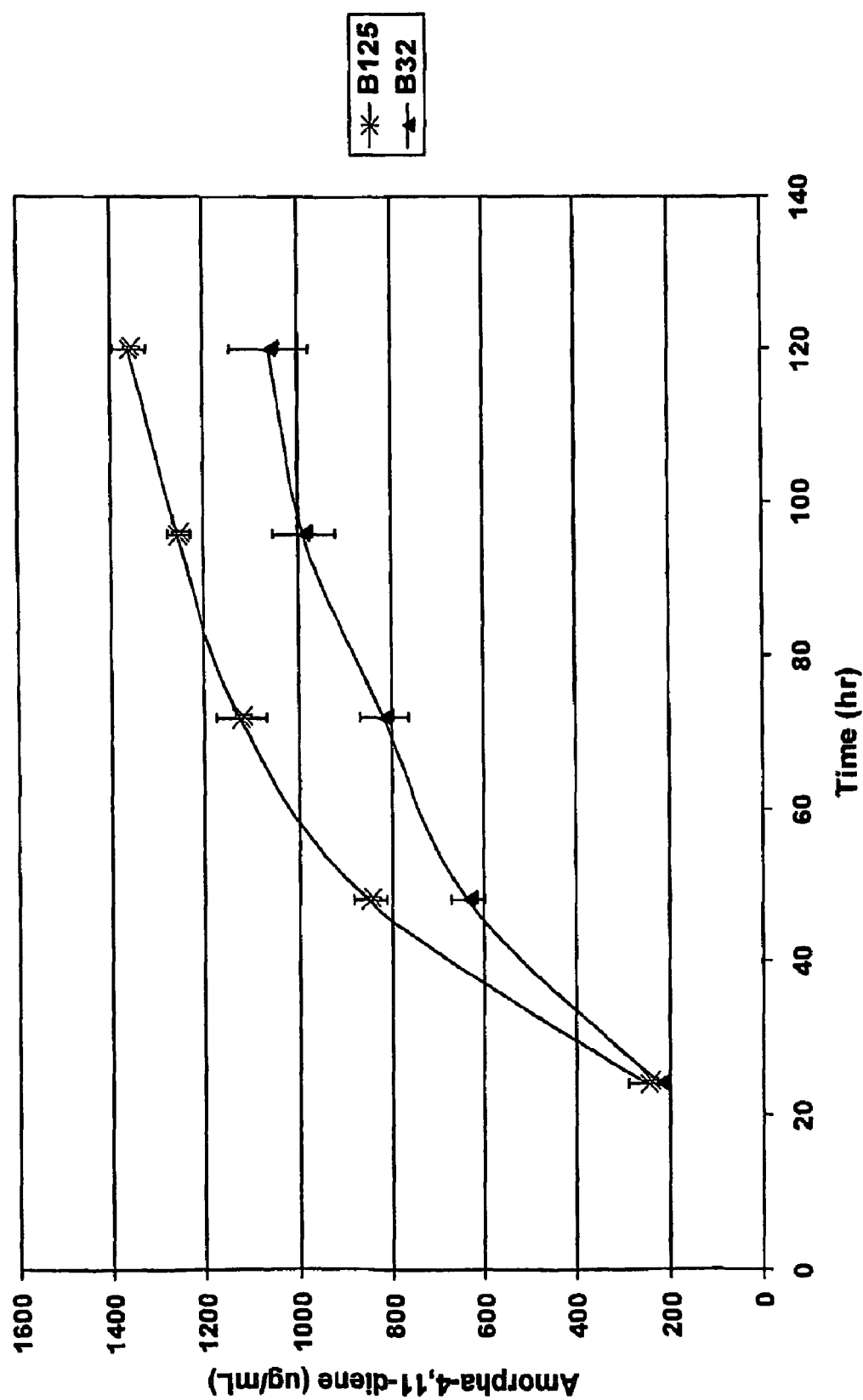

FIGS. 8A and 8B show that host strains in which the MBIS operon is expressed from a higher copy number plasmid and a stronger promoter produce higher levels of amorpha-4,11-diene.

Example 5

Production of Amorpha-4,11-Diene in *Escherichia coli* Host Strains that Harbor a Plurality of Copies of Nucleotide Sequences Encoding Mevalonate Kinase Production cultures of host strains 1 through 6 were established by adding a stock aliquot of each strain to separate 250 mL flasks containing 50 mL of M9-MOPS medium containing 10 g/L D-glucose and antibiotics as detailed in Table 1 at a starting $OD_{600}$ of approximately 0.5. The cultures were incubated at 30° C. on a rotary shaker at 250 rpm until they reached an $OD_{600}$ of approximately 0.2 to 0.3, at which point the production of amorpha-4,11-diene in the host cells was induced by adding 40 μL of 1 M IPTG to the culture medium. At the time of induction, the cultures were also supplemented with 20 mM of D,L-mevalonate and were overlain with 8 ml, of dodecane to capture the amorpha-4,11-diene. Samples were taken at various time points by transferring 10 μL of the dodecane overlay to 990 μL of ethyl acetate, and analyzed using GC protocol 1 as described in Example 4.

Figure 9:
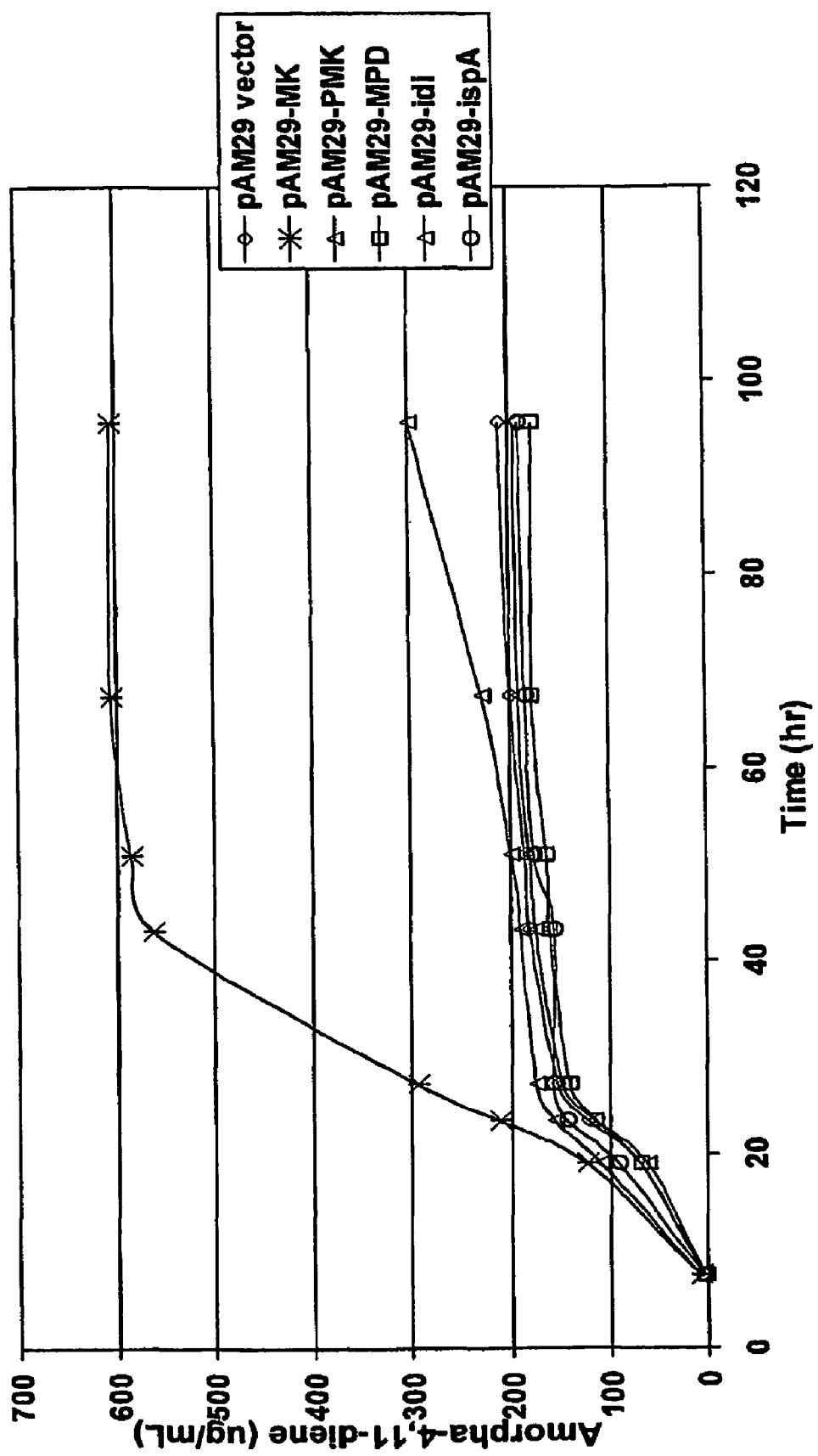
FIG. 9 shows amorpha-4,11-diene production by host strains in which the gene dosage of mevalonate kinase is increased.

FIG. 9 shows that host strains in which the gene dosage of mevalonate kinase is increased produce higher levels of amorpha-4,11-diene.

Example 6

Production of amorpha-4,11-diene in *Escherichia coli* host strains that harbor a plurality of copies of nucleotide sequences encoding mevalonate kinase Host strains B32 and B177 were cultured and amorpha-4,11-diene production analyzed as described in Example 4.

Figure 10:
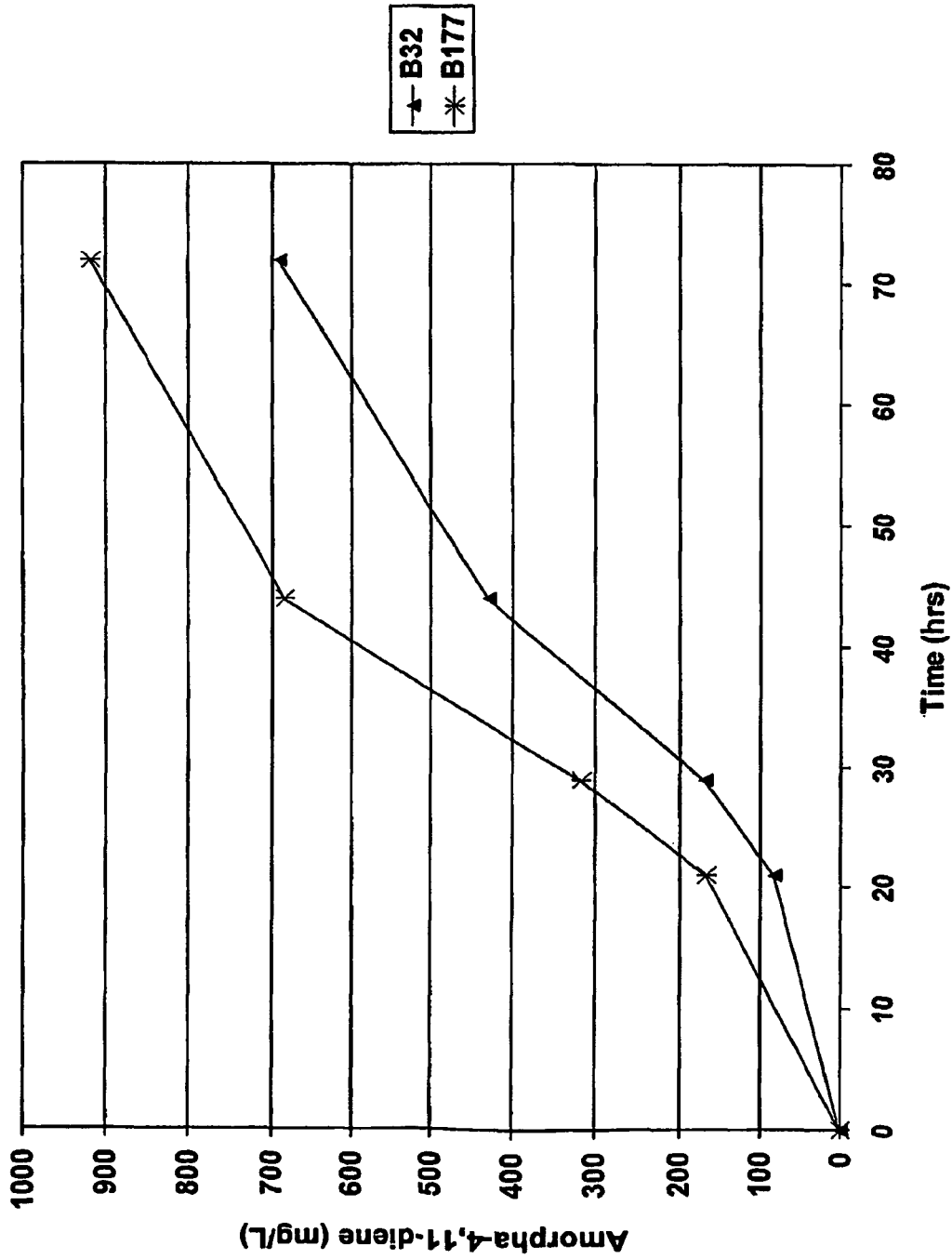
FIG. 10 shows amorpha-4,11-diene production in host strains in which the gene dosage and expression of mevalonate kinase are increased.

FIG. 10 shows that host strains in which the gene dosage and expression of mevalonate kinase is increased produce higher levels of amorpha-4,11-diene.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A host cell capable of producing an isoprenoid and comprising:
   a coding region encoding a mevalonate kinase (MK);
   a nucleic acid comprising a nucleotide sequence encoding one or more mevalonate pathway enzyme other than mevalonate kinase selected from a phosphomevalonate kinase (PMK), and a mevalonate pyrophosphate decarboxylase (MPD); and
   a heterologous nucleotide sequence encoding a terpene synthase;
   wherein the level of MK produced in said host cell is at least 50% higher than the level of at least one of PMK and MPD.

2. A host cell according to claim 1, wherein the MK coding region is under the control of a first promoter and the nucleotide sequence encoding one or more mevalonate pathway enzyme other than mevalonate kinase is under the control of a second promoter wherein the second promoter is weaker than the first promoter.

3. A host cell according to claim 2, wherein the first promoter is a constitutively active promoter.

4. A host cell according to claim 2, wherein the first promoter is an inducible promoter.

5. A host cell according to claim 2, wherein the first promoter is stronger than a native *Escherichia coli* Lac promoter or a PLac promoter.

6. A host cell according to claim 2, wherein the first promoter is a lacUV5 promoter or a trc promoter.

7. A host cell according to claim 1, wherein said cell comprises at least two coding regions comprising nucleotide sequences encoding a mevalonate kinase.

8. A host cell according to claim 7, wherein the copy number of coding regions comprising nucleotide sequences encoding a mevalonate kinase is higher than the copy number of coding regions encoding one or more mevalonate pathway enzymes other than mevalonate kinase.

9. A host cell according to claim 1, further comprising a nucleotide sequence encoding an isopentenyl pyrophosphate (IPP) isomerase.

10. A host cell according to claim 1, further comprising a heterologous nucleic acid comprising a nucleotide sequence encoding a prenyltransferase selected from a farnesyl diphosphate synthase, a geranyl diphosphate synthase, and a geranylgeranyl diphosphate synthase.

11. A host cell according to claim 1, wherein the isoprenoid is a diterpene, a triterpene, or a sesquiterpene.

12. A host cell according to claim 1, wherein one or more of the nucleotide sequences encoding the mevalonate kinase or mevalonate pathway enzymes is codon-optimized for expression in said host cell.

13. A host cell according to claim 1, wherein the terpene synthase is selected from an amorpha-4,11-diene synthase; a beta-caryophyllene synthase; a germacrene A synthase; a 8-epicedrol synthase; a valencene synthase; a (+)-delta-cadinene synthase; a germacrene C synthase; a (E)-beta-farnesene synthase; a casbene synthase; a vetispiradiene synthase; a 5-epi-aristolochene synthase; an aristolchene synthase alpha-humulene synthase; an (E,E)-alpha-farnesene synthase; a (−)-beta-pinene synthase; a gamma-terpinene synthase; a limonene cyclase; a linalool synthase; a 1,8-cineole synthase; a (+)-sabinene synthase; an E-alpha-bisabolene synthase; a (+)-bornyl diphosphate synthase; a levopimaradiene synthase; an abietadiene synthase; an isopimaradiene synthase; a (E)-gamma-bisabolene synthase; a taxadiene synthase; a copalyl pyrophosphate synthase; a kaurene synthase; a longifolene synthase; a gamma-humulene synthase; a Delta-selinene synthase; a beta-phellandrene synthase; a limonene synthase; a myrcene synthase; a terpinolene synthase; a (−)-camphene synthase; a (+)-3-carene synthase; a syn-copalyl diphosphate synthase; an alpha-terpineol synthase; a syn-pimara-7,15-diene synthase; an ent-sandaaracopimaradiene synthase; a stemer-13-ene synthase; a E-beta-ocimene; a S-linalool synthase; a geraniol synthase; a gamma-terpinene synthase; a linalool synthasel; a E-beta-ocimene synthase; an epi-cedrol synthase; an alpha-zingiberene synthase; a guaiadiene synthase; a cascarilladiene synthase; a cis-muuroladiene synthase; an aphidicolan-16b-ol synthase; an elizabethatriene synthase; a sandalol synthase; a patchoulol synthase; a zinzanol synthase; a cedrol synthase; a scareol synthase, copalol synthase; and a manool synthase.

14. A host cell according to claim 1, wherein the host cell is a prokaryotic cell.

15. A host cell according to claim 1, wherein the host cell is a eukaryotic cell.

16. An *Escherichia coli* host cell capable of producing an isoprenoid and comprising:
 a first expression plasmid comprising a nucleotide sequence encoding a mevalonate kinase;
 a second expression plasmid comprising a nucleotide sequence encoding one or more mevalonate pathway enzymes other than mevalonate kinase, wherein the copy number of the second expression plasmid is lower than that of the first expression plasmid; and
 a heterologous nucleotide sequence encoding a terpene synthase.

17. A host cell according to claim 14, wherein the host cell is a prokaryotic cell that does not synthesize an isopentenyl pyrophosphate (IPP) via an endogenous mevalonate pathway.

18. A host cell according to claim 1, wherein the host cell is genetically modified with one or more nucleic acids comprising nucleotide sequences encoding one or more of:
 a) an acetoacetyl-CoA thiolase;
 b) an enzyme that condenses acetoacetyl-CoA with acetyl-CoA to form hydroxymethylglutaryl- CoenzymeA (HMG-CoA); and
 c) an enzyme that converts HMG-CoA to mevalonate.

19. A host cell according to claim 18, wherein the enzyme that condenses acetoacetyl-CoA with acetyl-CoA to form HMG-CoA is HMG-CoA synthase.

20. A host cell according to claim 16, wherein the mevalonate pathway enzymes other than mevalonate kinase are selected from a phosphomevalonate kinase (PMK), and a mevalonate pyrophosphate decarboxylase (MPD).

21. A host cell according to claim 16, further comprising a nucleotide sequence encoding an isopentenyl pyrophosphate (IPP) isomerase.

22. A host cell according to claim 16, further comprising a heterologous nucleic acid comprising a nucleotide sequence encoding a prenyltransferase selected from a farnesyl diphosphate synthase, a geranyl diphosphate synthase, and a geranylgeranyl diphosphate synthase.

23. A host cell according to claim 16, wherein the isoprenoid is a diterpene, a triterpene, or a sesquiterpene.

24. A host cell according to claim 16, wherein one or more of the nucleotide sequences encoding the mevalonate kinase or mevalonate pathway enzymes is codon-optimized for expression in said host cell.

25. A host cell according to claim 16, wherein the terpene synthase is selected from an amorpha-4,11-diene synthase; a beta-caryophyllene synthase; a germacrene A synthase; a 8-epicedrol synthase; a valencene synthase; a (+)-delta-cadinene synthase; a germacrene C synthase; a (E)-beta-farnesene synthase; a casbene synthase; a vetispiradiene synthase; a 5-epi-aristolochene synthase; an aristolchene synthase alpha-humulene synthase; an (E,E)-alpha-farnesene synthase; a (−)-beta-pinene synthase; a gamma-terpinene synthase; a limonene cyclase; a linalool synthase; a 1,8-cineole synthase; a (+)-sabinene synthase; an E-alpha-bisabolene synthase; a (+)-bornyl diphosphate synthase; a levopimaradiene synthase; an abietadiene synthase; an isopimaradiene synthase; a (E)-gamma-bisabolene synthase; a taxadiene synthase; a copalyl pyrophosphate synthase; a kaurene synthase; a longifolene synthase; a gamma-humulene synthase; a Delta-selinene synthase; a beta-phellandrene synthase; a limonene synthase; a myrcene synthase; a terpinolene synthase; a (−)-camphene synthase; a (+)-3-carene synthase; a syn-copalyl diphosphate synthase; an alpha-terpineol synthase; a syn-pimara-7,15-diene synthase; an ent-sandaaracopimaradiene synthase; a stemer-13-ene synthase; a E-beta-ocimene; a S-linalool synthase; a geraniol synthase; a gamma-terpinene synthase; a linalool synthasel; a E-beta-ocimene synthase; an epi-cedrol synthase; an alpha-zingiberene synthase; a guaiadiene synthase; a cascarilladiene synthase; a cis-muuroladiene synthase; an aphidicolan-16b-ol synthase; an elizabethatriene synthase; a sandalol synthase; a patchoulol synthase; a zinzanol synthase; a cedrol synthase; a scareol synthase, copalol synthase; and a manool synthase.

26. A host cell according to claim 16, wherein the level of MK produced in said host cell is at least 50% higher than the level of at least one of the mevalonate pathway enzymes other than mevalonate kinase.

27. A host cell according to claim 18, wherein the enzyme that converts HMG-CoA to mevalonate is HMG-CoA reductase.

* * * * *

SEQUENCE LISTING

<160> NUMBER OF SEQ ID NOS: 22

<210> SEQ ID NO 1
<211> LENGTH: 4247
<212> TYPE: DNA
<213> ORGANISM: Artificial Sequence
<220> FEATURE:
<223> OTHER INFORMATION: recombinant vector

<400> SEQUENCE: 1
gaattcaaag gaggaaaata aaatgaagaa ctgtgtgatt gtttctgcgg tccgcacggc        60
gatcggcagc tttaacggct ctttagcgag cacctctgca atcgatctgg gtgcgacggt       120

```
cattaaggcc gccattgaac gcgccaaaat cgacagccag cacgttgatg aggtgatcat    180
gggcaatgtg ttacaagccg gcctgggtca aacccagcg cgtcaagcac tgttaaaatc    240
tggtctggcc gagaccgtgt gtggcttcac cgtcaataag gtttgcggct ctggcctgaa    300
gagcgtggcc ctggcagcac aagcgattca agccggtcag gcacaaagca tcgttgcggg    360
tggcatggag aacatgtctc tggcgccgta cttattagat gccaaagccc gcagcgttta    420
tcgcctgggc gatggtcagg tgtacgacgt catcttacgc gatggcttaa tgtgcgcgac    480
ccacggttac cacatgggta ttacggccga aacgtggcg aaagaatacg gcattacgcg    540
cgagatgcag gatgaattag cactgcactc tcagcgcaaa gcagcagccg cgatcgagtc    600
tggtgcgttt acggcggaaa tcgtgccagt taacgtggtc acgcgcaaga agacgttcgt    660
tttcagccag gacgagttcc cgaaggcaaa cagcaccgcg gaggccttag gtgccttacg    720
cccagccttt gacaaagcgg gcacggtcac cgccggtaat gcgagcggca tcaatgatgg    780
tgcagcggca ctggtcatca tggaagagag cgccgcatta gcagcgggtc tgaccccatt    840
agcgcgcatt aaatcttatg ccagcggcgg cgtcccacca gccctgatgg gcatgggtcc    900
ggtcccagcc acgcaaaaag ccctgcaatt agcgggcctg caactggccg acattgatct    960
gatcgaggcg aacgaggcgt ttgcagcgca gttcctggcg gtgggtaaga atctgggctt   1020
cgacagcgag aaagtcaatg tgaacggtgg cgcgattgcg ttaggccatc cgattggtgc   1080
aagcggcgca cgcatcttag tgacgttact gcacgccatg caggcacgcg acaagacctt   1140
aggcctggcg accttatgta ttggtggcgg tcaaggtatc gccatggtga tcgaacgcct   1200
gaactgaaga tctaggagga aagcaaaatg aaactgagca ccaagctgtg ctggtgtggc   1260
atcaagggtc gcctgcgccc acaaaagcag caacagctgc acaacacgaa cctgcaaatg   1320
accgagctga aaaagcagaa gacggccgag caaaagaccc gcccgcagaa cgttggcatc   1380
aagggcatcc agatttatat cccgacgcag tgtgtcaacc aatctgagct ggagaaattc   1440
gatggcgtca gccagggtaa gtacaccatc ggcctgggcc agaccaacat gagcttcgtg   1500
aacgaccgtg aggacatcta ttctatgagc ctgacggtgc tgtctaagct gatcaagagc   1560
tacaacatcg acacgaataa gatcggtcgt ctggaggtgg gtacggagac gctgattgac   1620
aagagcaaaa gcgtgaagtc tgtcttaatg cagctgttcg gcgagaacac ggatgtcgag   1680
ggtatcgaca ccctgaacgc gtgttacggc ggcaccaacg cactgttcaa tagcctgaac   1740
tggattgaga gcaacgcctg ggatggccgc gatgcgatcg tcgtgtgcgg cgatatcgcc   1800
atctatgaca agggtgcggc acgtccgacc ggcggtgcag gcaccgttgc gatgtggatt   1860
ggcccggacg caccaattgt cttcgattct gtccgcgcgt cttacatgga gcacgcctac   1920
gacttttaca gccggacttt cacgagcgaa tacccgtacg tggacggcca cttctctctg   1980
acctgctatg tgaaggcgct ggaccaggtt tataagtctt atagcaaaaa ggcgatttct   2040
aagggcctgg tcagcgaccc ggcaggcagc gacgccctga acgtgctgaa gtatttcgac   2100
tacaacgtgt tccatgtccc gacctgcaaa ttagtgacca aatcttatgg ccgcctgtta   2160
tataatgatt tccgtgccaa cccgcagctg ttcccggagg ttgacgccga gctggcgacg   2220
cgtgattacg acgagagcct gaccgacaag aacatcgaga agaccttcgt caacgtcgcg   2280
aagccgttcc acaaagagcg tgtggcccaa agcctgatcg tcccgaccaa cacgggcaac   2340
atgtataccg cgtctgtcta cgcggcattc gcgagcctgc tgaattacgt cggttctgac   2400
gacctgcagg gcaagcgcgt tggcctgttc agctacggta gcggcttagc ggccagcctg   2460
tatagctgca aaattgtcgg cgacgtccag cacatcatca aggagctgga catcaccaac   2520
```

```
aagctggcga agcgcatcac cgagacgccg aaagattacg aggcagcgat cgagttacgc    2580
gagaatgcgc atctgaagaa gaacttcaag ccgcaaggta gcatcgagca cctgcagagc    2640
ggcgtctact acctgacgaa cattgacgac aagttccgcc gttcttatga cgtcaaaaag    2700
taactagtag gaggaaaaca tcatggtgct gacgaacaaa accgtcatta gcggcagcaa    2760
ggtgaagtct ctgagcagcg cccaaagctc tagcagcggc ccgtctagca gcagcgagga    2820
ggacgacagc cgtgacattg agtctctgga caagaagatc cgcccgctgg aggagttaga    2880
ggccctgctg agcagcggca acaccaagca gctgaagaac aaggaagttg cagcgctggt    2940
gatccacggt aagctgccac tgtatgcgct ggaaaagaaa ctgggcgata cgacgcgtgc    3000
ggtcgcggtg cgtcgcaaag ccttaagcat cttagcggag gccccggtgt agccagcga    3060 ccgcctgccg tacaagaact acgactacga ccgcgtgttt ggcgcgtgct gcgagaatgt    3120
cattggctac atgccgttac cggttggtgt gatcggcccg ctggtcattg atggcacgag    3180
ctatcacatt ccaatggcga ccacggaagg ttgcttagtc gccagcgcca tgcgtggctg    3240
taaggcgatt aacgccggcg gtggcgcgac gaccgtgtta accaaggatg gtatgacgcg    3300
cggtccggtc gtccgcttcc caacgctgaa gcgcagcggc gcgtgtaaga tttggctgga    3360
ttctgaggag ggccaaaacg cgatcaagaa agccttcaac tctacgagcc gtttcgcgcg    3420
tttacagcat atccagacct gcctggccgg cgacctgctg ttcatgcgct tccgcaccac    3480
cacgggcgat gcgatgggca tgaacatgat cagcaagggc gtcgaatata gcctgaaaca    3540
aatggtggaa gaatatggct gggaggacat ggaggttgtc tctgtgagcg gcaactattg    3600
caccgacaag aagccggcag ccattaactg gattgagggt cgcggcaaaa gcgtcgtggc    3660
agaagcgacc atcccaggcg acgtggtccg taaggttctg aagagcgacg tcagcgccct    3720
ggttgagtta aatatcgcga aaaacctggt cggcagcgcg atggcgggca gcgtgggtgg    3780 cttaacgca catgcagcga atctggttac ggcggttttc ttagccttag gtcaggaccc    3840
agcccaaaat gtcgagagca gcaactgcat taccttaatg aaagaggttg acggtgacct    3900
gcgcatcagc gtttctatgc cgtctatcga ggtcggcacg atcggcggcg caccgttttt    3960
agaaccgcaa ggtgcgatgc tggatctgct gggcgtgcgc ggcccacatg caacggcccc    4020
aggcaccaat gcccgccaac tggcccgtat cgtggcctgc gcggttctgg cgggtgagct    4080
gagcctgtgc gccgcattag ccgcgggcca tttagttcaa tctcacatga cccacaaccg    4140
caagccggca gaaccaacca agccaaataa cctggacgca accgacatta accgtctgaa    4200
ggatggcagc gtcacgtgca ttaaaagctg agcatgctac taagctt    4247

<210> SEQ ID NO 2
<211> LENGTH: 2174
<212> TYPE: DNA
<213> ORGANISM: Artificial Sequence
<220> FEATURE:
<223> OTHER INFORMATION: recombinant plasmid

<400> SEQUENCE: 2
gacgtctaag aaaccattat tatcatgaca ttaacctata aaaataggcg tatcacgagg     60
cccttccgtc ttcacctcga gaggctttac actttatgct tccggctcgt ataatgtgtg    120
gaattgtgag cggataacaa ttgaattcta cggatccgat gtcgactcaa agcttcgatc    180
ccatggtacg cgtgctagag gcatcaaata aaacgaaagg ctcagtcgaa agactgggcc    240
tttcgtttta tctgttgttt gtcggtgaac gctctcctga gtaggacaaa tccgccgccc    300
tagacctagg gatatattcc gcttcctcgc tcactgactc gctacgctcg gtcgttcgac    360
```

```
tgcggcgagc ggaaatggct tacgaacggg gcggagattt cctggaagat gccaggaaga    420
tacttaacag ggaagtgaga gggccgcggc aaagccgttt ttccataggc tccgccccc     480 tgacaagcat cacgaaatct gacgctcaaa tcagtggtgg cgaaacccga caggactata    540
aagataccag gcgtttcccc ctggcggctc cctcgtgcgc tctcctgttc ctgcctttcg    600
gtttaccggt gtcattccgc tgttatggcc gcgtttgtct cattccacgc ctgacactca    660
gttccgggta ggcagttcgc tccaagctgg actgtatgca cgaaccccc gttcagtccg     720 accgctgcgc cttatccggt aactatcgtc ttgagtccaa cccggaaaga catgcaaaag    780
caccactggc agcagccact ggtaattgat ttagaggagt tagtcttgaa gtcatgcgcc    840
ggttaaggct aaactgaaag gacaagtttt ggtgactgcg ctcctccaag ccagttacct    900
cggttcaaag agttggtagc tcagagaacc ttcgaaaaac cgccctgcaa ggcggttttt    960
tcgttttcag agcaagagat tacgcgcaga ccaaaacgat ctcaagaaga tcatcttatt   1020
aatcagataa aatatttcta gatttcagtg caatttatct cttcaaatgt agcacctgaa   1080
gtcagcccca tacgatataa gttgttacta gtgcttggat tctcaccaat aaaaaacgcc   1140
cggcggcaac cgagcgttct gaacaaatcc agatggagtt ctgaggtcat tactggatct   1200
atcaacagga gtccaagcga gctctcgaac cccagagtcc cgctcagaag aactcgtcaa   1260
gaaggcgata aaggcgatg cgctgcgaat cgggagcggc gataccgtaa agcacgagga    1320
agcggtcagc ccattcgccg ccaagctctt cagcaatatc acgggtagcc aacgctatgt   1380
cctgatagcg gtccgccaca cccagccggc cacagtcgat gaatccagaa aagcggccat   1440
tttccaccat gatattcggc aagcaggcat cgccatgggt cacgacgaga tcctcgccgt   1500
cgggcatgcg cgccttgagc ctggcgaaca gttcggctgg cgcgagcccc tgatgctctt   1560
cgtccagatc atcctgatcg acaagaccgg cttccatccg agtacgtgct cgctcgatgc   1620
gatgtttcgc ttggtggtcg aatgggcagg tagccggatc aagcgtatgc agccgccgca   1680
ttgcatcagc catgatggat actttctcgg caggagcaag gtgagatgac aggagatcct   1740
gccccggcac ttcgcccaat agcagccagt cccttcccgc ttcagtgaca acgtcgagca   1800
cagctgcgca aggaacgccc gtcgtggcca gccacgatag ccgcgctgcc tcgtcctgca   1860
gttcattcag ggcaccggac aggtcggtct tgacaaaaag aaccgggcgc ccctgcgctg   1920
acagccggaa cacggcggca tcagagcagc cgattgtctg ttgtgcccag tcatagccga   1980
atagcctctc cacccaagcg gccggagaac ctgcgtgcaa tccatcttgt tcaatcatgc   2040
gaaacgatcc tcatcctgtc tcttgatcag atcttgatcc cctgcgccat cagatccttg   2100
gcggcaagaa agccatccag tttactttgc agggcttccc aaccttacca gagggcgccc   2160
cagctggcaa ttcc                                                      2174

<210> SEQ ID NO 3
<211> LENGTH: 12707
<212> TYPE: DNA
<213> ORGANISM: Artificial Sequence
<220> FEATURE:
<223> OTHER INFORMATION: recombinant plasmid

<400> SEQUENCE: 3
gacgtctaag aaaccattat tatcatgaca ttaacctata aaaataggcg tatcacgagg     60
ccctttcgtc ttcacctcga gaggctttac actttatgct tccggctcgt ataatgtgtg    120
gaattgtgag cggataacaa ttgaattcaa aggaggaaaa taaatgaagg aactgtgtga    180
ttgtttctgc ggtccgcacg gcgatcggca gctttaacgg ctctttagcg agcacctctg    240
```

```
caatcgatct gggtgcgacg gtcattaagg ccgccattga acgcgccaaa atcgacagcc    300
agcacgttga tgaggtgatc atgggcaatg tgttacaagc cggcctgggt caaaacccag    360
cgcgtcaagc actgttaaaa tctggtctgg ccgagaccgt gtgtggcttc accgtcaata    420
aggtttgcgg ctctggcctg aagagcgtgg ccctggcagc acaagcgatt caagccggtc    480
aggcacaaag catcgttgcg ggtggcatgg agaacatgtc tctggcgccg tacttattag    540
atgccaaagc ccgcagcggt tatcgcctgg gcgatggtca ggtgtacgac gtcatcttac    600
gcgatggctt aatgtgcgcg acccacggtt accacatggg tattacggcc gaaaacgtgg    660
cgaaagaata cggcattacg cgcgagatgc aggatgaatt agcactgcac tctcagcgca    720
aagcagcagc cgcgatcgag tctggtgcgt ttacggcgga aatcgtgcca gttaacgtgg    780
tcacgcgcaa gaagacgttc gttttcagcc aggacgagtt cccgaaggca aacagcaccg    840
cggaggcctt aggtgcctta cgcccagcct ttgacaaagc gggcacggtc accgccggta    900
atgcgagcgg catcaatgat ggtgcagcgg cactggtcat catggaagag agcgccgcat    960
tagcagcggg tctgacccca ttagcgcgca ttaaatctta tgccagcggc ggcgtcccac   1020
cagccctgat gggcatgggt ccggtcccag ccacgcaaaa agccctgcaa ttagcgggcc   1080
tgcaactggc cgacattgat ctgatcgagg cgaacgaggc gtttgcagcg cagttcctgg   1140
cggtgggtaa gaatctgggc ttcgacacgc agaaagtcaa tgtgaacggt ggcgcgattg   1200
cgttaggcca tccgattggt gcaagcggcg cacgcatctt agtgacgtta ctgcacgcca   1260
tgcaggcacg cgacaagacc ttaggcctgg cgaccttatg tattggtggc ggtcaaggta   1320
tcgccatggt gatcgaacgc ctgaactgaa gatctaggag gaaagcaaaa tgaaactgag   1380
caccaagctg tgctggtgtg gcatcaaggg tcgcctgcgc ccacaaaagc agcaacagct   1440
gcacaacacg aacctgcaaa tgaccgagct gaaaaagcag aagacggccg agcaaaagac   1500
ccgcccgcag aacgttggca tcaagggcat ccagatttat atcccgacgc agtgtgtcaa   1560
ccaatctgag ctggagaaat tcgatggcgt cagccagggt aagtacacca tcggcctggg   1620
ccagaccaac atgagcttcg tgaacgaccg tgaggacatc tattctatga gcctgacggt   1680
gctgtctaag ctgatcaaga gctacaacat cgacacgaat aagatcggtc gtctggaggt   1740
gggtacggag acgctgattg acaagagcaa aagcgtgaag tctgtcttaa tgcagctgtt   1800
cggcgagaac acggatgtcg agggtatcga caccctgaac gcgtgttacg gcggcaccaa   1860
cgcactgttc aatagcctga actggattga gagcaacgcc tgggatggcc gcgatgcgat   1920
cgtcgtgtgc ggcgatatcg ccatctatga caagggtgcg gcacgtccga ccggcggtgc   1980
aggcaccgtt gcgatgtgga ttggcccgga cgcaccaatt gtcttcgatt ctgtccgcgc   2040
gtcttacatg gagcacgcct acgactttta caagccggac ttcacgagcg aatacccgta   2100
cgtggacggc cacttctctc tgacctgcta tgtgaaggcg ctggaccagg tttataagtc   2160
ttatagcaaa aaggcgattt ctaagggcct ggtcagcgac ccggcaggca gcgacgccct   2220
gaacgtgctg aagtatttcg actacaacgt gttccatgtc ccgacctgca aattagtgac   2280
caaatcttat ggccgcctgt tatataatga tttccgtgcc aacccgcagc tgttcccgga   2340
ggttgacgcc gagctggcga cgcgtgatta cgacgagagc ctgaccgaca agaacatcga   2400
gaagaccttc gtcaacgtcg cgaagccgtt ccacaaagag cgtgtgggcc aaagcctgat   2460
cgtcccgacc aacacgggca acatgtatac cgcgtctgtc tacgcggcat tcgcgagcct   2520
gctgaattac gtcggttctg acgacctgca gggcaagcgc gttggcctgt tcagctacgg   2580
tagcggctta gcggccagcc tgtatagctg caaaattgtc ggcgacgtcc agcacatcat   2640
```

```
caaggagctg gacatcacca acaagctggc gaagcgcatc accgagacgc cgaaagatta    2700
cgaggcagcg atcgagttac gcgagaatgc gcatctgaag aagaacttca agccgcaagg    2760
tagcatcgag cacctgcaga gcggcgtcta ctacctgacg aacattgacg acaagttccg    2820
ccgttcttat gacgtcaaaa agtaactagt aggaggaaaa catcatggtg ctgacgaaca    2880
aaaccgtcat tagcggcagc aaggtgaagt ctctgagcag cgcccaaagc tctagcagcg    2940
gcccgtctag cagcagcgag gaggacgaca gccgtgacat tgagtctctg acaagaaga    3000 tccgcccgct ggaggagtta gaggccctgc tgagcagcgg caacaccaag cagctgaaga    3060
acaaggaagt tgcagcgctg gtgatccacg gtaagctgcc actgtatgcg ctggaaaaga    3120
aactgggcga tacgacgcgt gcggtcgcgg tgcgtcgcaa agccttaagc atcttagcgg    3180
aggccccggt gttagccagc gaccgcctgc cgtacaagaa ctacgactac gaccgcgtgt    3240
ttggcgcgtg ctgcgagaat gtcattggct acatgccgtt accggttggt gtgatcggcc    3300
cgctggtcat tgatggcacg agctatcaca ttccaatggc gaccacggaa ggttgcttag    3360
tcgccagcgc catgcgtggc tgtaaggcga ttaacgccgg cggtggcgcg acgaccgtgt    3420
taaccaagga tggtatgacg cgcggtccgg tcgtccgctt cccaacgctg aagcgcagcg    3480
gcgcgtgtaa gatttggctg gattctgagg agggccaaaa cgcgatcaag aaagccttca    3540
actctacgag ccgtttcgcg cgtttacagc atatccagac tgcctggcc ggcgacctgc    3600 tgttcatgcg cttccgcacc accacggggcg atgcgatggg catgaacatg atcagcaagg    3660
gcgtcgaata tagcctgaaa caaatggtgg aagaatatgg ctgggaggac atggaggttg    3720
tctctgtgag cggcaactat tgcaccgaca agaagccggc agccattaac tggattgagg    3780
gtcgcggcaa aagcgtcgtg gcagaagcga ccatcccagg cgacgtggtc cgtaaggttc    3840
tgaagagcga cgtcagcgcc ctggttgagt taaatatcgc gaaaaacctg gtcggcagcg    3900
cgatggcggg cagcgtgggt ggctttaacg cacatgcagc gaatctggtt acggcggttt    3960
tcttagcctt aggtcaggac ccagcccaaa atgtcgagag cagcaactgc attaccttaa    4020
tgaaagaggt tgacggtgac ctgcgcatca gcgtttctat gccgtctatc gaggtcggca    4080
cgatcggcgg cggcaccgtt ttagaaccgc aaggtgcgat gctggatctg ctgggcgtgc    4140
gcggcccaca tgcaacggcc ccaggcacca atgcccgcca actggcccgt atcgtggcct    4200
gcgcggttct ggcgggtgag ctgagcctgt gcgccgcatt agccgcgggc catttagttc    4260
aatctcacat gacccacaac cgcaagccgg cagaaccaac caagccaaat aacctggacg    4320
caaccgacat taaccgtctg aaggatggca gcgtcacgtg cattaaaagc tgagcatgct    4380
actaagcttc gatcccatgg tacgcgtgct agaggcatca aataaaacga aaggctcagt    4440
cgaaagactg ggcctttcgt tttatctgtt gtttgtcggt gaacgctctc ctgagtagga    4500
caaatccgcc gccctagacc tagggggatat attccgcttc ctcgctcact gactcgctac    4560
gctcggtcgt tcgactgcgg cgagcggaaa tggcttacga acggggcgga gatttcctgg    4620
aagatgccag gaagatactt aacagggaag tgagagggcc gcggcaaagc cgttttttcca    4680 taggctccgc ccccctgaca agcatcacga aatctgacgc tcaaatcagt ggtggcgaaa    4740
cccgacagga ctataaagat accaggcgtt tccccctggc ggctccctcg tgcgctctcc    4800
tgttcctgcc tttcggttta ccggtgtcat tccgctgtta tggccgcgtt tgtctcattc    4860
cacgcctgac actcagttcc gggtaggcag ttcgctccaa gctggactgt atgcacgaac    4920
cccccgttca gtccgaccgc tgcgccttat ccggtaacta tcgtcttgag tccaacccgg    4980
aaagacatgc aaaagcacca ctggcagcag ccactggtaa ttgatttaga ggagttagtc    5040
```

```
ttgaagtcat gcgccggtta aggctaaact gaaaggacaa gttttggtga ctgcgctcct    5100
ccaagccagt tacctcggtt caaagagttg gtagctcaga gaaccttcga aaaaccgccc    5160
tgcaaggcgg ttttttcgtt ttcagagcaa gagattacgc gcagaccaaa acgatctcaa    5220
gaagatcatc ttattaatca gataaaatat ttctagattt cagtgcaatt tatctcttca    5280
aatgtagcac ctgaagtcag ccccatacga tataagttgt tactagtgct tggattctca    5340
ccaataaaaa acgcccggcg gcaaccgagc gttctgaaca aatccagatg gagttctgag    5400
gtcattactg gatctatcaa caggagtcca agcgagctcg atatcaaatt acgccccgcc    5460
ctgccactca tcgcagtact gttgtaattc attaagcatt ctgccgacat ggaagccatc    5520
acagacggca tgatgaacct gaatcgccag cggcatcagc accttgtcgc cttgcgtata    5580
atatttgccc atggtgaaaa cggggcgaa gaagttgtcc atattggcca cgtttaaatc    5640
aaaactggtg aaactcaccc agggattggc tgagacgaaa aacatattct caataaaccc    5700
tttagggaaa taggccaggt tttcaccgta acacgccaca tcttgcgaat atatgtgtag    5760
aaactgccgg aaatcgtcgt ggtattcact ccagagcgat gaaaacgttt cagtttgctc    5820
atggaaaacg gtgtaacaag ggtgaacact atcccatatc accagctcac cgtctttcat    5880
tgccatacgg aattccggat gagcattcat caggcgggca agaatgtgaa taaaggccgg    5940
ataaaacttg tgcttatttt tctttacggt ctttaaaaag gccgtaatat ccagctgaac    6000
ggtctggtta taggtacatt gagcaactga ctgaaatgcc tcaaaatgtt ctttacgatg    6060
ccattgggat atatcaacgg tggtatatcc agtgattttt ttctccattt tagcttcctt    6120
agctcctgaa aatctcgata actcaaaaaa tacgcccggt agtgatctta tttcattatg    6180
gtgaaagttg gaacctctta cgtgccgatc aacgtctcat tttcgccaga tatcgacgtc    6240
tttacacttt atgcttccgg ctcgtataat gagcacatca gcaggacgca ctgaccgaat    6300 taggagggg accgggccca tgtcattacc gttcttaact tctgcaccgg aaaggttat     6360 tattttggt gaacactctg ctgtgtacaa caagcctgcc gtcgctgcta gtgtgtctgc     6420
gttgagaacc tacctgctaa taagcgagtc atctgcacca gatactattg aattggactt    6480
cccggacatt agctttaatc ataagtggtc catcaatgat ttcaatgcca tcaccgagga    6540
tcaagtaaac tcccaaaaat tggccaaggc tcaacaagcc accgatggct tgtctcagga    6600
actcgttagt cttttggatc cgttgttagc tcaactatcc gaatccttcc actaccatgc    6660
agcgttttgt ttcctgtata tgtttgtttg cctatgcccc catgccaaga atattaagtt    6720
ttctttaaag tctactttac ccatcggtgc tgggttgggc tcaagcgcct ctatttctgt    6780
atcactggcc ttagctatgg cctacttggg ggggttaata ggatctaatg acttggaaaa    6840
gctgtcagaa aacgataagc atatagtgaa tcaatgggcc ttcataggtg aaaagtgtat    6900
tcacggtacc ccttcaggaa tagataacgc tgtggccact tatggtaatg ccctgctatt    6960
tgaaaaagac tcacataatg gaacaataaa cacaaacaat tttaagttct tagatgattt    7020
cccagccatt ccaatgatcc taacctatac tagaattcca aggtctacaa aagatcttgt    7080
tgctcgcgtt cgtgtgttgg tcaccgagaa atttcctgaa gttatgaagc caattctaga    7140
tgccatgggt gaatgtgccc tacaaggctt agagatcatg actaagttaa gtaaatgtaa    7200
aggcaccgat gacgaggctg tagaaactaa taatgaactg tatgaacaac tattggaatt    7260
gataagaata aatcatggac tgcttgtctc aatcggtgtt tctcatcctg gattagaact    7320
tattaaaaat ctgagcgatg atttgagaat tggctccaca aaacttaccg gtgctggtgg    7380
cggcggttgc tctttgactt tgttacgaag agacattact caagagcaaa ttgacagctt    7440
```

```
caaaaagaaa ttgcaagatg attttagtta cgagacattt gaaacagact tgggtgggac    7500
tggctgctgt ttgttaagcg caaaaaattt gaataaagat cttaaaatca aatccctagt    7560
attccaatta tttgaaaata aaactaccac aaagcaacaa attgacgatc tattattgcc    7620
aggaaacacg aatttaccat ggacttcata ggaggcagat caaatgtcag agttgagagc    7680
cttcagtgcc ccagggaaag cgttactagc tggtggatat ttagttttag atacaaaata    7740
tgaagcattt gtagtcggat tatcggcaag aatgcatgct gtagcccatc cttacggttc    7800
attgcaaggg tctgataagt ttgaagtgcg tgtgaaaagt aaacaattta agatgggga    7860 gtggctgtac catataagtc ctaaaagtgg cttcattcct gtttcgatag gcggatctaa    7920
gaaccctttc attgaaaaag ttatcgctaa cgtatttagc tactttaaac ctaacatgga    7980
cgactactgc aatagaaact tgttcgttat tgatattttc tctgatgatg cctaccattc    8040
tcaggaggat agcgttaccg aacatcgtgg caacagaaga ttgagttttc attcgcacag    8100
aattgaagaa gttcccaaaa cagggctggg ctcctcggca ggtttagtca cagttttaac    8160
tacagctttg gcctcctttt ttgtatcgga cctggaaaat aatgtagaca aatatagaga    8220
agttattcat aatttagcac aagttgctca ttgtcaagct cagggtaaaa ttggaagcgg    8280
gtttgatgta gcggcggcag catatggatc tatcagatat agaagattcc cacccgcatt    8340
aatctctaat ttgccagata ttggaagtgc tacttacggc agtaaactgg cgcatttggt    8400
tgatgaagaa gactggaata ttacgattaa aagtaaccat ttaccttcgg gattaacttt    8460
atggatgggc gatattaaga atggttcaga acagtaaaaa ctggtccaga aggtaaaaaa    8520
ttggtatgat tcgcatatgc cagaaagctt gaaaatatat acagaactcg atcatgcaaa    8580
ttctagattt atggatggac tatctaaact agatcgctta cacgagactc atgacgatta    8640
cagcgatcag atatttgagt ctcttgagag gaatgactgt acctgtcaaa agtatcctga    8700
aatcacagaa gttagagatg cagttgccac aattagacgt tcctttagaa aaataactaa    8760
agaatctggt gccgatatcg aacctcccgt acaaactagc ttattggatg attgccagac    8820
cttaaaagga gttcttactt gcttaatacc tggtgctggt ggttatgacg ccattgcagt    8880
gattactaag caagatgttg atcttagggc tcaaaccgct aatgacaaaa gatttctaa    8940 ggttcaatgg ctggatgtaa ctcaggctga ctggggtgtt aggaaagaaa agatccgga    9000 aacttatctt gataaatagg aggtaatact catgaccgtt tacacagcat ccgttaccgc    9060
acccgtcaac atcgcaaccc ttaagtattg ggggaaaagg gacacgaagt tgaatctgcc    9120
caccaattcg tccatatcag tgactttatc gcaagatgac ctcagaacgt tgacctctgc    9180
ggctactgca cctgagtttg aacgcgacac tttgtggtta aatggagaac cacacagcat    9240
cgacaatgaa agaactcaaa attgtctgcg cgacctacgc caattaagaa aggaaatgga    9300
atcgaaggac gcctcattgc ccacattatc tcaatggaaa ctccacattg tctccgaaaa    9360
taactttcct acagcagctg gtttagcttc ctccgctgct ggctttgctg cattggtctc    9420
tgcaattgct aagttatacc aattaccaca gtcaacttca gaaatatcta gaatagcaag    9480 aaagggtct ggttcagctt gtagatcgtt gtttggcgga tacgtggcct gggaaatggg    9540
aaaagctgaa gatggtcatg attccatggc agtacaaatc gcagacagct ctgactggcc    9600
tcagatgaaa gcttgtgtcc tagttgtcag cgatattaaa aaggatgtga gttcactca    9660 gggtatgcaa ttgaccgtgg caacctccga actatttaaa gaaagaattg aacatgtcgt    9720
accaaagaga tttgaagtca tgcgtaaagc cattgttgaa aaagatttcg ccacctttgc    9780
aaaggaaaca atgatggatt ccaactcttt ccatgccaca tgtttggact ctttccctcc    9840
```

```
aatattctac atgaatgaca cttccaagcg tatcatcagt tggtgccaca ccattaatca    9900
gttttacgga gaaacaatcg ttgcatacac gtttgatgca ggtccaaatg ctgtgttgta    9960
ctacttagct gaaaatgagt cgaaactctt tgcatttatc tataaattgt ttggctctgt   10020
tcctggatgg gacaagaaat ttactactga gcagcttgag gctttcaacc atcaatttga   10080
atcatctaac tttactgcac gtgaattgga tcttgagttg caaaaggatg ttgccagagt   10140
gattttaact caagtcggtt caggcccaca agaaacaaac gaatctttga ttgacgcaaa   10200
gactggtcta ccaaaggaat aactgcagcc cgggaggagg attactatat gcaaacggaa   10260
cacgtcattt tattgaatgc acagggagtt cccacgggta cgctggaaaa gtatgccgca   10320
cacacggcag acacccgctt acatctcgcg ttctccagtt ggctgtttaa tgccaaagga   10380
caattattag ttacccgccg cgcactgagc aaaaaagcat ggcctggcgt gtggactaac   10440
tcggtttgtg ggcacccaca actgggagaa agcaacgaag acgcagtgat ccgccgttgc   10500
cgttatgagc ttggcgtgga aattacgcct cctgaatcta tctatcctga ctttcgctac   10560
cgcgccaccg atccgagtgg cattgtggaa aatgaagtgt gtccggtatt gccgcacgc    10620
accactagtg cgttacagat caatgatgat gaagtgatgg attatcaatg gtgtgattta   10680
gcagatgtat tacacggtat tgatgccacg ccgtgggcgt tcagtccgtg gatggtgatg   10740
caggcgacaa atcgcgaagc cagaaaacga ttatctgcat ttacccagct taaataaccc   10800
gggggatcca ctagttctag agcggccgcc accgcggagg aggaatgagt aatggacttt   10860
ccgcagcaac tcgaagcctg cgttaagcag gccaaccagg cgctgagccg ttttatcgcc   10920
ccactgccct ttcagaacac tcccgtggtc gaaaccatgc agtatggcgc attattaggt   10980
ggtaagcgcc tgcgaccttt cctggtttat gccaccggtc atatgttcgg cgttagcaca   11040
aacacgctgg acgcacccgc tgccgccgtt gagtgtatcc acgcttactc attaattcat   11100
gatgatttac cggcaatgga tgatgacgat ctgcgtcgcg gtttgccaac ctgccatgtg   11160
aagtttggcg aagcaaacgc gattctcgct ggcgacgctt tacaaacgct ggcgttctcg   11220
attttaagcg atgccgatat gccggaagtg tcggaccgcg acagaatttc gatgatttct   11280
gaactggcga gcgccagtgg tattgccgga atgtgcggtg gtcaggcatt agatttagac   11340
gcggaaggca aacacgtacc tctggacgcg cttgagcgta ttcatcgtca taaaaccggc   11400
gcattgattc gcgccgccgt tcgccttggt gcattaagcg ccggagataa aggacgtcgt   11460
gctctgccgg tactcgacaa gtatgcagag agcatcggcc ttgccttcca ggttcaggat   11520
gacatcctgg atgtggtggg agatactgca acgttgggaa aacgccaggg tgccgaccag   11580
caacttggta aaagtaccta ccctgcactt ctgggtcttg agcaagcccg gaagaaagcc   11640
cgggatctga tcgacgatgc ccgtcagtcg ctgaaacaac tggctgaaca gtcactcgat   11700
acctcggcac tggaagcgct agcggactac atcatccagc gtaataaata agagctctcg   11760
aaccccagag tcccgctcag aagaactcgt caagaaggcg atagaaggcg atgcgctgcg   11820
aatcgggagc ggcgataccg taaagcacga ggaagcggtc agcccattcg ccgccaagct   11880
cttcagcaat atcacgggta gccaacgcta tgtcctgata gcggtccgcc acacccagcc   11940
ggccacagtc gatgaatcca gaaaagcggc cattttccac catgatattc ggcaagcagg   12000
catcgccatg ggtcacgacg agatcctcgc cgtcgggcat gcgcgccttg agcctggcga   12060
acagttcggc tggcgcgagc ccctgatgct cttcgtccag atcatcctga tcgacaagac   12120
cggcttccat ccgagtacgt gctcgctcga tgcgatgttt cgcttggtgg tcgaatgggc   12180
aggtagccgg atcaagcgta tgcagccgcc gcattgcatc agccatgatg gatactttct   12240
```

| | |
|---|---|
| cggcaggagc aaggtgagat gacaggagat cctgccccgg cacttcgccc aatagcagcc | 12300 |
| agtcccttcc cgcttcagtg acaacgtcga gcacagctgc gcaaggaacg cccgtcgtgg | 12360 |
| ccagccacga tagccgcgct gcctcgtcct gcagttcatt cagggcaccg gacaggtcgg | 12420 |
| tcttgacaaa aagaaccggg cgcccctgcg ctgacagccg gaacacggcg gcatcagagc | 12480 |
| agccgattgt ctgttgtgcc cagtcatagc cgaatagcct ctccacccaa gcggccggag | 12540 |
| aacctgcgtg caatccatct tgttcaatca tgcgaaacga tcctcatcct gtctcttgat | 12600 |
| cagatcttga tcccctgcgc catcagatcc ttggcggcaa gaaagccatc cagtttactt | 12660 |
| tgcagggctt cccaacctta ccagagggcg ccccagctgg caattcc | 12707 |

<210> SEQ ID NO 4
<211> LENGTH: 12707
<212> TYPE: DNA
<213> ORGANISM: Artificial Sequence
<220> FEATURE:
<223> OTHER INFORMATION: recombinant vector

<400> SEQUENCE: 4

| | |
|---|---|
| gacgtctaag aaaccattat tatcatgaca ttaacctata aaaataggcg tatcacgagg | 60 |
| ccctttcgtc ttcacctcga gaggctttac actttatgct tccggctcgt ataatgtgtg | 120 |
| gaattgtgag cggataacaa ttgaattcaa aggaggaaaa taaatgaag aactgtgtga | 180 |
| ttgtttctgc ggtccgcacg gcgatcggca gctttaacgg ctctttagcg agcacctctg | 240 |
| caatcgatct gggtgcgacg gtcattaagg ccgccattga acgcgccaaa atcgacagcc | 300 |
| agcacgttga tgaggtgatc atgggcaatg tgttacaagc cggcctgggt caaaacccag | 360 |
| cgcgtcaagc actgttaaaa tctggtctgg ccgagaccgt gtgtggcttc accgtcaata | 420 |
| aggtttgcgg ctctggcctg aagagcgtgg ccctggcagc acaagcgatt caagccggtc | 480 |
| aggcacaaag catcgttgcg ggtggcatgg agaacatgtc tctggcgccg tacttattag | 540 |
| atgccaaagc ccgcagcggt tatcgcctgg gcgatggtca ggtgtacgac gtcatcttac | 600 |
| gcgatggctt aatgtgcgcg acccacggtt accacatggg tattacggcc gaaaacgtgg | 660 |
| cgaaagaata cggcattacg cgcgagatgc aggatgaatt agcactgcac tctcagcgca | 720 |
| aagcagcagc cgcgatcgag tctggtgcgt ttacggcgga aatcgtgcca gttaacgtgg | 780 |
| tcacgcgcaa gaagacgttc gttttcagcc aggacgagtt cccgaaggca aacagcaccg | 840 |
| cggaggcctt aggtgcctta cgcccagcct ttgacaaagc gggcacggtc accgccggta | 900 |
| atgcgagcgg catcaatgat ggtgcagcgg cactggtcat catggaagag agcgccgcat | 960 |
| tagcagcggg tctgaccccca ttagcgcgca ttaaatctta tgccagcggc ggcgtcccac | 1020 |
| cagccctgat gggcatgggt ccggtcccag ccacgcaaaa agccctgcaa ttagcgggcc | 1080 |
| tgcaactggc cgacattgat ctgatcgagg cgaacgaggc gtttgcagcg cagttcctgg | 1140 |
| cggtgggtaa gaatctgggc ttcgacacgc agaaagtcaa tgtgaacggt ggcgcgattg | 1200 |
| cgttaggcca tccgattggt gcaagcggcg cacgcatctt agtgacgtta ctgcacgcca | 1260 |
| tgcaggcacg cgacaagacc ttaggcctgg cgaccttatg tattggtggc ggtcaaggta | 1320 |
| tcgccatggt gatcgaacgc ctgaactgaa gatctaggag gaaagcaaaa tgaaactgag | 1380 |
| caccaagctg tgctggtgtg gcatcaaggg tcgcctgcgc ccacaaaagc agcaacagct | 1440 |
| gcacaacacg aacctgcaaa tgaccgagct gaaaaagcag aagacggccg agcaaaagac | 1500 |
| ccgcccgcag aacgttggca tcaagggcat ccagatttat atcccgacgc agtgtgtcaa | 1560 |
| ccaatctgag ctggagaaat tcgatggcgt cagccagggt aagtacacca tcggcctggg | 1620 |

```
ccagaccaac atgagcttcg tgaacgaccg tgaggacatc tattctatga gcctgacggt   1680
gctgtctaag ctgatcaaga gctacaacat cgacacgaat aagatcggtc gtctggaggt   1740
gggtacggag acgctgattg acaagagcaa aagcgtgaag tctgtcttaa tgcagctgtt   1800
cggcgagaac acggatgtcg agggtatcga caccctgaac gcgtgttacg gcggcaccaa   1860
cgcactgttc aatagcctga actggattga gagcaacgcc tgggatggcc gcgatgcgat   1920
cgtcgtgtgc ggcgatatcg ccatctatga caagggtgcg gcacgtccga ccggcggtgc   1980
aggcaccgtt gcgatgtgga ttggcccgga cgcaccaatt gtcttcgatt ctgtccgcgc   2040
gtcttacatg gagcacgcct acgactttta caagccggac ttcacgagcg aatacccgta   2100
cgtggacggc cacttctctc tgacctgcta tgtgaaggcg ctggaccagg tttataagtc   2160
ttatagcaaa aaggcgattt ctaagggcct ggtcagcgac ccggcaggca gcgacgccct   2220
gaacgtgctg aagtatttcg actacaacgt gttccatgtc ccgacctgca aattagtgac   2280
caaatcttat ggccgcctgt tatataatga tttccgtgcc aacccgcagc tgttcccgga   2340
ggttgacgcc gagctggcga cgcgtgatta cgacgagagc ctgaccgaca gaacatcga   2400 gaagaccttc gtcaacgtcg cgaagccgtt ccacaaagag cgtgtggccc aaagcctgat   2460
cgtcccgacc aacacgggca acatgtatac cgcgtctgtc tacgcggcat tcgcgagcct   2520
gctgaattac gtcggttctg acgacctgca gggcaagcgc gttggcctgt tcagctacgg   2580
tagcggctta gcggccagcc tgtatagctg caaaattgtc ggcgacgtcc agcacatcat   2640
caaggagctg gacatcacca acaagctggc gaagcgcatc accgagacgc cgaaagatta   2700
cgaggcagcg atcgagttac gcgagaatgc gcatctgaag aagaacttca gccgcaagg   2760 tagcatcgag cacctgcaga gcggcgtcta ctacctgacg aacattgacg acaagttccg   2820
ccgttcttat gacgtcaaaa agtaactagt aggaggaaaa catcatggtg ctgacgaaca   2880
aaaccgtcat tagcggcagc aaggtgaagt ctctgagcag cgcccaaagc tctagcagcg   2940
gcccgtctag cagcagcgag gaggacgaca gccgtgacat tgagtctctg acaagaaga   3000 tccgcccgct ggaggagtta gaggccctgc tgagcagcgg caacaccaag cagctgaaga   3060
acaaggaagt tgcagcgctg gtgatccacg gtaagctgcc actgtatgcg ctggaaaaga   3120
aactgggcga tacgacgcgt gcggtcgcgt gcgtcgcaa agccttaagc atcttagcgg   3180 aggcccccggt gttagccagc gaccgcctgc cgtacaagaa ctacgactac gaccgcgtgt   3240
ttggcgcgtg ctgcgagaat gtcattggct acatgccgtt accggttggt gtgatcggcc   3300
cgctggtcat tgatggcacg agctatcaca ttccaatggc gaccacggaa ggttgcttag   3360
tcgccagcgc catgcgtggc tgtaaggcga ttaacgccgg cggtggcgcg acgaccgtgt   3420
taaccaagga tggtatgacg cgcggtccgg tcgtccgctt cccaacgctg aagcgcagcg   3480
gcgcgtgtaa gatttggctg gattctgagg agggccaaaa cgcgatcaag aaagccttca   3540
actctacgag ccgtttcgcg cgtttacagc atatccagac ctgcctggcc ggcgacctgc   3600
tgttcatgcg cttccgcacc accacggggcg atgcgatggg catgaacatg atcagcaagg   3660
gcgtcgaata tagcctgaaa caaatggtgg aagaatatgg ctgggaggac atggaggttg   3720
tctctgtgag cggcaactat tgcaccgaca gaagccggc agccattaac tggattgagg   3780
gtcgcggcaa aagcgtcgtg gcagaagcga ccatcccagg cgacgtggtc cgtaaggttc   3840
tgaagagcga cgtcagcgcc ctggttgagt taaatatcgc gaaaaacctg gtcggcagcg   3900
cgatggcggg cagcgtgggt ggctttaacg cacatgcagc gaatctggtt acggcggttt   3960
tcttagcctt aggtcaggac ccagcccaaa atgtcgagag cagcaactgc attaccttaa   4020
```

```
tgaaagaggt tgacggtgac ctgcgcatca gcgtttctat gccgtctatc gaggtcggca   4080
cgatcggcgg cggcaccgtt ttagaaccgc aaggtgcgat gctggatctg ctgggcgtgc   4140
gcggcccaca tgcaacggcc ccaggcacca atgcccgcca actggcccgt atcgtggcct   4200
gcgcggttct ggcgggtgag ctgagcctgt gcgccgcatt agccgcgggc catttagttc   4260
aatctcacat gacccacaac cgcaagccgg cagaaccaac caagccaaat aacctggacg   4320
caaccgacat taaccgtctg aaggatggca gcgtcacgtg cattaaaagc tgagcatgct   4380
actaagcttc gatcccatgg tacgcgtgct agaggcatca aataaaacga aaggctcagt   4440
cgaaagactg ggcctttcgt tttatctgtt gtttgtcggt gaacgctctc ctgagtagga   4500
caaatccgcc gccctagacc tagqggatat attccgcttc ctcgctcact gactcgctac   4560
gctcggtcgt tcgactgcgg cgagcggaaa tggcttacga acggggcgga gatttcctgg   4620
aagatgccag gaagatactt aacagggaag tgagagggcc gcggcaaagc cgttttccca   4680
taggctccgc cccctgaca agcatcacga aatctgacgc tcaaatcagt ggtggcgaaa   4740
cccgacagga ctataaagat accaggcgtt tccccctggc ggctccctcg tgcgctctcc   4800
tgttcctgcc tttcggttta ccggtgtcat tccgctgtta tggccgcgtt tgtctcattc   4860
cacgcctgac actcagttcc gggtaggcag ttcgctccaa gctggactgt atgcacgaac   4920
cccccgttca gtccgaccgc tgcgccttat ccggtaacta tcgtcttgag tccaacccgg   4980
aaagacatgc aaaagcacca ctggcagcag ccactggtaa ttgatttaga ggagttagtc   5040
ttgaagtcat gcgccggtta aggctaaact gaaaggacaa gttttggtga ctgcgctcct   5100
ccaagccagt tacctcggtt caaagagttg gtagctcaga gaaccttcga aaaccgccc   5160 tgcaaggcgg tttttttcgtt ttcagagcaa gagattacgc gcagaccaaa acgatctcaa   5220
gaagatcatc ttattaatca gataaaatat ttctagattt cagtgcaatt tatctcttca   5280
aatgtagcac ctgaagtcag ccccatacga tataagttgt tactagtgct tggattctca   5340
ccaataaaaa acgcccggcg gcaaccgagc gttctgaaca atccagatg gagttctgag    5400 gtcattactg gatctatcaa caggagtcca agcgagctct tatttattac gctggatgat   5460
gtagtccgct agcgcttcca gtgccgaggt atcgagtgac tgttcagcca gttgtttcag   5520
cgactgacgg gcatcgtcga tcagatcccg ggctttcttc cgggcttgct caagacccag   5580
aagtgcaggg taggtacttt taccaagttg ctggtcggca ccctggcgtt ttcccaacgt   5640
tgcagtatct cccaccacat ccaggatgtc atcctgaacc tggaaggcaa ggccgatgct   5700
ctctgcatac ttgtcgagta ccggcagagc acgacgtcct ttatctccgg cgcttaatgc   5760
accaaggcga acggcggcgc gaatcaatgc gccggtttta tgacgatgaa tacgctcaag   5820
cgcgtccaga ggtacgtgtt tgccttccgc gtctaaatct aatgcctgac caccgcacat   5880
tccggcaata ccactggcgc tcgccagttc agaaatcatc gaaattctgt cgcggtccga   5940
cacttccggc atatcggcat cgcttaaaat cgagaacgcc agcgtttgta aagcgtcgcc   6000
agcgagaatc gcgtttgctt cgccaaactt cacatggcag gttggcaaac cgcgacgcag   6060
atcgtcatca tccattgccg gtaaatcatc atgaattaat gagtaagcgt ggatacactc   6120
aacggcggca gcgggtgcgt ccagcgtgtt tgtgctaacg ccgaacatat gaccggtggc   6180
ataaaccagg aaaggtcgca ggcgcttacc acctaataat gcgccatact gcatggtttc   6240
gaccacggga gtgttctgaa agggcagtgg ggcgataaaa cggctcagcg cctggttggc   6300
ctgcttaacg caggcttcga gttgctgcgg aaagtccatt actcattcct cctccgcggt   6360
ggcggccgct ctagaactag tggatccccc gggttattta agctgggtaa atgcagataa   6420
```

```
tcgttttctg gcttcgcgat ttgtcgcctg catcaccatc cacggactga acgcccacgg   6480
cgtggcatca ataccgtgta atacatctgc taaatcacac cattgataat ccatcacttc   6540
atcatcattg atctgtaacg cactagtggt gcgtgcggca ataccggac acacttcatt    6600 ttccacaatg ccactcggat cggtggcgcg gtagcgaaag tcaggataga tagattcagg   6660
aggcgtaatt tccacgccaa gctcataacg gcaacggcgg atcactgcgt cttcgttgct   6720
ttctcccagt tgtgggtgcc cacaaaccga gttagtccac acgccaggcc atgcttttt    6780 gctcagtgcg cggcgggtaa ctaataattg tcctttggca ttaaacagcc aactggagaa   6840
cgcgagatgt aagcgggtgt ctgccgtgtg tgcggcatac ttttccagcg tacccgtggg   6900
aactccctgt gcattcaata aaatgacgtg ttccgtttgc atatagtaat cctcctcccg   6960
ggctgcagtt attcctttgg tagaccagtc tttgcgtcaa tcaaagattc gtttgtttct   7020
tgtgggcctg aaccgacttg agttaaaatc actctggcaa catccttttg caactcaaga   7080
tccaattcac gtgcagtaaa gttagatgat tcaaattgat ggttgaaagc ctcaagctgc   7140
tcagtagtaa atttcttgtc ccatccagga acagagccaa acaatttata gataaatgca   7200
aagagtttcg actcattttc agctaagtag tacaacacag catttggacc tgcatcaaac   7260
gtgtatgcaa cgattgtttc tccgtaaaac tgattaatgg tgtggcacca actgatgata   7320
cgcttggaag tgtcattcat gtagaatatt ggagggaaag agtccaaaca tgtggcatgg   7380
aaagagttgg aatccatcat tgtttccttt gcaaggtgg cgaaatcttt ttcaacaatg    7440
gctttacgca tgacttcaaa tctctttggt acgacatgtt caattctttc tttaaatagt   7500
tcggaggttg ccacggtcaa ttgcataccc tgagtggaac tcacatcctt tttaatatcg   7560
ctgacaacta ggacacaagc tttcatctga ggccagtcag agctgtctgc gatttgtact   7620
gccatggaat catgaccatc ttcagctttt cccatttccc aggccacgta tccgccaaac   7680
aacgatctac aagctgaacc agaccccttt cttgctattc tagatatttc tgaagttgac   7740
tgtggtaatt ggtataactt agcaattgca gagaccaatg cagcaaagcc agcagcggag   7800
gaagctaaac cagctgctgt aggaaagtta ttttcggaga caatgtggag tttccattga   7860
gataatgtgg gcaatgaggc gtccttcgat tccatttcct ttcttaattg gcgtaggtcg   7920
cgcagacaat tttgagttct ttcattgtcg atgctgtgtg gttctccatt taaccacaaa   7980
gtgtcgcgtt caaactcagg tgcagtagcc gcagaggtca acgttctgag gtcatcttgc   8040
gataaagtca ctgatatgga cgaattggtg ggcagattca acttcgtgtc ccttttcccc   8100
caatacttaa gggttgcgat gttgacgggt gcggtaacgg atgctgtgta aacggtcatg   8160
agtattacct cctatttatc aagataagtt tccggatctt tttctttcct aacaccccag   8220
tcagcctgag ttacatccag ccattgaacc ttagaaaatc ttttgtcatt agcggtttga   8280
gccctaagat caacatcttg cttagtaatc actgcaatgg cgtcataacc accagcacca   8340
ggtattaagc aagtaagaac tccttttaag gtctggcaat catccaataa gctagtttgt   8400
acgggaggtt cgatatcggc accagattct ttagttattt ttctaaagga acgtctaatt   8460
gtggcaactg catctctaac ttctgtgatt tcaggatact tttgacaggt acagtcattc   8520
ctctcaagag actcaaatat ctgatcgctg taatcgtcat gagtctcgtg taagcgatct   8580
agtttagata gtccatccat aaatctagaa tttgcatgat cgagttctgt atatattttc   8640 aagcttctg gcatatgcga atcataccaa ttttttacct tctggaccag tttactgtt     8700 tctgaaccat tcttaatatc gcccatccat aaagttaatc ccgaaggtaa atggttactt   8760
ttaatcgtaa tattccagtc ttcttcatca accaaatgcg ccagtttact gccgtaagta   8820
```

```
gcacttccaa tatctggcaa attagagatt aatgcgggtg ggaatcttct atatctgata    8880
gatccatatg ctgccgccgc tacatcaaac ccgcttccaa ttttaccctg agcttgacaa    8940
tgagcaactt gtgctaaatt atgaataact tctctatatt tgtctacatt attttccagg    9000
tccgatacaa aaaggaggc caaagctgta gttaaaactg tgactaaacc tgccgaggag     9060
cccagccctg ttttgggaac ttcttcaatt ctgtgcgaat gaaaactcaa tcttctgttg    9120
ccacgatgtt cggtaacgct atcctcctga gaatggtagg catcatcaga gaaaatatca    9180
ataacgaaca agtttctatt gcagtagtcg tccatgttag gtttaaagta gctaaatacg    9240
ttagcgataa cttttttcaat gaaagggttc ttagatccgc ctatcgaaac aggaatgaag   9300 ccactttttag gacttatatg gtacagccac tccccatctt taaattgttt acttttcaca   9360
cgcacttcaa acttatcaga cccttgcaat gaaccgtaag gatgggctac agcatgcatt    9420
cttgccgata atccgactac aaatgcttca tattttgtat ctaaaactaa atatccacca    9480
gctagtaacg cttttccctgg ggcactgaag gctctcaact ctgacatttg atctgcctcc   9540
tatgaagtcc atggtaaatt cgtgtttcct ggcaataata gatcgtcaat ttgttgcttt    9600
gtggtagttt tattttcaaa taattggaat actagggatt tgattttaag atctttattc    9660
aaattttttg cgcttaacaa acagcagcca gtcccaccca agtctgtttc aaatgtctcg    9720
taactaaaat catcttgcaa tttcttttg aagctgtcaa tttgctcttg agtaatgtct     9780
cttcgtaaca aagtcaaaga gcaaccgccg ccaccagcac cggtaagttt tgtggagcca    9840
attctcaaat catcgctcag attttttaata agttctaatc caggatgaga aacaccgatt   9900
gagacaagca gtccatgatt tattcttatc aattccaata gttgttcata cagttcatta   9960
ttagtttcta cagcctcgtc atcggtgcct ttacatttac ttaacttagt catgatctct   10020
aagccttgta gggcacattc acccatggca tctagaattg gcttcataac ttcaggaaat   10080
ttctcggtga ccaacacacg aacgcgagca acaagatctt ttgtagacct tggaattcta   10140
gtataggtta ggatcattgg aatggctggg aaatcatcta agaacttaaa attgtttgtg   10200
tttattgttc cattatgtga gtcttttttca aatagcaggg cattaccata agtggccaca   10260
gcgttatcta ttcctgaagg ggtaccgtga atacactttt cacctatgaa ggcccattga    10320
ttcactatat gcttatcgtt ttctgacagc ttttccaagt cattagatcc tattaaccc     10380 cccaagtagg ccatagctaa ggccagtgat acagaaatag aggcgcttga gcccaaccca    10440
gcaccgatgg gtaaagtaga ctttaaagaa aacttaatat tcttggcatg ggggcatagg   10500
caaacaaaca tatacaggaa acaaaacgct gcatggtagt ggaaggattc ggatagttga    10560
gctaacaacg gatccaaaag actaacgagt tcctgagaca agccatcggt ggcttgttga   10620
gccttggcca attttttggga gtttacttga tcctcggtga tggcattgaa atcattgatg   10680
gaccacttat gattaaagct aatgtccggg aagtccaatt caatagtatc tggtgcagat    10740
gactcgctta ttagcaggta ggttctcaac gcagacacac tagcagcgac ggcaggcttg    10800
ttgtacacag cagagtgttc accaaaaata ataaccttc ccggtgcaga agttaagaac     10860
ggtaatgaca tgggcccggt accctcctaa ttcggtcag tgcgtcctgc tgatgtgctc     10920
attatacgag ccggaagcat aaagtgtaaa gacgtcgata tctggcgaaa atgagacgtt    10980
gatcggcacg taagaggttc caactttcac cataatgaaa taagatcact accgggcgta    11040 tttttttgagt tatcgagatt ttcaggagct aaggaagcta aaatggagaa aaaaatcact    11100
ggatatacca ccgttgatat atcccaatgg catcgtaaag aacatttga ggcatttcag     11160 tcagttgctc aatgtaccta taaccagacc gttcagctgg atattacggc cttttttaaag   11220
```

```
accgtaaaga aaaataagca caagttttat ccggccttta ttcacattct tgcccgcctg    11280
atgaatgctc atccggaatt ccgtatggca atgaaagacg gtgagctggt gatatgggat    11340
agtgttcacc cttgttacac cgttttccat gagcaaactg aaacgttttc atcgctctgg    11400
agtgaatacc acgacgattt ccggcagttt ctacacatat attcgcaaga tgtggcgtgt    11460
tacggtgaaa acctgcccta tttccctaaa gggtttattg agaatatgtt tttcgtctca    11520
gccaatccct gggtgagttt caccagtttt gatttaaacg tggccaatat ggacaacttc    11580 ttcgccccg ttttcaccat gggcaaatat tatacgcaag cgacaaggt gctgatgccg     11640 ctggcgattc aggttcatca tgccgtctgt gatggcttcc atgtcggcag aatgcttaat    11700
gaattacaac agtactgcga tgagtggcag ggcggggcgt aatttgatat cgagctctcg    11760
aaccccagag tcccgctcag aagaactcgt caagaaggcg atagaaggcg atgcgctgcg    11820
aatcgggagc ggcgataccg taaagcacga ggaagcggtc agcccattcg ccgccaagct    11880
cttcagcaat atcacgggta gccaacgcta tgtcctgata gcggtccgcc acacccagcc    11940
ggccacagtc gatgaatcca gaaaagcggc cattttccac catgatattc ggcaagcagg    12000
catcgccatg gtcacgacg agatcctcgc cgtcgggcat gcgcgccttg agcctggcga    12060
acagttcggc tggcgcgagc ccctgatgct cttcgtccag atcatcctga tcgacaagac    12120
cggcttccat ccgagtacgt gctcgctcga tgcgatgttt cgcttggtgg tcgaatgggc    12180
aggtagccgg atcaagcgta tgcagccgcc gcattgcatc agccatgatg gatactttct    12240
cggcaggagc aaggtgagat gacaggagat cctgccccgg cacttcgccc aatagcagcc    12300
agtcccttcc cgcttcagtg acaacgtcga gcacagctgc gcaaggaacg cccgtcgtgg    12360
ccagccacga tagccgcgct gcctcgtcct gcagttcatt cagggcaccg gacaggtcgg    12420
tcttgacaaa aagaaccggg cgcccctgcg ctgacagccg aacacggcg gcatcagagc      12480 agccgattgt ctgttgtgcc cagtcatagc cgaatagcct ctccacccaa gcggccgag     12540 aacctgcgtg caatccatct tgttcaatca tgcgaaacga tcctcatcct gtctcttgat    12600
cagatcttga tccctgcgc catcagatcc ttggcggcaa gaaagccatc cagtttactt     12660
tgcagggctt cccaacctta ccagagggcg ccccagctgg caattcc                  12707
```

<210> SEQ ID NO 5
<211> LENGTH: 13055
<212> TYPE: DNA
<213> ORGANISM: Artificial Sequence
<220> FEATURE:
<223> OTHER INFORMATION: recombinant vector

<400> SEQUENCE: 5

```
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa agttggccc agggcttccc     360 ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
```

```
ggcttactat gttggcactg atgagggtgt cagtgaagtg cttcatgtgg caggagaaaa      660
aaggctgcac cggtgcgtca gcagaatatg tgatacagga tatattccgc ttcctcgctc      720
actgactcgc tacgctcggt cgttcgactg cggcgagcgg aaatggctta cgaacggggc      780
ggagatttcc tggaagatgc caggaagata cttaacaggg aagtgagagg gccgcggcaa      840
agccgttttt ccataggctc cgccccctg acaagcatca cgaaatctga cgctcaaatc       900
agtggtggcg aaacccgaca ggactataaa gataccaggc gtttccccct ggcggctccc      960
tcgtgcgctc tcctgttcct gcctttcggt ttaccggtgt cattccgctg ttatggccgc     1020
gtttgtctca ttccacgcct gacactcagt tccgggtagg cagttcgctc caagctggac     1080
tgtatgcacg aacccccgt tcagtccgac cgctgcgcct tatccggtaa ctatcgtctt      1140
gagtccaacc cggaaagaca tgcaaaagca ccactggcag cagccactgg taattgattt     1200
agaggagtta gtcttgaagt catgcgccgg ttaaggctaa actgaaagga caagttttgg     1260
tgactgcgct cctccaagcc agttacctcg gttcaaagag ttggtagctc agagaacctt     1320
cgaaaaaccg ccctgcaagg cggttttttc gttttcagag caagagatta cgcgcagacc     1380
aaaacgatct caagaagatc atcttattaa tcagataaaa tatttctaga tttcagtgca     1440
atttatctct tcaaatgtag cacctgaagt cagccccata cgatataagt tgtaattctc     1500
atgtttgaca gcttatcatc gataagcttc cgatggcgcg ccgagaggct ttacacttta     1560
tgcttccggc tcgtataatg tgtggaattg tgagcggata caattgaat tcaaaggagg      1620 ccatcctggc catgaagaac tgtgtgattg tttctgcggt ccgcacggcg atcggcagct     1680
ttaacggctc tttagcgagc acctctgcaa tcgatctggg tgcgacggtc attaaggccg     1740
ccattgaacg cgccaaaatc gacagccagc acgttgatga ggtgatcatg gcaatgtgt      1800 tacaagccgg cctgggtcaa aacccagcgc gtcaagcact gttaaaatct ggtctggccg     1860
agaccgtgtg tggcttcacc gtcaataagg tttgcggctc tggcctgaag agcgtggccc     1920
tggcagcaca agcgattcaa gccggtcagg cacaaagcat cgttgcgggt ggcatggaga     1980
acatgtctct ggcgccgtac ttattagatg ccaaagcccg cagcggttat cgcctgggcg     2040
atggtcaggt gtacgacgtc atcttacgcg atggcttaat gtgcgcgacc cacggttacc     2100
acatgggtat tacggccgaa aacgtggcga agaatacgg cattacgcgc gagatgcagg      2160
atgaattagc actgcactct cagcgcaaag cagcagccgc gatcgagtct ggtgcgttta     2220
cggcggaaat cgtgccagtt aacgtggtca cgcgcaagaa gacgttcgtt ttcagccagg     2280
acgagttccc gaaggcaaac agcaccgcgg aggccttagg tgccttacgc ccagcctttg     2340
acaaagcggg cacggtcacc gccggtaatg cgagcggcat caatgatggt gcagcggcac     2400
tggtcatcat ggaagagagc gccgcattag cagcgggtct gaccccatta gcgcgcatta     2460
aatcttatgc cagcggcggc gtcccaccag ccctgatggg catgggtccg gtcccagcca     2520
cgcaaaaagc cctgcaatta gcgggcctgc aactggccga cattgatctg atcgaggcga     2580
acgaggcgtt tgcagcgcag ttcctggcgg tgggtaagaa tctgggcttc gacagcgaga     2640
aagtcaatgt gaacggtggc gcgattgcgt taggccatcc gattggtgca agcggcgcac     2700
gcatcttagt gacgttactg cacgccatgc aggcacgcga caagacctta ggcctggcga     2760
ccttatgtat tggtggcggt caaggtatcg ccatggtgat cgaacgcctg aactgaagat     2820
ctaggaggaa agcaaaatga aactgagcac caagctgtgc tggtgtggca tcaagggtcg     2880
cctgcgccca caaagcagc aacagctgca caacacgaac ctgcaaatga ccgagctgaa      2940
aaagcagaag acggccgagc aaaagacccg cccgcagaac gttggcatca agggcatcca     3000
```

```
gatttatatc cgacgcagt gtgtcaacca atctgagctg gagaaattcg atggcgtcag    3060
ccagggtaag tacaccatcg gcctgggcca gaccaacatg agcttcgtga acgaccgtga    3120
ggacatctat tctatgagcc tgacggtgct gtctaagctg atcaagagct acaacatcga    3180
cacgaataag atcggtcgtc tggaggtggg tacggagacg ctgattgaca agagcaaaag    3240
cgtgaagtct gtcttaatgc agctgttcgg cgagaacacg gatgtcgagg gtatcgacac    3300
cctgaacgcg tgttacggcg gcaccaacgc actgttcaat agcctgaact ggattgagag    3360
caacgcctgg gatggccgcg atgcgatcgt cgtgtgcggc gatatcgcca tctatgacaa    3420
gggtgcggca cgtccgaccg gcggtgcagg caccgttgcg atgtggattg gcccggacgc    3480
accaattgtc ttcgattctg tccgcgcgtc ttacatggag cacgcctacg acttttacaa    3540
gccggacttc acgagcgaat acccgtacgt ggacggccac ttctctctga cctgctatgt    3600
gaaggcgctg gaccaggttt ataagtctta tagcaaaaag gcgatttcta agggcctggt    3660
cagcgacccg gcaggcagcg acgccctgaa cgtgctgaag tatttcgact acaacgtgtt    3720
ccatgtcccg acctgcaaat tagtgaccaa atcttatggc cgcctgttat ataatgattt    3780
ccgtgccaac ccgcagctgt tcccggaggt tgacgccgag ctggcgacgc gtgattacga    3840
cgagagcctg accgacaaga acatcgagaa gaccttcgtc aacgtcgcga agccgttcca    3900
caaagagcgt gtgccccaaa gcctgatcgt cccgaccaac acgggcaaca tgtataccgc    3960
gtctgtctac gcggcattcg cgagcctgct gaattacgtc ggttctgacg acctgcaggg    4020
caagcgcgtt ggcctgttca gctacggtag cggcttagcg gccagcctgt atagctgcaa    4080
aattgtcggc gacgtccagc acatcatcaa ggagctggac atcaccaaca gctggcgaa    4140 gcgcatcacc gagacgccga aagattacga ggcagcgatc gagttacgcg agaatgcgca    4200
tctgaagaag aacttcaagc cgcaaggtag catcgagcac ctgcagagcg cgtctacta    4260 cctgacgaac attgacgaca agttccgccg ttcttatgac gtcaaaaagt aactagtagg    4320
aggaaaacat catggtgctg acgaacaaaa ccgtcattag cggcagcaag gtgaagtctc    4380
tgagcagcgc ccaaagctct agcagcggcc cgtctagcag cagcgaggag gacgacagcc    4440
gtgacattga gtctctggac aagaagatcc gcccgctgga ggagttagag gccctgctga    4500
gcagcggcaa caccaagcag ctgaagaaca aggaagttgc agcgctggtg atccacggta    4560
agctgccact gtatgcgctg aaaagaaac tgggcgatac gacgcgtgcg gtcgcggtgc    4620
gtcgcaaagc cttaagcatc ttagcggagg ccccggtgtt agccagcgac cgcctgccgt    4680
acaagaacta cgactacgac cgcgtgtttg gcgcgtgctg cgagaatgtc attggctaca    4740
tgccgttacc ggttggtgtg atcggcccgc tggtcattga tggcacgagc tatcacattc    4800
caatggcgac cacggaaggt tgcttagtcg ccagcgccat gcgtggctgt aaggcgatta    4860
acgccggcgg tggcgcgacg accgtgttaa ccaaggatgg tatgacgcgc ggtccggtcg    4920
tccgcttccc aacgctgaag cgcagcggcg cgtgtaagat ttggctggat tctgaggagg    4980
gccaaaacgc gatcaagaaa gccttcaact ctacgagccg tttcgcgcgt ttacagcata    5040
tccagacctg cctggccggc gacctgctgt tcatgcgctt ccgcaccacc acgggcgatg    5100
cgatgggcat gaacatgatc agcaagggcg tcgaatatag cctgaaacaa atggtggaag    5160
aatatgcgct ggaggacatg gaggttgtct ctgtgagcgg caactattgc accgacaaga    5220
agccggcagc cattaactgg attgagggtc gcggcaaaag cgtcgtggca gaagcgacca    5280
tcccaggcga cgtggtccgt aaggttctga agagcgacgt cagcgccctg gttgagttaa    5340
atatcgcgaa aaacctggtc ggcagcgcga tggcgggcag cgtgggtggc tttaacgcac    5400
```

```
atgcagcgaa tctggttacg gcggttttct tagccttagg tcaggaccca gcccaaaatg    5460
tcgagagcag caactgcatt accttaatga aagaggttga cggtgacctg cgcatcagcg    5520
tttctatgcc gtctatcgag gtcggcacga tcggcggcgg caccgtttta gaaccgcaag    5580
gtgcgatgct ggatctgctg ggcgtgcgcg gcccacatgc aacggcccca ggcaccaatg    5640
cccgccaact ggcccgtatc gtggcctgcg cggttctggc gggtgagctg agcctgtgcg    5700
ccgcattagc cgcgggccat ttagttcaat ctcacatgac ccacaaccgc aagccggcag    5760
aaccaaccaa gccaaataac ctggacgcaa ccgacattaa ccgtctgaag gatggcagcg    5820
tcacgtgcat taaaagctga gcatgctact aagcttggct gttttggcgg atgagagaag    5880
attttcagcc tgatacagat taaatcagaa cgcagaagcg gtctgataaa acagaatttg    5940
cctggcggca gtagcgcggt ggtcccacct gaccccatgc cgaactcaga agtgaaacgc    6000
cgtagcgccg atggtagtgt ggggtctccc catgcgagag tagggaactg ccaggcatca    6060
aataaaacga aaggctcagt cgaaagactg gcctttcgt tttatctgtt gtttgtcggt    6120
gaacgctctc ctgagtagga caaatccgcc gggagcggat ttgaacgttg cgaagcaacg    6180
gcccggaggg tggcgggcag gacgcccgcc ataaactgcc aggcatcaaa ttaagcagaa    6240
ggccatcctg acggatggcc ttttttgcgtt tctacaaact cttttgttta ttttttctaaa    6300 tacattcaaa tatgtatccg ctcatgagac aataaccctg cgatcgccga gaggctttac    6360
actttatgct tccggctcgt ataatgtgtg gaattgtgag cggataacaa ttgaattcaa    6420
aggaggctcg agatgtcatt accgttctta acttctgcac cgggaaaggt tattattttt    6480
ggtgaacact ctgctgtgta caacaagcct gccgtcgctg ctagtgtgtc tgcgttgaga    6540
acctacctgc taataagcga gtcatctgca ccagatacta ttgaattgga cttcccggac    6600
attagcttta atcataagtg gtccatcaat gatttcaatg ccatcaccga ggatcaagta    6660
aactcccaaa aattggccaa ggctcaacaa gccaccgatg gcttgtctca ggaactcgtt    6720
agtcttttgg atccgttgtt agctcaacta tccgaatcct tccactacca tgcagcgttt    6780 tgttttcctgt atatgtttgt ttgcctatgc ccccatgcca agaatattaa gttttcttta    6840
aagtctactt tacccatcgg tgctgggttg ggctcaagcg cctctatttc tgtatcactg    6900
gccttagcta tggcctactt gggggggtta ataggatcta atgacttgga aaagctgtca    6960
gaaaacgata agcatatagt gaatcaatgg gccttcatag gtgaaaagtg tattcacggt    7020
accccttcag gaatagataa cgctgtggcc acttatggta atgccctgct atttgaaaaa    7080
gactcacata atggaacaat aaacacaaac aattttaagt tcttagatga tttcccagcc    7140
attccaatga tcctaaccta tactagaatt ccaaggtcta caaaagatct tgttgctcgc    7200
gttcgtgtgt tggtcaccga gaaatttcct gaagttatga agccaattct agatgccatg    7260
ggtgaatgtg ccctacaagg cttagagatc atgactaagt taagtaaatg taaaggcacc    7320
gatgacgagg ctgtagaaac taataatgaa ctgtatgaac aactattgga attgataaga    7380
ataaatcatg gactgcttgt ctcaatcggt gtttctcatc ctggattaga acttattaaa    7440
aatctgagcg atgatttgag aattggctcc acaaaactta ccggtgctgg tggcggcggt    7500 tgctctcttga ctttgttacg aagagacatt actcaagagc aaattgacag cttcaaaaag    7560
aaattgcaag atgattttag ttacgagaca tttgaaacag acttgggtgg gactggctgc    7620
tgtttgttaa gcgcaaaaaa tttgaataaa gatcttaaaa tcaaatccct agtattccaa    7680
ttatttgaaa ataaaactac cacaaagcaa caaattgacg atctattatt gccaggaaac    7740
acgaatttac catggacttc ataggaggca gatcaaatgt cagagttgag agccttcagt    7800
```

```
gccccaggga aagcgttact agctggtgga tatttagttt tagatacaaa atatgaagca   7860
tttgtagtcg gattatcggc aagaatgcat gctgtagccc atccttacgg ttcattgcaa   7920
gggtctgata agtttgaagt gcgtgtgaaa agtaaacaat ttaaagatgg ggagtggctg   7980
taccatataa gtcctaaaag tggcttcatt cctgtttcga taggcggatc taagaacccct  8040
ttcattgaaa aagttatcgc taacgtattt agctaccttta aacctaacat ggacgactac   8100
tgcaatagaa acttgttcgt tattgatatt ttctctgatg atgcctacca ttctcaggag   8160
gatagcgtta ccgaacatcg tggcaacaga agattgagtt ttcattcgca cagaattgaa   8220
gaagttccca aaacagggct gggctcctcg gcaggtttag tcacagtttt aactacagct   8280
ttggcctcct tttttgtatc ggacctggaa ataatgtag acaaatatag agaagttatt    8340
cataatttag cacaagttgc tcattgtcaa gctcagggta aaattggaag cgggtttgat   8400
gtagcggcgg cagcatatgg atctatcaga tatagaagat tcccacccgc attaatctct   8460
aatttgccag atattggaag tgctacttac ggcagtaaac tggcgcattt ggttgatgaa   8520
gaagactgga atattacgat taaaagtaac catttacctt cgggattaac tttatggatg   8580
ggcgatatta agaatggttc agaaacagta aaactggtcc agaaggtaaa aaattggtat   8640
gattcgcata tgccagaaag cttgaaaata tatacagaac tcgatcatgc aaattctaga   8700
tttatggatg gactatctaa actagatcgc ttacacgaga ctcatgacga ttacagcgat   8760
cagatatttg agtctcttga gaggaatgac tgtacctgtc aaaagtatcc tgaaatcaca   8820
gaagttagag atgcagttgc cacaattaga cgttccttta aaaaataac taagaatct    8880
ggtgccgata tcgaacctcc cgtacaaact agcttattgg atgattgcca gaccttaaaa   8940
ggagttctta cttgcttaat acctggtgct ggtggttatg acgccattgc agtgattact   9000
aagcaagatg ttgatcttag ggctcaaacc gctaatgaca aaagattttc taaggttcaa   9060
tggctgatg taactcaggc tgactggggt gttaggaaag aaaaagatcc ggaaacttat    9120
cttgataaat aggaggtaat actcatgacc gtttacacag catccgttac cgcacccgtc   9180
aacatcgcaa cccttaagta ttgggggaaa agggacacga agttgaatct gcccaccaat   9240
tcgtccatat cagtgacttt atcgcaagat gacctcagaa cgttgacctc tgcggctact   9300
gcacctgagt ttgaacgcga cactttgtgg ttaaatggag aaccacacag catcgacaat   9360
gaaagaactc aaaattgtct gcgcgaccta cgccaattaa gaaaggaaat ggaatcgaag   9420
gacgcctcat tgcccacatt atctcaatgg aaactccaca ttgtctccga aaataacttt   9480
cctacagcag ctggtttagc ttcctccgct gctggctttg ctgcattggt ctctgcaatt   9540
gctaagttat accaattacc acagtcaact tcagaaatat ctagaatagc aagaaagggg   9600
tctggttcag cttgtagatc gttgtttggc ggatacgtgg cctgggaaat gggaaaagct   9660
gaagatggtc atgattccat ggcagtacaa atcgcagaca gctctgactg gcctcagatg   9720
aaagcttgtg tcctagttgt cagcgatatt aaaaaggatg tgagttccac tcagggtatg   9780
caattgaccg tggcaacctc cgaactattt aagaaagaa ttgaacatgt cgtaccaaag    9840
agatttgaag tcatgcgtaa agccattgtt gaaaagatt tcgccacctt tgcaaaggaa    9900
acaatgatgg attccaactc ttttccatgcc acatgtttgg actctttccc tccaatattc   9960
tacatgaatg acacttccaa gcgtatcatc agttggtgcc acaccattaa tcagttttac  10020
ggagaaacaa tcgttgcata cacgtttgat gcaggtccaa atgctgtgtt gtactactta  10080
gctgaaaatg agtcgaaact cttttgcattt atctataaat tgtttggctc tgttcctgga  10140
tgggacaaga aatttactac tgagcagctt gaggctttca accatcaatt tgaatcatct  10200
```

```
aactttactg cacgtgaatt ggatcttgag ttgcaaaagg atgttgccag agtgatttta   10260
actcaagtcg gttcaggccc acaagaaaca aacgaatctt tgattgacgc aaagactggt   10320
ctaccaaagg aataactgca gcccgggagg aggattacta tatgcaaacg gaacacgtca   10380
ttttattgaa tgcacaggga gttcccacgg gtacgctgga aaagtatgcc gcacacacgg   10440
cagacacccg cttacatctc gcgttctcca gttggctgtt taatgccaaa ggacaattat   10500
tagttacccg ccgcgcactg agcaaaaaag catggcctgg cgtgtggact aactcggttt   10560
gtgggcaccc acaactggga gaaagcaacg aagacgcagt gatccgccgt tgccgttatg   10620
agcttggcgt ggaaattacg cctcctgaat ctatctatcc tgactttcgc taccgcgcca   10680
ccgatccgag tggcattgtg gaaaatgaag tgtgtccggt atttgccgca cgcaccacta   10740
gtgcgttaca gatcaatgat gatgaagtga tggattatca atggtgtgat ttagcagatg   10800
tattacacgg tattgatgcc acgccgtggg cgttcagtcc gtggatggtg atgcaggcga   10860
caaatcgcga agccagaaaa cgattatctg catttaccca gcttaaataa cccgggggat   10920
ccactagttc tagagcggcc gccaccgcgg aggaggaatg agtaatggac tttccgcagc   10980
aactcgaagc ctgcgttaag caggccaacc aggcgctgag ccgttttatc gccccactgc   11040
cctttcagaa cactcccgtg gtcgaaacca tgcagtatgg cgcattatta ggtggtaagc   11100
gcctgcgacc tttcctggtt tatgccaccg gtcatatgtt cggcgttagc acaaacacgc   11160
tggacgcacc cgctgccgcc gttgagtgta tccacgctta ctcattaatt catgatgatt   11220
taccggcaat ggatgatgac gatctgcgtc gcggtttgcc aacctgccat gtgaagtttg   11280
gcgaagcaaa cgcgattctc gctggcgacg ctttacaaac gctggcgttc tcgattttaa   11340
gcgatgccga tatgccggaa gtgtcggacc gcgacagaat ttcgatgatt tctgaactgg   11400
cgagcgccag tggtattgcc ggaatgtgcg gtggtcaggc attagattta gacgcggaag   11460
gcaaacacgt acctctggac gcgcttgagc gtattcatcg tcataaaacc ggcgcattga   11520
ttcgcgccgc cgttcgcctt ggtgcattaa gcgccggaga taaggacgt cgtgctctgc   11580 cggtactcga caagtatgca gagagcatcg gccttgcctt ccaggttcag gatgacatcc   11640
tggatgtggt gggagatact gcaacgttgg gaaaacgcca gggtgccgac cagcaacttg   11700
gtaaaagtac ctaccctgca cttctgggtc ttgagcaagc ccggaagaaa gcccgggatc   11760
tgatcgacga tgcccgtcag tcgctgaaac aactggctga acagtcactc gatacctcgg   11820
cactggaagc gctagcggac tacatcatcc agcgtaataa ataagagctc caattcgccc   11880
tatagtgaga cgcgtgctag aggcatcaaa taaaacgaaa ggctcagtcg aaagactggg   11940
cctttcgttt tatctgttgt ttgtcggtga acgctctcct gagttaatta actccaggcc   12000
ggcctacgcg tttaaacttc cggttaacgc catgagcggc ctcatttctt attctgagtt   12060
acaacagtcc gcaccgctgc cggtagctcc ttccggtggg cgcggggcat gactatcgtc   12120
gccgcactta tgactgtctt ctttatcatg caactcgtag acaggtgcc ggcagcgccc   12180 aacagtcccc cggccacggg gcctgccacc atacccacgc cgaaacaagc gccctgcacc   12240
attatgttcc ggatctgcat cgcaggatgc tgctggctac cctgtggaac acctacatct   12300
gtattaacga agcgctaacc gttttttatca ggctctggga ggcagaataa atgatcatat   12360
cgtcaattat tacctccacg gggagagcct gagcaaactg gcctcaggca tttgagaagc   12420
acacggtcac actgcttccg gtagtcaata aaccggtaaa ccagcaatag acataagcgg   12480
ctatttaacg accctgccct gaaccgacga ccgggtcgaa tttgctttcg aatttctgcc   12540
attcatccgc ttattatcac ttattcaggc gtagcaccag gcgtttaagg gcaccaataa   12600
```

| | |
|---|---|
| ctgccttaaa aaaattacgc cccgccctgc cactcatcgc agtactgttg taattcatta | 12660 |
| agcattctgc cgacatggaa gccatcacag acggcatgat gaacctgaat cgccagcggc | 12720 |
| atcagcacct tgtcgccttg cgtataatat ttgcccatgg tgaaaacggg ggcgaagaag | 12780 |
| ttgtccatat tggccacgtt taaatcaaaa ctggtgaaac tcacccaggg attggctgag | 12840 |
| acgaaaaaca tattctcaat aaacccttta gggaaatagg ccaggttttc accgtaacac | 12900 |
| gccacatctt gcgaatatat gtgtagaaac tgccggaaat cgtcgtggta ttcactccag | 12960 |
| agcgatgaaa acgtttcagt ttgctcatgg aaaacggtgt aacaagggtg aacactatcc | 13020 |
| catatcacca gctcaccgtc tttcattgcc atacg | 13055 |

<210> SEQ ID NO 6
<211> LENGTH: 7120
<212> TYPE: DNA
<213> ORGANISM: Artificial Sequence
<220> FEATURE:
<223> OTHER INFORMATION: recombinant vector

<400> SEQUENCE: 6

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagaccatgg ccctgaccga agagaaaccg atccgcccga | 300 |
| tcgctaactt cccgccgtct atctggggtg accagttcct gatctacgaa agcaggttg | 360 |
| agcagggtgt tgaacagatc gtaaacgacc tgaagaaaga agttcgtcag ctgctgaaag | 420 |
| aagctctgga catcccgatg aaacacgcta acctgctgaa actgatcgac gagatccagc | 480 |
| gtctgggtat cccgtaccac ttcgaacgcg aaatcgacca cgcactgcag tgcatctacg | 540 |
| aaacctacgg cgacaactgg aacggcgacc gttcttctct gtggtttcgt ctgatgcgta | 600 |
| aacagggcta ctacgttacc tgtgacgttt taacaacta caaggacaag aacggtgctt | 660 |
| tcaaacagtc tctggctaac gacgttgaag gcctgctgga actgtacgaa gcgacctcca | 720 |
| tgcgtgtacc gggtgaaatc atcctggagg acgcgctggg tttcacccgt tctcgtctgt | 780 |
| ccattatgac taaagacgct ttctctacta acccggctct gttcaccgaa atccagcgtg | 840 |
| ctctgaaaca gccgctgtgg aaacgtctgc cgcgtatcga agcagcacag tacattccgt | 900 |
| tttaccagca gcaggactct cacaacaaga ccctgctgaa actggctaag ctggaattca | 960 |
| acctgctgca gtctctgcac aaagaagaac tgtctcacgt ttgtaagtgg tggaaggcat | 1020 |
| ttgacatcaa gaaaaacgcg ccgtgcctgc gtgaccgtat cgttgaatgt tacttctggg | 1080 |
| gtctgggttc tggttatgaa ccacagtact cccgtgcacg tgtgttcttc actaaagctg | 1140 |
| tagctgttat caccctgatc gatgacactt acgatgctta cggcacctac gaagaactga | 1200 |
| agatctttac tgaagctgta gaacgctggt ctatcacttg cctggacact ctgccggagt | 1260 |
| acatgaaacc gatctacaaa ctgttcatgg ataccctacac cgaaatggag gaattcctgg | 1320 |
| caaaagaagg ccgtaccgac ctgttcaact gcggtaaaga gtttgttaaa gaattcgtac | 1380 |
| gtaacctgat ggttgaagct aaatgggcta acgaaggcca tatcccgact accgaagaac | 1440 |
| atgacccggt tgttatcatc accggcggtg caaacctgct gaccaccact tgctatctgg | 1500 |
| gtatgtccga catctttacc aaggaatctg ttgaatgggc tgtttctgca ccgccgctgt | 1560 |
| tccgttactc cggtattctg ggtcgtcgtc tgaacgacct gatgacccac aaagcagagc | 1620 |

```
aggaacgtaa acactcttcc tcctctctgg aatcctacat gaaggaatat aacgttaacg   1680
aggagtacgc acagactctg atctataaag aagttgaaga cgtatggaaa gacatcaacc   1740
gtgaatacct gactactaaa aacatcccgc gcccgctgct gatggcagta atctacctgt   1800
gccagttcct ggaagtacag tacgctggta agataacctt cactcgcatg ggcgacgaat   1860
acaaacacct gatcaaatcc ctgctggttt acccgatgtc catctgatcc cggggatcca   1920
ggaggaaata accatgtctc tgccattcct gacgtctgcg ccaggtaagg tgatcatctt   1980
cggcgagcac tctgcggtgt acaataagcc ggccgtcgcc gcctctgtgt ctgcgttacg   2040
cacctacctg ctgatcagcg aatcttctgc accggacacg atcgagctgg actttccgga   2100
catcagcttc aaccacaagt ggagcatcaa cgacttcaac gcgatcacgg aggaccaggt   2160
gaacagccaa aagctggcca aagcccagca agcaaccgac ggtctgtctc aggagctggt   2220
gtctctgctg gacccgctgt tagcgcagtt aagcgagagc ttccattacc acgccgcgtt   2280
ctgcttcctg tacatgttcg tttgcctgtg cccgcacgca aagaacatca agttcagcct   2340
gaagagcacg ctgccgattg gcgcaggctt aggctctagc gcatctatca gcgtgagcct   2400
ggcgctggcg atggcctatc tgggtggcct gattggcagc aacgacctgg agaaactgag   2460
cgaaaacgac aagcacatcg tgaaccagtg ggcctttatc ggcgagaagt gcattcatgg   2520
cacccccagc ggcattgaca acgcagttgc cacgtatggc aacgccctgc tgttcgagaa   2580
agacagccac aacggcacga tcaacacgaa caacttcaag ttcctggacg acttcccggc   2640
gatcccgatg attctgacct acacccgtat cccacgcagc accaaggatt tagtcgcccg   2700
cgtgcgtgtt ttagtcaccg aaaagttccc ggaggtgatg aagccgatcc tggacgcgat   2760
gggcgagtgc gcgctgcagg gtctggagat catgaccaag ctgagcaagt gcaagggcac   2820
cgacgatgag gcggtggaga ccaacaatga gctgtacgag cagctgctgg agctgatccg   2880
tatcaatcac ggcctgctgg tctctatcgg tgtgtctcac ccgggcctgg aactgatcaa   2940
aaacctgagc gacgacctgc gcattggctc tacgaaatta acgggtgcag gtggcggtgg   3000
ctgctcttta acgctgctgc gccgtgacat tacgcaggaa caaatcgaca gcttcaagaa   3060
gaagctgcag gacgacttca gctacgagac gttcgagacg gacctgggcg gcacgggctg   3120
ttgcctgctg agcgccaaaa atctgaacaa ggacctgaag atcaaaagcc tggtgttcca   3180
gctgttcgaa aacaagacga ccacgaagca gcagatcgac gacctgttac tgccgggtaa   3240
caccaatctg ccgtggacgt cttaaagctt ggctgttttg gcggatgaga gaagattttc   3300
agcctgatac agattaaatc agaacgcaga agcggtctga taaaacagaa tttgcctggc   3360
ggcagtagcg cggtggtccc acctgacccc atgccgaact cagaagtgaa acgccgtagc   3420
gccgatggta gtgtggggtc tccccatgcg agagtaggga actgccaggc atcaaataaa   3480
acgaaaggct cagtcgaaag actgggcctt tcgttttatc tgttgtttgt cggtgaacgc   3540
tctcctgagt aggacaaatc cgccgggagc ggatttgaac gttgcgaagc aacggcccgg   3600
agggtggcgg gcaggacgcc cgccataaac tgccaggcat caaattaagc agaaggccat   3660
cctgacggat ggcctttttg cgtttctaca actcttttt gtttattttt ctaaatacat   3720
tcaaatatgt atccgctcat gagacaataa ccctgataaa tgcttcaata atattgaaaa   3780
aggaagagta tgagtattca acatttccgt gtcgccctta ttcccttttt tgcggcattt   3840
tgccttcctg ttttgctcac ccagaaacg ctggtgaaag taaaagatgc tgaagatcag   3900
ttgggtgcac gagtgggtta catcgaactg gatctcaaca gcggtaagat ccttgagagt   3960
tttcgccccg aagaacgttt tccaatgatg agcactttta aagttctgct atgtggcgcg   4020
```

```
gtattatccc gtgttgacgc cgggcaagag caactcggtc gccgcataca ctattctcag    4080
aatgacttgg ttgagtactc accagtcaca gaaaagcatc ttacggatgg catgacagta    4140
agagaattat gcagtgctgc cataaccatg agtgataaca ctgcggccaa cttacttctg    4200
acaacgatcg gaggaccgaa ggagctaacc gctttttgc acaacatggg ggatcatgta     4260
actcgccttg atcgttggga accggagctg aatgaagcca taccaaacga cgagcgtgac    4320
accacgatgc ctacagcaat ggcaacaacg ttgcgcaaac tattaactgg cgaactactt    4380
actctagctt cccggcaaca attaatagac tggatggagg cggataaagt tgcaggacca    4440
cttctgcgct cggcccttcc ggctggctgg tttattgctg ataaatctgg agccggtgag    4500
cgtgggtctc gcggtatcat tgcagcactg gggccagatg gtaagccctc ccgtatcgta    4560
gttatctaca cgacggggag tcaggcaact atggatgaac gaaatagaca gatcgctgag    4620
ataggtgcct cactgattaa gcattggtaa ctgtcagacc aagtttactc atatatactt    4680
tagattgatt taaaacttca tttttaattt aaaaggatct aggtgaagat cctttttgat    4740
aatctcatga ccaaaatccc ttaacgtgag ttttcgttcc actgagcgtc agaccccgta    4800
gaaaagatca aggatcttc ttgagatcct tttttctgc gcgtaatctg ctgcttgcaa      4860
acaaaaaaac caccgctacc agcggtggtt tgtttgccgg atcaagagct accaactctt    4920
tttccgaagg taactggctt cagcagagcg cagataccaa atactgtcct tctagtgtag    4980
ccgtagttag gccaccactt caagaactct gtagcaccgc ctacatacct cgctctgcta    5040
atcctgttac cagtggctgc tgccagtggc gataagtcgt gtcttaccgg gttggactca    5100
agacgatagt taccggataa ggcgcagcgg tcgggctgaa cggggggttc gtgcacacag    5160
cccagcttgg agcgaacgac ctacaccgaa ctgagatacc tacagcgtga gctatgagaa    5220
agcgccacgc ttcccgaagg gagaaaggcg gacaggtatc cggtaagcgg cagggtcgga    5280
acaggagagc gcacgaggga gcttccaggg ggaaacgcct ggtatcttta tagtcctgtc    5340
gggtttcgcc acctctgact tgagcgtcga ttttgtgat gctcgtcagg ggggcggagc     5400
ctatggaaaa acgccagcaa cgcggccttt ttacggttcc tggccttttg ctggcctttt    5460
gctcacatgt tctttcctgc gttatcccct gattctgtgg ataaccgtat taccgccttt    5520
gagtgagctg ataccgctcg ccgcagccga acgaccgagc gcagcgagtc agtgagcgag    5580
gaagcggaag agcgcctgat gcggtatttt ctccttacgc atctgtgcgg tatttcacac    5640
cgcatatggt gcactctcag tacaatctgc tctgatgccg catagttaag ccagtataca    5700
ctccgctatc gctacgtgac tgggtcatgg ctgcgccccg acacccgcca acacccgctg    5760
acgcgccctg acgggcttgt ctgctcccgg catccgctta cagacaagct gtgaccgtct    5820
ccgggagctg catgtgtcag aggttttcac cgtcatcacc gaaacgcgcg aggcagcaga    5880
tcaattcgcg cgcgaaggcg aagcggcatg catttacgtt gacaccatcg aatggtgcaa    5940
aacctttcgc ggtatggcat gatagcgccc ggaagagagt caattcaggg tggtgaatgt    6000
gaaaccagta acgttatacg atgtcgcaga gtatgccggt gtctcttatc agaccgtttc    6060
ccgcgtggtg aaccaggcca gccacgtttc tgcgaaaacg cgggaaaaag tggaagcggc    6120
gatggcggag ctgaattaca ttcccaaccg cgtggcacaa caactggcgg gcaaacagtc    6180
gttgctgatt ggcgttgcca cctccagtct ggccctgcac gcgccgtcgc aaattgtcgc    6240
ggcgattaaa tctcgcgccg atcaactggg tgccagcgtg gtggtgtcga tggtagaacg    6300
aagcggcgtc gaagcctgta aagcggcggt gcacaatctt ctcgcgcaac gcgtcagtgg    6360
gctgatcatt aactatccgc tggatgacca ggatgccatt gctgtggaag ctgcctgcac    6420
```

-continued

```
taatgttccg gcgttatttc ttgatgtctc tgaccagaca cccatcaaca gtattatttt    6480
ctcccatgaa gacggtacgc gactgggcgt ggagcatctg gtcgcattgg gtcaccagca    6540
aatcgcgctg ttagcgggcc cattaagttc tgtctcggcg cgtctgcgtc tggctggctg    6600
gcataaatat ctcactcgca atcaaattca gccgatagcg gaacgggaag gcgactggag    6660
tgccatgtcc ggttttcaac aaaccatgca aatgctgaat gagggcatcg ttcccactgc    6720
gatgctggtt gccaacgatc agatggcgct gggcgcaatg cgcgccatta ccgagtccgg    6780
gctgcgcgtt ggtgcggata tctcggtagt gggatacgac gataccgaag acagctcatg    6840
ttatatcccg ccgtcaacca ccatcaaaca ggattttcgc ctgctggggc aaaccagcgt    6900
ggaccgcttg ctgcaactct ctcagggcca ggcggtgaag gcaatcagc tgttgcccgt     6960 ctcactggtg aaaagaaaaa ccaccctggc gcccaatacg caaaccgcct ctccccgcgc    7020
gttggccgat tcattaatgc agctggcacg acaggtttcc cgactggaaa gcgggcagtg    7080
agcgcaacgc aattaatgtg agttagcgcg aattgatctg                          7120
```

<210> SEQ ID NO 7
<211> LENGTH: 36
<212> TYPE: DNA
<213> ORGANISM: Artificial Sequence
<220> FEATURE:
<223> OTHER INFORMATION: primer
<400> SEQUENCE: 7

```
ttctgggccc atgtcattac cgttcttaac ttctgc                              36
```

<210> SEQ ID NO 8
<211> LENGTH: 35
<212> TYPE: DNA
<213> ORGANISM: Artificial Sequence
<220> FEATURE:
<223> OTHER INFORMATION: primer
<400> SEQUENCE: 8

```
gggcacgcgt ctcactatag ggcgaattgg agctc                               35
```

<210> SEQ ID NO 9
<211> LENGTH: 34
<212> TYPE: DNA
<213> ORGANISM: Artificial Sequence
<220> FEATURE:
<223> OTHER INFORMATION: primer
<400> SEQUENCE: 9

```
agtgtcgaca ggaggaatta accatgtcat tacc                                34
```

<210> SEQ ID NO 10
<211> LENGTH: 32
<212> TYPE: DNA
<213> ORGANISM: Artificial Sequence
<220> FEATURE:
<223> OTHER INFORMATION: primer
<400> SEQUENCE: 10

```
tacaagcttc tatgaagtcc atggtaaatt cg                                  32
```

<210> SEQ ID NO 11
<211> LENGTH: 35
<212> TYPE: DNA
<213> ORGANISM: Artificial Sequence
<220> FEATURE:
<223> OTHER INFORMATION: primer

```
<400> SEQUENCE: 11
agtgaattca ggaggcagat caaatgtcag agttg                35

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
tacgtcgacc tatttatcaa gataagtttc                     30

<210> SEQ ID NO 13
<211> LENGTH: 35
<212> TYPE: DNA
<213> ORGANISM: Artificial Sequence
<220> FEATURE:
<223> OTHER INFORMATION: primer

<400> SEQUENCE: 13
agtgaattca ggaggtaata ctcatgaccg tttac                35

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14
tacgtcgact tattcctttg gtagaccagt c                   31

<210> SEQ ID NO 15
<211> LENGTH: 36
<212> TYPE: DNA
<213> ORGANISM: artifical sequence

<400> SEQUENCE: 15
tcagaattca ggaggattac tatatgcaaa cggaac              36

<210> SEQ ID NO 16
<211> LENGTH: 38
<212> TYPE: DNA
<213> ORGANISM: Artificial Sequence
<220> FEATURE:
<223> OTHER INFORMATION: primer

<400> SEQUENCE: 16
agagtcgact tatttaagct gggtaaatgc agataatc            38

<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17
tcagaattca ggaggaatga gtaatggact ttcc                34

<210> SEQ ID NO 18
<211> LENGTH: 36
<212> TYPE: DNA
<213> ORGANISM: Artificial Sequence
```

```
<220> FEATURE:
<223> OTHER INFORMATION: primer

<400> SEQUENCE: 18
agagtcgact tatttattac gctggatgat gtagtc                                    36

<210> SEQ ID NO 19
<211> LENGTH: 34
<212> TYPE: DNA
<213> ORGANISM: Artificial Sequence
<220> FEATURE:
<223> OTHER INFORMATION: primer

<400> SEQUENCE: 19
cgcggatcca ggaggaaata accatgtctc tgcc                                      34

<210> SEQ ID NO 20
<211> LENGTH: 34
<212> TYPE: DNA
<213> ORGANISM: Artificial Sequence
<220> FEATURE:
<223> OTHER INFORMATION: primer

<400> SEQUENCE: 20
ccgcaagctt taagacgtcc acggcagatt ggtg                                      34

<210> SEQ ID NO 21
<211> LENGTH: 93
<212> TYPE: DNA
<213> ORGANISM: Artificial Sequence
<220> FEATURE:
<223> OTHER INFORMATION: promoter

<400> SEQUENCE: 21
caacgcaatt aatgtgagtt agctcactca ttaggcaccc caggctttac actttatgct          60
tccggctcgt atgttgtgtg gaattgtgag cgg                                       93

<210> SEQ ID NO 22
<211> LENGTH: 120
<212> TYPE: DNA
<213> ORGANISM: Artificial Sequence
<220> FEATURE:
<223> OTHER INFORMATION: promoter

<400> SEQUENCE: 22
gacgtctaag aaaccattat tatcatgaca ttaacctata aaaataggcg tatcacgagg          60 cccttttcgtc ttcacctcga gaggctttac actttatgct tccggctcgt ataatgtgtg       120
```